US011278686B2

(12) United States Patent
Collett et al.

(10) Patent No.: US 11,278,686 B2
(45) Date of Patent: Mar. 22, 2022

(54) METHODS FOR ASSEMBLING A CARTRIDGE FOR AN AEROSOL DELIVERY DEVICE, AND ASSOCIATED SYSTEMS AND APPARATUSES

(71) Applicant: RAI Strategic Holdings, Inc., Winston-Salem, NC (US)

(72) Inventors: William Robert Collett, Lexington, NC (US); Quentin Paul Guenther, Jr., Winston-Salem, NC (US); Paul Andrew Brinkley, Winston-Salem, NC (US); Jeffrey Edward Allgeyer, Gibsonville, NC (US); Ethan Matthew Bernhardt, Cookeville, TN (US); Andrew Ross Matthews, Cookeville, TN (US); Roger Ritter, Büren (CH); Stephen Todd Schafer, Denver, CO (US); Mathieu Leboeuf, Denver, CO (US); Martin Lee Maple, Aurora, CO (US); Trenton S. Noonan, Parker, CO (US); Kevin Paul Schafer, Lakewood, CO (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 244 days.

(21) Appl. No.: 16/517,361

(22) Filed: Jul. 19, 2019

(65) Prior Publication Data

US 2019/0335818 A1 Nov. 7, 2019

Related U.S. Application Data

(62) Division of application No. 15/142,502, filed on Apr. 29, 2016, now Pat. No. 10,405,579.

(51) Int. Cl.
*B32B 37/00* (2006.01)
*A61M 15/06* (2006.01)
(Continued)

(52) U.S. Cl.
CPC ............ *A61M 15/06* (2013.01); *A24F 40/70* (2020.01); *B23K 26/22* (2013.01); *B29C 65/08* (2013.01);
(Continued)

(58) Field of Classification Search
USPC ........................................................ 156/73.1
See application file for complete search history.

(56) References Cited

U.S. PATENT DOCUMENTS 1,771,366 A 7/1930 Wyss et al.
2,057,353 A 10/1936 Whittemore, Jr.
(Continued)

FOREIGN PATENT DOCUMENTS

AU 276250 7/1965
CA 2 641 869 5/2010
(Continued)

OTHER PUBLICATIONS

Freedom Smokeless Press Release; *Electronic Cigarettes U.S. Automated Filling, Assembly & Packaging*; Feb. 12, 2014 (2 pgs.) http://www.freedomsmokeless.com/20120212_pressrelease.pdf.
(Continued)

*Primary Examiner* — James D Sells
(74) *Attorney, Agent, or Firm* — Womble Bond Dickinson (US) LLP; Chris Humphrey; John V. Forcier

(57) ABSTRACT

The present disclosure relates to systems, apparatuses, and methods for assembling cartridges for aerosol delivery devices. A system may include assembly cells each including an assembly track and assembly carriages that ride thereon and which engage components of partially-assembled cartridges. A transfer apparatus may transfer partially-assembled cartridges between the assembly cells. In another example system, cartridges may be assembled on platforms on a rotary track. The platforms may include assembly grippers with sequentially-opening clamps configured to receive the components of the partially-assembled cartridges. Related methods are also provided.

24 Claims, 50 Drawing Sheets

(51) Int. Cl.

| | |
|---|---|
| ***A24F 40/70*** | (2020.01) |
| ***B23K 26/22*** | (2006.01) |
| ***B29C 65/08*** | (2006.01) |
| ***B29C 65/00*** | (2006.01) |
| ***B65B 3/14*** | (2006.01) |
| ***G01M 99/00*** | (2011.01) |
| ***H05B 3/00*** | (2006.01) |
| ***H05B 3/78*** | (2006.01) |
| *A61M 11/04* | (2006.01) |
| *A24F 40/10* | (2020.01) |
| *B29L 31/00* | (2006.01) |

(52) U.S. Cl.

CPC ............ *B29C 66/5344* (2013.01); *B65B 3/14* (2013.01); *G01M 99/008* (2013.01); *H05B 3/0014* (2013.01); *H05B 3/78* (2013.01); *A24F 40/10* (2020.01); *A61M 11/042* (2014.02); *A61M 2205/3334* (2013.01); *A61M 2205/3553* (2013.01); *A61M 2205/3693* (2013.01); *A61M 2207/00* (2013.01); *B29L 2031/712* (2013.01); *B29L 2031/7414* (2013.01)

(56) References Cited

U.S. PATENT DOCUMENTS

| | | | |
|---|---|---|---|
| 2,104,266 | A | 1/1938 | McCormick |
| 2,805,669 | A | 9/1957 | Meriro |
| 3,200,819 | A | 8/1965 | Gilbert |
| 3,316,919 | A | 5/1967 | Green et al. |
| 3,398,754 | A | 8/1968 | Tughan |
| 3,419,015 | A | 12/1968 | Wochnowski |
| 3,424,171 | A | 1/1969 | Rooker |
| 3,476,118 | A | 11/1969 | Luttich |
| 4,054,145 | A | 10/1977 | Berndt et al. |
| 4,131,117 | A | 12/1978 | Kite et al. |
| 4,150,677 | A | 4/1979 | Osborne |
| 4,190,046 | A | 2/1980 | Virag |
| 4,219,032 | A | 8/1980 | Tabatznik et al. |
| 4,259,970 | A | 4/1981 | Green, Jr. |
| 4,284,089 | A | 8/1981 | Ray |
| 4,303,083 | A | 12/1981 | Burruss, Jr. |
| 4,449,541 | A | 5/1984 | Mays et al. |
| 4,506,682 | A | 3/1985 | Muller |
| 4,635,651 | A | 1/1987 | Jacobs |
| 4,674,519 | A | 6/1987 | Keritsis et al. |
| 4,708,151 | A | 11/1987 | Shelar |
| 4,714,082 | A | 12/1987 | Banerjee et al. |
| 4,735,217 | A | 4/1988 | Gerth et al. |
| 4,756,318 | A | 7/1988 | Clearman et al. |
| 4,771,795 | A | 9/1988 | White et al. |
| 4,776,353 | A | 10/1988 | Lilja et al. |
| 4,793,365 | A | 12/1988 | Sensabaugh, Jr. et al. |
| 4,800,903 | A | 1/1989 | Ray et al. |
| 4,819,665 | A | 4/1989 | Roberts et al. |
| 4,821,749 | A | 4/1989 | Toft et al. |
| 4,830,028 | A | 5/1989 | Lawson et al. |
| 4,836,224 | A | 6/1989 | Lawson et al. |
| 4,836,225 | A | 6/1989 | Sudoh |
| 4,848,374 | A | 7/1989 | Chard et al. |
| 4,848,376 | A | 7/1989 | Lilja et al. |
| 4,874,000 | A | 10/1989 | Tamol et al. |
| 4,880,018 | A | 11/1989 | Graves, Jr. et al. |
| 4,887,619 | A | 12/1989 | Burcham, Jr. et al. |
| 4,907,606 | A | 3/1990 | Lilja et al. |
| 4,913,168 | A | 4/1990 | Potter et al. |
| 4,917,119 | A | 4/1990 | Potter et al. |
| 4,917,128 | A | 4/1990 | Clearman et al. |
| 4,922,901 | A | 5/1990 | Brooks et al. |
| 4,924,888 | A | 5/1990 | Perfetti et al. |
| 4,928,714 | A | 5/1990 | Shannon |
| 4,938,236 | A | 7/1990 | Banerjee et al. |
| 4,941,483 | A | 7/1990 | Ridings et al. |
| 4,941,484 | A | 7/1990 | Clapp et al. |
| 4,945,931 | A | 8/1990 | Gori |
| 4,947,874 | A | 8/1990 | Brooks et al. |
| 4,947,875 | A | 8/1990 | Brooks et al. |
| 4,972,854 | A | 11/1990 | Kiernan et al. |
| 4,972,855 | A | 11/1990 | Kuriyama et al. |
| 4,986,286 | A | 1/1991 | Roberts et al. |
| 4,987,906 | A | 1/1991 | Young et al. |
| 5,005,593 | A | 4/1991 | Fagg |
| 5,019,122 | A | 5/1991 | Clearman et al. |
| 5,022,416 | A | 6/1991 | Watson |
| 5,042,510 | A | 8/1991 | Curtiss et al. |
| 5,056,537 | A | 10/1991 | Brown et al. |
| 5,060,669 | A | 10/1991 | White et al. |
| 5,060,671 | A | 10/1991 | Counts et al. |
| 5,065,775 | A | 11/1991 | Fagg |
| 5,072,744 | A | 12/1991 | Luke et al. |
| 5,074,319 | A | 12/1991 | White et al. |
| 5,076,296 | A | 12/1991 | Nystrom et al. |
| 5,093,894 | A | 3/1992 | Deevi et al. |
| 5,095,921 | A | 3/1992 | Losee et al. |
| 5,097,850 | A | 3/1992 | Braunshteyn et al. |
| 5,099,862 | A | 3/1992 | White et al. |
| 5,099,864 | A | 3/1992 | Young et al. |
| 5,103,842 | A | 4/1992 | Strang et al. |
| 5,121,757 | A | 6/1992 | White et al. |
| 5,129,409 | A | 7/1992 | White et al. |
| 5,131,415 | A | 7/1992 | Munoz et al. |
| 5,143,097 | A | 9/1992 | Sohn et al. |
| 5,144,962 | A | 9/1992 | Counts et al. |
| 5,146,934 | A | 9/1992 | Deevi et al. |
| 5,159,940 | A | 11/1992 | Hayward et al. |
| 5,159,942 | A | 11/1992 | Brinkley et al. |
| 5,179,966 | A | 1/1993 | Losee et al. |
| 5,211,684 | A | 5/1993 | Shannon et al. |
| 5,220,930 | A | 6/1993 | Gentry |
| 5,224,498 | A | 7/1993 | Deevi et al. |
| 5,228,460 | A | 7/1993 | Sprinkel, Jr. et al. |
| 5,230,354 | A | 7/1993 | Smith et al. |
| 5,235,992 | A | 8/1993 | Sensabaugh |
| 5,243,999 | A | 9/1993 | Smith |
| 5,246,018 | A | 9/1993 | Deevi et al. |
| 5,249,586 | A | 10/1993 | Morgan et al. |
| 5,261,424 | A | 11/1993 | Sprinkel, Jr. |
| 5,269,327 | A | 12/1993 | Counts et al. |
| 5,285,798 | A | 2/1994 | Banerjee et al. |
| 5,293,883 | A | 3/1994 | Edwards |
| 5,301,694 | A | 4/1994 | Raymond |
| 5,303,720 | A | 4/1994 | Banerjee et al. |
| 5,318,050 | A | 6/1994 | Gonzalez-Parra et al. |
| 5,322,075 | A | 6/1994 | Deevi et al. |
| 5,322,076 | A | 6/1994 | Brinkley et al. |
| 5,339,838 | A | 8/1994 | Young et al. |
| 5,345,951 | A | 9/1994 | Serrano et al. |
| 5,353,813 | A | 10/1994 | Deevi et al. |
| 5,357,984 | A | 10/1994 | Farrier et al. |
| 5,360,023 | A | 11/1994 | Blakley et al. |
| 5,369,723 | A | 11/1994 | Counts et al. |
| 5,372,148 | A | 12/1994 | McCafferty et al. |
| 5,377,698 | A | 1/1995 | Litzinger et al. |
| 5,388,574 | A | 2/1995 | Ingebrethsen et al. |
| 5,388,594 | A | 2/1995 | Counts et al. |
| 5,408,574 | A | 4/1995 | Deevi et al. |
| 5,435,325 | A | 7/1995 | Clapp et al. |
| 5,445,169 | A | 8/1995 | Brinkley et al. |
| 5,468,266 | A | 11/1995 | Bensalem et al. |
| 5,468,936 | A | 11/1995 | Deevi et al. |
| 5,479,948 | A | 1/1996 | Counts et al. |
| 5,498,850 | A | 3/1996 | Das |
| 5,498,855 | A | 3/1996 | Deevi et al. |
| 5,499,636 | A | 3/1996 | Baggett, Jr. et al. |
| 5,501,237 | A | 3/1996 | Young et al. |
| 5,505,214 | A | 4/1996 | Collins et al. |
| 5,515,842 | A | 5/1996 | Ramseyer et al. |
| 5,530,225 | A | 6/1996 | Hajaligol |
| 5,551,450 | A | 9/1996 | Hemsley |
| 5,551,451 | A | 9/1996 | Riggs et al. |
| 5,564,442 | A | 10/1996 | MacDonald et al. |
| 5,573,692 | A | 11/1996 | Das et al. |
| 5,591,368 | A | 1/1997 | Fleischhauer et al. |

(56) References Cited

U.S. PATENT DOCUMENTS

| | | | |
|---|---|---|---|
| 5,593,792 | A | 1/1997 | Farrier et al. |
| 5,595,577 | A | 1/1997 | Bensalem et al. |
| 5,596,706 | A | 1/1997 | Sikk et al. |
| 5,611,360 | A | 3/1997 | Tang |
| 5,613,504 | A | 3/1997 | Collins et al. |
| 5,613,505 | A | 3/1997 | Campbell et al. |
| 5,649,552 | A | 7/1997 | Cho et al. |
| 5,649,554 | A | 7/1997 | Sprinkel et al. |
| 5,659,656 | A | 8/1997 | Das |
| 5,665,262 | A | 9/1997 | Hajaligol et al. |
| 5,666,976 | A | 9/1997 | Adams et al. |
| 5,666,977 | A | 9/1997 | Higgins et al. |
| 5,666,978 | A | 9/1997 | Counts et al. |
| 5,687,746 | A | 11/1997 | Rose et al. |
| 5,692,525 | A | 12/1997 | Counts et al. |
| 5,692,526 | A | 12/1997 | Adams et al. |
| 5,708,258 | A | 1/1998 | Counts et al. |
| 5,711,320 | A | 1/1998 | Martin |
| 5,726,421 | A | 3/1998 | Fleischhauer et al. |
| 5,727,571 | A | 3/1998 | Meiring et al. |
| 5,730,158 | A | 3/1998 | Collins et al. |
| 5,743,251 | A | 4/1998 | Howell et al. |
| 5,750,964 | A | 5/1998 | Counts et al. |
| 5,799,663 | A | 9/1998 | Gross et al. |
| 5,816,263 | A | 10/1998 | Counts et al. |
| 5,819,756 | A | 10/1998 | Mielordt |
| 5,829,453 | A | 11/1998 | White et al. |
| 5,865,185 | A | 2/1999 | Collins et al. |
| 5,865,186 | A | 2/1999 | Volsey, II |
| 5,878,752 | A | 3/1999 | Adams et al. |
| 5,880,439 | A | 3/1999 | Deevi et al. |
| 5,894,841 | A | 4/1999 | Voges |
| 5,915,387 | A | 7/1999 | Baggett, Jr. et al. |
| 5,934,289 | A | 8/1999 | Watkins et al. |
| 5,954,979 | A | 9/1999 | Counts et al. |
| 5,967,148 | A | 10/1999 | Harris et al. |
| 6,026,820 | A | 2/2000 | Baggett, Jr. et al. |
| 6,033,623 | A | 3/2000 | Deevi et al. |
| 6,040,560 | A | 3/2000 | Fleischhauer et al. |
| 6,053,176 | A | 4/2000 | Adams et al. |
| 6,089,857 | A | 7/2000 | Matsuura et al. |
| 6,095,153 | A | 8/2000 | Kessler et al. |
| 6,116,247 | A | 9/2000 | Banyasz et al. |
| 6,119,700 | A | 9/2000 | Fleischhauer et al. |
| 6,125,853 | A | 10/2000 | Susa et al. |
| 6,125,855 | A | 10/2000 | Nevett et al. |
| 6,125,866 | A | 10/2000 | Nichols et al. |
| 6,155,268 | A | 12/2000 | Takeuchi |
| 6,164,287 | A | 12/2000 | White |
| 6,182,670 | B1 | 2/2001 | White |
| 6,196,218 | B1 | 3/2001 | Voges |
| 6,196,219 | B1 | 3/2001 | Hess et al. |
| 6,216,706 | B1 | 4/2001 | Kumar et al. |
| 6,289,898 | B1 | 9/2001 | Fournier et al. |
| 6,349,729 | B1 | 2/2002 | Pham |
| 6,357,671 | B1 | 3/2002 | Cewers |
| 6,418,938 | B1 | 7/2002 | Fleischhauer et al. |
| 6,446,426 | B1 | 8/2002 | Sweeney et al. |
| 6,532,965 | B1 | 3/2003 | Abhulimen et al. |
| 6,598,607 | B2 | 7/2003 | Adiga et al. |
| 6,601,776 | B1 | 8/2003 | Oljaca et al. |
| 6,615,840 | B1 | 9/2003 | Fournier et al. |
| 6,688,313 | B2 | 2/2004 | Wrenn et al. |
| 6,701,936 | B2 | 3/2004 | Shafer et al. |
| 6,715,494 | B1 | 4/2004 | McCoy |
| 6,730,832 | B1 | 5/2004 | Dominguez et al. |
| 6,772,756 | B2 | 8/2004 | Shayan |
| 6,803,545 | B2 | 10/2004 | Blake et al. |
| 6,803,550 | B2 | 10/2004 | Sharpe et al. |
| 6,810,883 | B2 | 11/2004 | Felter et al. |
| 6,854,461 | B2 | 2/2005 | Nichols |
| 6,854,470 | B1 | 2/2005 | Pu |
| 6,994,096 | B2 | 2/2006 | Rostami et al. |
| 7,011,096 | B2 | 3/2006 | Li et al. |
| 7,017,585 | B2 | 3/2006 | Li et al. |
| 7,025,066 | B2 | 4/2006 | Lawson et al. |
| 7,117,867 | B2 | 10/2006 | Cox et al. |
| 7,163,015 | B2 | 1/2007 | Moffitt |
| 7,173,322 | B2 | 2/2007 | Sakata et al. |
| 7,185,659 | B2 | 3/2007 | Sharpe et al. |
| 7,234,470 | B2 | 6/2007 | Yang |
| 7,290,549 | B2 | 11/2007 | Banerjee et al. |
| 7,293,565 | B2 | 11/2007 | Griffin et al. |
| 7,392,809 | B2 | 7/2008 | Larson et al. |
| 7,513,253 | B2 | 4/2009 | Kobayashi et al. |
| 7,594,424 | B2 | 9/2009 | Fazekas |
| 7,647,932 | B2 | 1/2010 | Cantrell et al. |
| 7,690,385 | B2 | 4/2010 | Moffitt |
| 7,692,123 | B2 | 4/2010 | Baba et al. |
| 7,726,320 | B2 | 6/2010 | Robinson et al. |
| 7,775,459 | B2 | 8/2010 | Martens, III et al. |
| 7,810,505 | B2 | 10/2010 | Yang |
| 7,832,410 | B2 | 11/2010 | Hon |
| 7,845,359 | B2 | 12/2010 | Montaser |
| 7,878,209 | B2 | 2/2011 | Newbery et al. |
| 7,896,006 | B2 | 3/2011 | Hamano et al. |
| 8,066,010 | B2 | 11/2011 | Newbery et al. |
| 8,079,371 | B2 | 12/2011 | Robinson et al. |
| 8,127,772 | B2 | 3/2012 | Montaser |
| 8,156,944 | B2 | 4/2012 | Han |
| 8,314,591 | B2 | 11/2012 | Terry et al. |
| 8,365,742 | B2 | 2/2013 | Hon |
| 8,375,957 | B2 | 2/2013 | Hon |
| 8,393,331 | B2 | 3/2013 | Hon |
| 8,402,976 | B2 | 3/2013 | Fernando et al. |
| 8,499,766 | B1 | 8/2013 | Newton |
| 8,528,569 | B1 | 9/2013 | Newton |
| 8,550,069 | B2 | 10/2013 | Alelov |
| 8,851,081 | B2 | 10/2014 | Fernando et al. |
| 10,405,579 | B2 * | 9/2019 | Collett ...................... B65B 3/14 |
| 2002/0146242 | A1 | 10/2002 | Vieira |
| 2003/0131859 | A1 | 7/2003 | Li et al. |
| 2003/0226837 | A1 | 12/2003 | Blake et al. |
| 2004/0020500 | A1 | 2/2004 | Wrenn et al. |
| 2004/0118401 | A1 | 6/2004 | Smith et al. |
| 2004/0129280 | A1 | 7/2004 | Woodson et al. |
| 2004/0200488 | A1 | 10/2004 | Fetter et al. |
| 2004/0226568 | A1 | 11/2004 | Takeuchi et al. |
| 2004/0255965 | A1 | 12/2004 | Perfetti et al. |
| 2005/0016549 | A1 | 1/2005 | Banerjee et al. |
| 2005/0016550 | A1 | 1/2005 | Katase |
| 2005/0066986 | A1 | 3/2005 | Nestor et al. |
| 2005/0172976 | A1 | 8/2005 | Newman et al. |
| 2005/0274390 | A1 | 12/2005 | Banerjee et al. |
| 2006/0016453 | A1 | 1/2006 | Kim |
| 2006/0070633 | A1 | 4/2006 | Rostami et al. |
| 2006/0162733 | A1 | 7/2006 | McGrath et al. |
| 2006/0185687 | A1 | 8/2006 | Hearn et al. |
| 2006/0196518 | A1 | 9/2006 | Hon |
| 2007/0074734 | A1 | 4/2007 | Braunshteyn et al. |
| 2007/0102013 | A1 | 5/2007 | Adams et al. |
| 2007/0131708 | A1 | 6/2007 | Poole et al. |
| 2007/0215167 | A1 | 9/2007 | Crooks et al. |
| 2007/0283972 | A1 | 12/2007 | Monsees et al. |
| 2008/0085103 | A1 | 4/2008 | Beland et al. |
| 2008/0092912 | A1 | 4/2008 | Robinson et al. |
| 2008/0149118 | A1 | 6/2008 | Oglesby et al. |
| 2008/0245377 | A1 | 10/2008 | Marshall et al. |
| 2008/0257367 | A1 | 10/2008 | Paterno et al. |
| 2008/0276947 | A1 | 11/2008 | Martzel |
| 2008/0302374 | A1 | 12/2008 | Wengert et al. |
| 2009/0065010 | A1 | 3/2009 | Shands |
| 2009/0095311 | A1 | 4/2009 | Hon |
| 2009/0095312 | A1 | 4/2009 | Herbrich et al. |
| 2009/0126745 | A1 | 5/2009 | Hon |
| 2009/0188490 | A1 | 7/2009 | Hon |
| 2009/0230117 | A1 | 9/2009 | Fernando et al. |
| 2009/0260641 | A1 | 10/2009 | Monsees et al. |
| 2009/0260642 | A1 | 10/2009 | Monsees et al. |
| 2009/0272379 | A1 | 11/2009 | Thorens et al. |
| 2009/0283103 | A1 | 11/2009 | Nielsen et al. |
| 2009/0293892 | A1 | 12/2009 | Williams et al. |
| 2009/0320863 | A1 | 12/2009 | Fernando et al. |
| 2009/0324206 | A1 | 12/2009 | Young et al. |

(56) References Cited

U.S. PATENT DOCUMENTS

| | | | |
|---|---|---|---|
| 2010/0006113 | A1 | 1/2010 | Urtsev et al. |
| 2010/0024834 | A1 | 2/2010 | Oglesby et al. |
| 2010/0043809 | A1 | 2/2010 | Magnon |
| 2010/0059070 | A1 | 3/2010 | Potter et al. |
| 2010/0059073 | A1 | 3/2010 | Hoffmann et al. |
| 2010/0065075 | A1 | 3/2010 | Banerjee et al. |
| 2010/0083959 | A1 | 4/2010 | Siller |
| 2010/0163063 | A1 | 7/2010 | Fernando et al. |
| 2010/0200006 | A1 | 8/2010 | Robinson et al. |
| 2010/0229881 | A1 | 9/2010 | Hearn |
| 2010/0242974 | A1 | 9/2010 | Pan |
| 2010/0242976 | A1 | 9/2010 | Katayama et al. |
| 2010/0258139 | A1 | 10/2010 | Onishi et al. |
| 2010/0300467 | A1 | 12/2010 | Kuistilla et al. |
| 2010/0307518 | A1 | 12/2010 | Wang |
| 2010/0313901 | A1 | 12/2010 | Fernando et al. |
| 2011/0005535 | A1 | 1/2011 | Xiu |
| 2011/0011396 | A1 | 1/2011 | Fang |
| 2011/0036363 | A1 | 2/2011 | Urtsev et al. |
| 2011/0036365 | A1 | 2/2011 | Chong et al. |
| 2011/0073121 | A1 | 3/2011 | Levin et al. |
| 2011/0088707 | A1 | 4/2011 | Hajaligol |
| 2011/0094523 | A1 | 4/2011 | Thorens et al. |
| 2011/0120480 | A1 | 5/2011 | Brenneise |
| 2011/0126847 | A1 | 6/2011 | Zuber et al. |
| 2011/0126848 | A1 | 6/2011 | Zuber et al. |
| 2011/0155153 | A1 | 6/2011 | Thorens et al. |
| 2011/0155718 | A1 | 6/2011 | Greim et al. |
| 2011/0162663 | A1 | 7/2011 | Bryman |
| 2011/0168194 | A1 | 7/2011 | Hon |
| 2011/0180082 | A1 | 7/2011 | Banerjee et al. |
| 2011/0265806 | A1 | 11/2011 | Alarcon et al. |
| 2011/0309157 | A1 | 12/2011 | Yang et al. |
| 2012/0042885 | A1 | 2/2012 | Stone et al. |
| 2012/0060853 | A1 | 3/2012 | Robinson et al. |
| 2012/0111347 | A1 | 5/2012 | Hon |
| 2012/0132643 | A1 | 5/2012 | Choi et al. |
| 2012/0227752 | A1 | 9/2012 | Alelov |
| 2012/0231464 | A1 | 9/2012 | Yu et al. |
| 2012/0260927 | A1 | 10/2012 | Liu |
| 2012/0279512 | A1 | 11/2012 | Hon |
| 2012/0318882 | A1 | 12/2012 | Abehasera |
| 2013/0037041 | A1 | 2/2013 | Worm et al. |
| 2013/0056013 | A1 | 3/2013 | Terry et al. |
| 2013/0081625 | A1 | 4/2013 | Rustad et al. |
| 2013/0081642 | A1 | 4/2013 | Safari |
| 2013/0192619 | A1 | 8/2013 | Tucker et al. |
| 2013/0255702 | A1 | 10/2013 | Griffith, Jr. et al. |
| 2013/0306084 | A1 | 11/2013 | Flick |
| 2013/0319439 | A1 | 12/2013 | Gorelick et al. |
| 2013/0340750 | A1 | 12/2013 | Thorens et al. |
| 2013/0340775 | A1 | 12/2013 | Juster et al. |
| 2014/0000638 | A1 | 1/2014 | Sebastian et al. |
| 2014/0060554 | A1 | 3/2014 | Collett et al. |
| 2014/0060555 | A1 | 3/2014 | Chang et al. |
| 2014/0096781 | A1 | 4/2014 | Sears et al. |
| 2014/0096782 | A1 | 4/2014 | Ampolini et al. |
| 2014/0109921 | A1 | 4/2014 | Chen |
| 2014/0157583 | A1 | 6/2014 | Ward et al. |
| 2014/0209105 | A1 | 7/2014 | Sears et al. |
| 2014/0245705 | A1 | 9/2014 | Lundgren et al. |
| 2014/0253144 | A1 | 9/2014 | Novak et al. |
| 2014/0261408 | A1 | 9/2014 | DePiano et al. |
| 2014/0261486 | A1 | 9/2014 | Potter et al. |
| 2014/0261487 | A1 | 9/2014 | Chapman et al. |
| 2014/0261495 | A1 | 9/2014 | Novak et al. |
| 2014/0270727 | A1 | 9/2014 | Ampolini et al. |
| 2014/0270729 | A1 | 9/2014 | DePiano et al. |
| 2014/0270730 | A1 | 9/2014 | DePiano et al. |
| 2014/0345631 | A1 | 11/2014 | Bowen et al. |
| 2015/0007838 | A1 | 1/2015 | Fernando et al. |
| 2015/0027471 | A1 | 1/2015 | Feldman et al. |
| 2015/0053217 | A1 | 2/2015 | Steingraber et al. |
| 2015/0114409 | A1 | 4/2015 | Brammer et al. |
| 2015/0223522 | A1 | 8/2015 | Ampolini et al. |
| 2015/0289565 | A1 | 10/2015 | Cadieux et al. |
| 2015/0291301 | A1 | 10/2015 | Cadieux et al. |
| 2015/0327598 | A1 | 11/2015 | Xiang |
| 2015/0335070 | A1 | 11/2015 | Sears et al. |
| 2015/0335071 | A1 | 11/2015 | Brinkley et al. |
| 2016/0037826 | A1 | 2/2016 | Hearn et al. |
| 2016/0050974 | A1 | 2/2016 | Galloway et al. |
| 2016/0050975 | A1 | 2/2016 | Worm et al. |
| 2016/0054345 | A1 | 2/2016 | Watson et al. |
| 2016/0073695 | A1 | 3/2016 | Sears et al. |
| 2017/0006921 | A1 | 1/2017 | Lemay et al. |

FOREIGN PATENT DOCUMENTS

| | | |
|---|---|---|
| CA | 2 752 255 | 8/2010 |
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| EP | 2 468 116 | 6/2012 |
| GB | 1444461 | 7/1976 |
| GB | 2469850 | 11/2010 |
| WO | WO 1986/02528 | 5/1986 |
| WO | WO 1997/48293 | 12/1997 |
| WO | WO 02/37990 | 5/2002 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/091593 | 8/2010 |
| WO | WO 2010/118644 | 10/2010 |
| WO | WO 2010/140937 | 12/2010 |
| WO | WO 2011/010334 | 1/2011 |
| WO | WO 2011/081558 | 7/2011 |
| WO | WO 2012/072762 | 6/2012 |
| WO | WO 2012/100523 | 8/2012 |
| WO | WO 2013/089551 | 6/2013 |
| WO | WO 2015/106604 | 7/2015 |
| WO | WO 2015/139186 | 9/2015 |
| WO | WO 2015/172383 | 11/2015 |
| WO | WO 2015/172384 | 11/2015 |
| WO | WO 2015/172387 | 11/2015 |
| WO | WO 2015/172389 | 11/2015 |
| WO | WO 2015/172390 | 11/2015 |
| WO | WO 2015/180145 | 12/2015 |
| WO | WO 2015/196367 | 12/2015 |
| WO | WO 2016/079533 | 5/2016 |
| WO | WO 2016/116755 | 7/2016 |
| WO | WO 2016/187297 | 11/2016 |

OTHER PUBLICATIONS

Freedom Smokeless; Manufacturing: Component Manufacturing, Manufacturing Audits, and Automations Systems and QC; site visited Mar. 27, 2014 (4 pgs.) http://www.freedomsmokeless.com/manufacturing.php.

Freedom Smokeless Video on Vimeo; site visited May 14, 2014 (screenshots—42 pgs.) http://vimeo.com/85109379.

Anonymous; “The Latest Trend in Liquid Filling: E-Cigarette Cartridges and Containers Part 2”; Filamatic of Baltimore, MD; May 24, 2013 (3 pgs); http://www.filamatic.com/blog/409.

(56) References Cited

OTHER PUBLICATIONS

Timothy S. Donahue; The Need for Speed; Vapor Voice; 2015; pp. 30-31; Issue 1.
Mikron G05 "High volume automation solutions for the assembling of products"; 2015; http://www.mikron.com/fileadmin/customer/2_Pdfs/2_Mikron_Automation/Solutions/MikronG05_EN.pdf.
Mikron Ecoline™ "Solutions for the assembling of products"; 2015; http://www.mikron.com/fileadmin/customer/2_Pdfs/2_Mikron_Automation/Solutions/Mikron_Ecoline_EN.pdf.
ATC Automation; Automation tool company—custom assembly automation and test systems; 2016; http://automationtool.com/.
Partial Search Report dated Jul. 12, 2017 for International Application No. PCT/IB2017/052454.
International Search, PCT/IB2017/052454, dated Oct. 9, 2017.

* cited by examiner

1302 — INSERT A CARTRIDGE FOR AN AEROSOL DELIVERY DEVICE ALONG AN AXIS INTO A RECEPTACLE OF A TEST FIXTURE, THE CARTRIDGE COMPRISING A PLURALITY OF TERMINALS AND THE RECEPTACLE COMPRISING A PLURALITY OF ELECTRICAL CONTACTS CONFIGURED TO ENGAGE A RESPECTIVE ONE OF THE TERMINALS

1304 — ALLOW MOVEMENT OF THE RECEPTACLE IN A PLANE PERPENDICULAR TO THE AXIS ALONG WHICH THE CARTRIDGE IS INSERTED INTO THE RECEPTACLE TO FACILITATE ENGAGEMENT OF THE ELECTRICAL CONTACTS WITH THE TERMINALS OF THE CARTRIDGE

1306 — ELECTRICALLY COMMUNICATE WITH THE CARTRIDGE THROUGH THE TERMINALS AND THE ELECTRICAL CONTACTS

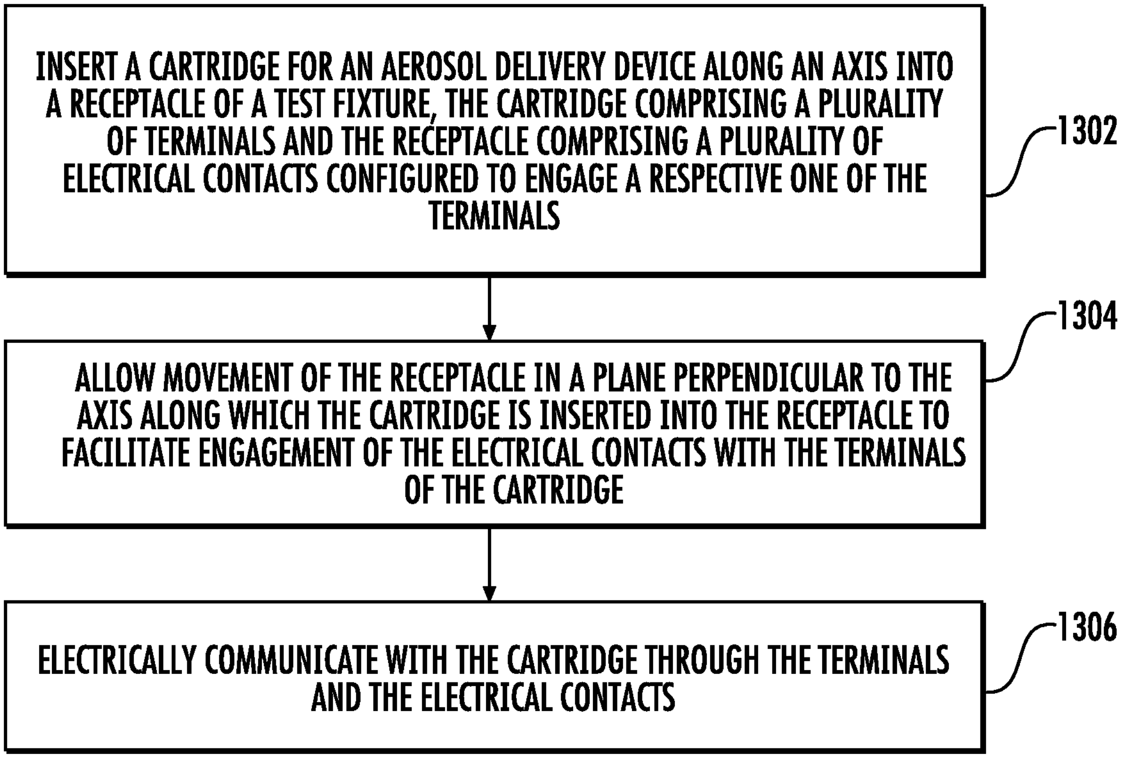

FIG. 52

METHODS FOR ASSEMBLING A CARTRIDGE FOR AN AEROSOL DELIVERY DEVICE, AND ASSOCIATED SYSTEMS AND APPARATUSES

CROSS-REFERENCE TO RELATED APPLICATIONS

This application is a divisional of U.S. application Ser. No. 15/142,502, filed Apr. 29, 2016, which application is hereby incorporated by reference in its entirety in this application.

BACKGROUND

Field of the Disclosure

The present disclosure relates to a cartridge for aerosol delivery devices such as electronic cigarettes, and more particularly to methods for assembling a cartridge for aerosol delivery devices including an atomizer, and associated systems and apparatuses. The atomizer may be configured to heat an aerosol precursor composition, which may be made or derived from tobacco or otherwise incorporate tobacco, to form an inhalable substance for human consumption.

Description of Related Art

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., and U.S. Pat. App. Pub. No. 2015/0059780 to Davis et al., which are incorporated herein by reference in their entireties. See also, for example, the various embodiments of products and heating configurations described in the background sections of U.S. Pat. No. 5,388,594 to Counts et al. and U.S. Pat. No. 8,079,371 to Robinson et al., which are incorporated by reference in their entireties.

However, some aerosol delivery devices (e.g., electronic cigarettes) or portions thereof may be difficult to manufacture. In this regard, for example, the various components of electronic smoking articles may be relatively small and/or fragile. Thus, advances with respect to systems, apparatuses, and methods for manufacturing electronic smoking articles may be desirable.

BRIEF SUMMARY OF THE DISCLOSURE

The present disclosure relates to assembly of cartridges for aerosol delivery devices configured to produce aerosol and which aerosol delivery devices, in some embodiments, may be referred to as electronic cigarettes. In one aspect, a system for assembling a plurality of cartridges for an aerosol delivery device is provided. The system may include a plurality of assembly cells collectively configured to assemble a plurality of cartridge components together. At least a pair of the assembly cells may respectively include one or more assembly carriages respectively configured to engage a plurality of partially-assembled cartridges including one or more of the cartridge components and an assembly track configured to circulate the assembly carriages thereon. The system may further include at least one transfer apparatus including a transfer track positioned between the pair of the assembly cells and configured to individually and sequentially transfer the partially-assembled cartridges between the pair of the assembly cells.

In some embodiments the transfer apparatus may further include one or more transfer carriages configured to respectively receive one of the partially-assembled cartridges and circulate on the transfer track between the pair of the assembly cells. The transfer apparatus may further include a first transfer member configured to disengage the partially-assembled cartridges from the assembly carriages of a first one of the pair of the assembly cells and engage the partially-assembled cartridges with a respective one of the transfer carriages. The transfer apparatus may additionally include a second transfer member configured to disengage the partially-assembled cartridges from the transfer carriages and engage the partially-assembled cartridges with one of the assembly carriages of a second one of the pair of the assembly cells. The cartridge components may include an outer body and one or more components configured for placement within the outer body, and the components may include at least one of a liquid transport element, a reservoir substrate, and a heating element.

In an additional aspect a method for assembling a plurality of cartridges for an aerosol delivery device is provided. The method may include assembling a plurality of cartridge components together at a plurality of assembly cells. Assembling the cartridge components together may include engaging a plurality of partially-assembled cartridges including one or more of the cartridge components with a respective one of one or more assembly carriages and circulating the assembly carriages on an assembly track. The method may additionally include individually and sequentially transporting the partially-assembled cartridges on a transfer track between a pair of the assembly cells.

In some embodiments individually and sequentially transporting the partially-assembled cartridges on the transfer track may include respectively engaging each of the partially-assembled cartridges with one of one or more transfer carriages. Individually and sequentially transporting the partially-assembled cartridges on the transfer track may further include disengaging the partially-assembled cartridges from the assembly carriages of a first one of the pair of the assembly cells and engaging the partially-assembled cartridges with a respective one of the transfer carriages. Individually and sequentially transporting the partially-assembled cartridges on the transfer track may additionally include disengaging the partially-assembled cartridges from the transfer carriages and engaging the partially-assembled cartridges with one of the assembly carriages of a second one of the pair of the assembly cells.

In an additional aspect, an assembly carriage configured to assemble a cartridge for an aerosol delivery device is provided. The assembly carriage may include a first nest configured to receive a partially-assembled cartridge in a first orientation. Further, the assembly carriage may include a second nest configured to receive the partially-assembled cartridge in a second orientation that differs from the first orientation.

In some embodiments the first nest may include a receptacle configured to receive a base of the partially-assembled cartridge such that the partially-assembled cartridge defines a substantially vertical configuration. The second nest may include one or more clamps configured to receive and hold an atomizer in a substantially horizontal configuration. The second nest may include a recess configured to hold the partially-assembled cartridge in a substantially horizontal configuration. The recess of the second nest may be configured to hold the partially-assembled cartridge such that a first heating terminal and a second heating terminal thereof are in contact with a heating element of the atomizer. The clamps may be configured to extend on first and second opposing sides of the partially-assembled cartridge.

In some embodiments the first nest may include a clamp configured to engage a reservoir substrate and a recess configured to receive a partially-assembled cartridge. The recess may be aligned and recessed with respect to the clamp such that the reservoir substrate wraps at least partially around the partially-assembled cartridge during insertion of the partially-assembled cartridge into the recess. The clamp may include a plurality of prongs that extend on first and second opposing sides of the first nest. The first nest may further define first and second openings positioned at the first and second opposing sides of the first nest. The first and second openings may be configured to receive an end effector that clamps the reservoir substrate against the partially-assembled cartridge. The first and second opposing sides of the first nest may be elevated with respect to the recess. The second nest may include a receptacle configured to receive a base of the partially-assembled cartridge such that the partially-assembled cartridge defines a substantially vertical configuration. The recess of the first nest may be configured to hold the partially-assembled cartridge in a substantially horizontal configuration.

In an additional aspect a method for assembling a cartridge for an aerosol delivery device is provided. The method may include receiving a partially-assembled cartridge in a first orientation in a first nest of an assembly carriage. Further, the method may include receiving the partially-assembled cartridge in a second orientation that differs from the first orientation in a second nest of the assembly carriage.

In some embodiments receiving the partially-assembled cartridge in the first orientation in the first nest of the assembly carriage may include receiving a base of the partially-assembled cartridge such that the partially-assembled cartridge defines a substantially vertical configuration. Further, the method may include receiving and holding an atomizer in a substantially horizontal configuration at the second nest. Receiving the partially-assembled configured cartridge in the second orientation in the second nest of the assembly carriage may include receiving the partially-assembled cartridge in a recess configured to hold the partially-assembled cartridge in a substantially horizontal configuration. Receiving the partially-assembled cartridge in the recess may include holding the partially-assembled cartridge such that a first heating terminal and a second heating terminal thereof are in contact with a heating element of the atomizer. Receiving and holding the atomizer in the substantially horizontal configuration at the second nest may include clamping the atomizer on first and second opposing sides of the partially-assembled cartridge.

In some embodiments the method may further include engaging a reservoir substrate with a clamp at the first nest. Receiving the partially-assembled cartridge in the first orientation in the first nest may include inserting the partially-assembled cartridge into a recess. The recess may be aligned and recessed with respect to the clamp such that the reservoir substrate wraps at least partially around the partially-assembled cartridge during insertion of the partially-assembled cartridge into the recess. Engaging the reservoir substrate with the clamp may include engaging the reservoir substrate with a plurality of prongs that extend on first and second opposing sides of the nest. The method may additionally include directing an end effector into first and second openings positioned at the first and second opposing sides of the nest and clamping the reservoir substrate against the partially-assembled cartridge with the end effector. Engaging the prongs with the reservoir substrate may include pressing the reservoir substrate against the first and second opposing sides of the nest. The first and second opposing sides of the nest may be elevated with respect to the recess.

In an additional aspect a system for assembling a plurality of cartridges for an aerosol delivery device is provided. The system may include a folding apparatus including a plurality of posts respectively including a notch defined therein. The folding apparatus may be configured to receive a partially-assembled cartridge therebetween such that first and second ends of a liquid transport element of the partially-assembled cartridge contact the posts at the notches to fold the liquid transport element against a remainder of the partially-assembled cartridge. The folding apparatus may further include an actuator configured to move the posts toward one another to fold the liquid transport element. The system may additionally include a base gripper configured to grip a base of the partially-assembled cartridge while the actuator moves the posts toward one another. Further, the system may include a gripper configured to direct the partially-assembled cartridge through the posts.

In an additional aspect, an aerosol delivery device assembly method is provided. The method may include providing a substantially-continuous input including a plurality of heating elements engaged with a substantially-continuous liquid transport element. Further, the method may include providing a first heating terminal and a second heating terminal. The method may additionally include engaging the first heating terminal and the second heating terminal with one of the heating elements. The method may further include welding the first heating terminal and the second heating terminal to the one of the heating elements. Additionally, the method may include cutting the substantially-continuous input to singulate the one of the heating elements to which the first heating terminal and the second heating terminal are attached and a corresponding liquid transport segment from the substantially-continuous input.

In some embodiments welding the first heating terminal and the second heating terminal to the one of the heating elements may include laser welding the first heating terminal and the second heating terminal to the one of the heating elements with a laser welder by focusing a laser at the first heating terminal and the second heating terminal. The laser welder, the first heating terminal, and the second heating terminal may remain stationary during and between welding the first heating terminal and the second heating terminal to the one of the heating elements. Providing the first heating terminal and the second heating terminal may include providing an assembly including a base and a flow director. The first heating terminal and the second heating terminal may extend through the flow director. Engaging the first heating terminal and the second heating terminal with the one of the heating elements may include rotating a rotary transporter.

In an additional aspect a system for assembling a plurality of cartridges for an aerosol delivery device is provided. The system may include an input feeder configured to dispense a substantially-continuous input including a plurality of heating elements engaged with a substantially-continuous liquid transport element. Further, the system may include an assembly feeder configured to engage a first heating terminal and a second heating terminal with one of the heating elements. The system may additionally include a welder configured to weld the first heating terminal and the second heating terminal to the one of the heating elements. The system may further include a cutter configured to cut the substantially-continuous input to singulate the one of the heating elements to which the first heating terminal and the second heating terminal are attached and a corresponding liquid transport segment from the substantially-continuous input.

In some embodiments the welder may include a laser welder configured to weld the first heating terminal and the second heating terminal to the one of the heating elements by focusing a laser at the first heating terminal and the second heating terminal. The laser welder, the first heating terminal, and the second heating terminal may remain stationary during and between welding the first heating terminal and the second heating terminal to the one of the heating elements. The assembly feeder may be configured to transport an assembly including a base and a flow director. The first heating terminal and the second heating terminal may extend through the flow director. The assembly feeder may include a rotary transporter configured to rotate to transport the assembly such that the first heating terminal and the second heating terminal engage the one of the heating elements.

In an additional aspect an aerosol delivery device assembly method is provided. The method may include grasping an assembly with a plurality of clamps respectively including a first finger and a second finger. The assembly may include a flow director, an atomizer, a first heating terminal, and a second heating terminal, wherein the first heating terminal and the second heating terminal are coupled to the atomizer. The method may further include opening the clamps. Additionally, the method may include positioning a reservoir substrate in contact with the assembly. The method may further include closing the clamps around the assembly such that the substrate wraps at least partially around the assembly.

In some embodiments positioning the reservoir substrate in contact with the assembly may include engaging the substrate with a substrate gripper including one or more protrusions configured to apply a negative pressure thereto. Closing the clamps may include receiving the one or more protrusions in one or more gaps positioned between the clamps. The method may further include retracting the substrate gripper after closing the clamps by retracting the one or more protrusions through the one or more gaps. Additionally, the method may include engaging a cap with the assembly while positioning the reservoir substrate in contact with the assembly. Opening the clamps may include inserting an actuator pin into engagement with the clamps to sequentially open the clamps. Closing the clamps may include retracting the actuator pin to sequentially close the clamps.

In an additional aspect an apparatus configured to assemble an aerosol delivery device is provided. The apparatus may include an assembly gripper including a plurality of clamps respectively including a first finger and a second finger. The clamps may be configured to grasp an assembly including a flow director, an atomizer, a first heating terminal, and a second heating terminal. The first heating terminal and the second heating terminal may be coupled to the atomizer. The apparatus may additionally include a body to which the clamps are hingedly coupled. The body may define at least one access port configured to receive an actuator pin to open the clamps.

In some embodiments the apparatus may further include a substrate gripper configured to engage a reservoir substrate and position the reservoir substrate in contact with the assembly. The substrate gripper may include one or more protrusions configured to apply a negative pressure thereto. The substrate gripper may be configured to release the reservoir substrate after the clamps close and retract the one or more protrusions through one or more gaps positioned between the clamps. The apparatus may further include a cap configured to engage the assembly while positioning the reservoir substrate in contact with the assembly. Additionally, the apparatus may include the actuator pin. Insertion of the actuator pin may be configured to engage and sequentially open the clamps and retraction of the actuator pin may be configured to sequentially close the clamps. Each of the clamps may include at least one spring configured to bias the clamps to a closed configuration.

In a further aspect an ultrasonic welding system for an aerosol delivery device is provided. The ultrasonic welding system may include a welding clamp configured to engage a cartridge comprising a base and an outer body. The welding clamp may include a first cartridge gripper and a second cartridge gripper. The first cartridge gripper and the second cartridge gripper may respectively include a base protrusion and an outer body protrusion. A distance between the outer body protrusion of the first cartridge gripper and the outer body protrusion of the second cartridge gripper may be greater than a dimension of the outer body of the cartridge therebetween when the base protrusion of the first cartridge gripper and the base protrusion of the second cartridge gripper engage the base of the cartridge. Further, the ultrasonic welding system may include an ultrasonic horn configured to engage an end of the outer body of the cartridge opposite from the base while the cartridge is received in the welding clamp to ultrasonically weld the outer body to the base.

In some embodiments the base protrusion of the first cartridge gripper, the base protrusion of the second cartridge gripper, and the outer body gripper of the first cartridge gripper may respectively define a groove configured to receive the cartridge. The outer body protrusion of the second cartridge gripper may define a substantially flat face. The first cartridge gripper and the second cartridge gripper may respectively include one or more intermeshing protrusions. The ultrasonic welding system may further include an assembly gripper that may include a plurality of first fingers and a plurality of second fingers. The first fingers may intermesh with the one or more intermeshing protrusions of the first cartridge gripper and the second fingers may intermesh with the one or more intermeshing protrusions of the second cartridge gripper.

In an additional aspect an aerosol delivery device ultrasonic welding method is provided. The method may include engaging a welding clamp with a cartridge including a base and an outer body by clamping a plurality of base protrusions against the base of the cartridge and positioning a plurality of outer body protrusions adjacent to the outer body. A distance between the outer body protrusions may be greater than a dimension of the cartridge between the outer body protrusions. The method may additionally include engaging an ultrasonic horn with the outer body opposite from the base. Further, the method may include ultrasonically vibrating the ultrasonic horn to weld the outer body to the base. Additionally, the method may include constraining movement of the outer body with the outer body protrusions to maintain alignment of the outer body with respect to the base while ultrasonically vibrating the ultrasonic horn. In some embodiments of the method engaging the welding clamp with the cartridge may include positioning the outer body protrusions out of contact with the outer body prior to ultrasonically vibrating the ultrasonic horn. Further, constraining movement of the outer body with the outer body protrusions may include positioning the outer body between a groove and a substantially flat face of the outer body protrusions.

In a further aspect an aerosol delivery device cartridge filling system is provided. The system may include an assembly carriage including a plurality of receptacles configured to respectively receive a partially-assembled cartridge including a flow director. The receptacles may each include an aperture extending through the assembly carriage. The system may additionally include a filling apparatus configured to dispense an aerosol precursor composition into the cartridge at one or more of the receptacles. Further, the system may include a manifold including a plurality of cooperating outlets configured to align with at least a portion of the receptacles. The system may additionally include an air supply configured to supply a flow of air into the manifold, out of the manifold through the cooperating outlets, into the aperture at each of the receptacles aligned with the cooperating outlets, and through the flow director of the cartridge while the filling apparatus dispenses the aerosol precursor composition.

In some embodiments of the system the manifold is configured to direct the flow of air through each of the receptacles. In another embodiment the system may include one or more additional manifolds. The manifold and the one or more additional manifolds may each be configured to direct the flow of air through a portion of the receptacles such that each receptacle receives the flow of air.

In an additional aspect an aerosol delivery device cartridge filling method is provided. The method may include dispensing an aerosol precursor composition into a partially-assembled cartridge including a flow director. The method may additionally include directing a flow of air through the flow director while dispensing the aerosol precursor composition into the partially-assembled cartridge.

In some embodiments of the method, directing the flow of air through the flow director may include directing the flow of air upwardly through the flow director. Additionally, directing the aerosol precursor composition into the partially-assembled cartridge may include directing the aerosol precursor composition into contact with a reservoir substrate extending at least partially around the flow director. The method may further include positioning the partially-assembled cartridge in an assembly carrier. Directing the flow of air through the flow director may include directing the flow of air through the assembly carrier. Directing the flow of air through the flow director may further include engaging a manifold with the assembly carrier and directing the flow of air from the manifold to the assembly carrier.

In a further aspect a test fixture for an aerosol delivery device cartridge is provided. The test fixture may include a receptacle including a plurality of electrical contacts configured to engage a respective one of a plurality of terminals of a cartridge for an aerosol delivery device. The test fixture may additionally include a plurality of insulators configured to electrically insulate each of the electrical contacts from one another. Further, the test fixture may include a controller configured to electrically communicate with the cartridge through the terminals and the electrical contacts. The test fixture may additionally include a compliant member configured to allow for movement of the receptacle in a plane perpendicular to an axis along which the cartridge is inserted into the receptacle to facilitate engagement of the electrical contacts with the terminals of the cartridge.

In some embodiments of the test fixture, each of the electrical contacts may be fixedly secured to one another. In another embodiment of the test fixture, each of the electrical contacts may be independently moveable with respect to one another in at least one direction.

In an additional aspect an aerosol delivery device test method is provided. The method may include inserting a cartridge for an aerosol delivery device along an axis into a receptacle of a test fixture. The cartridge may include a plurality of terminals and the receptacle may include a plurality of electrical contacts configured to engage a respective one of the terminals. The method may further include allowing movement of the receptacle in a plane perpendicular to the axis along which the cartridge is inserted into the receptacle to facilitate engagement of the electrical contacts with the terminals of the cartridge. Additionally, the method may include electrically communicating with the cartridge through the terminals and the electrical contacts.

In some embodiments of the method, allowing movement of the receptacle may include fixedly securing the electrical contacts to one another such that each of the electrical contacts moves in unison. In another embodiment of the method, allowing movement of the receptacle may include allowing each of the electrical contacts to move independently in at least one direction.

These and other features, aspects, and advantages of the disclosure will be apparent from a reading of the following detailed description together with the accompanying drawings, which are briefly described below.

BRIEF DESCRIPTION OF THE FIGURES

Figure 1:
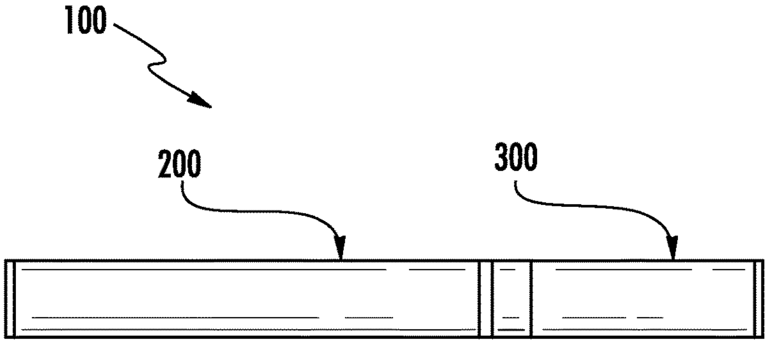
Figure 2:
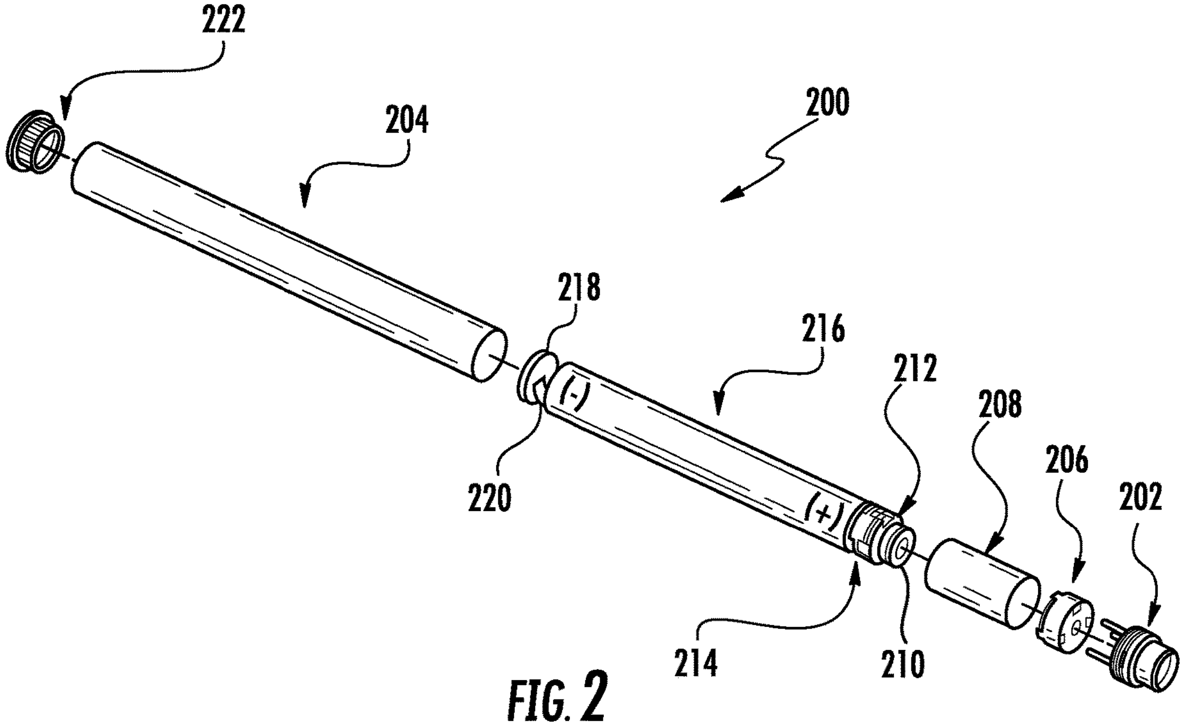
Figure 3:
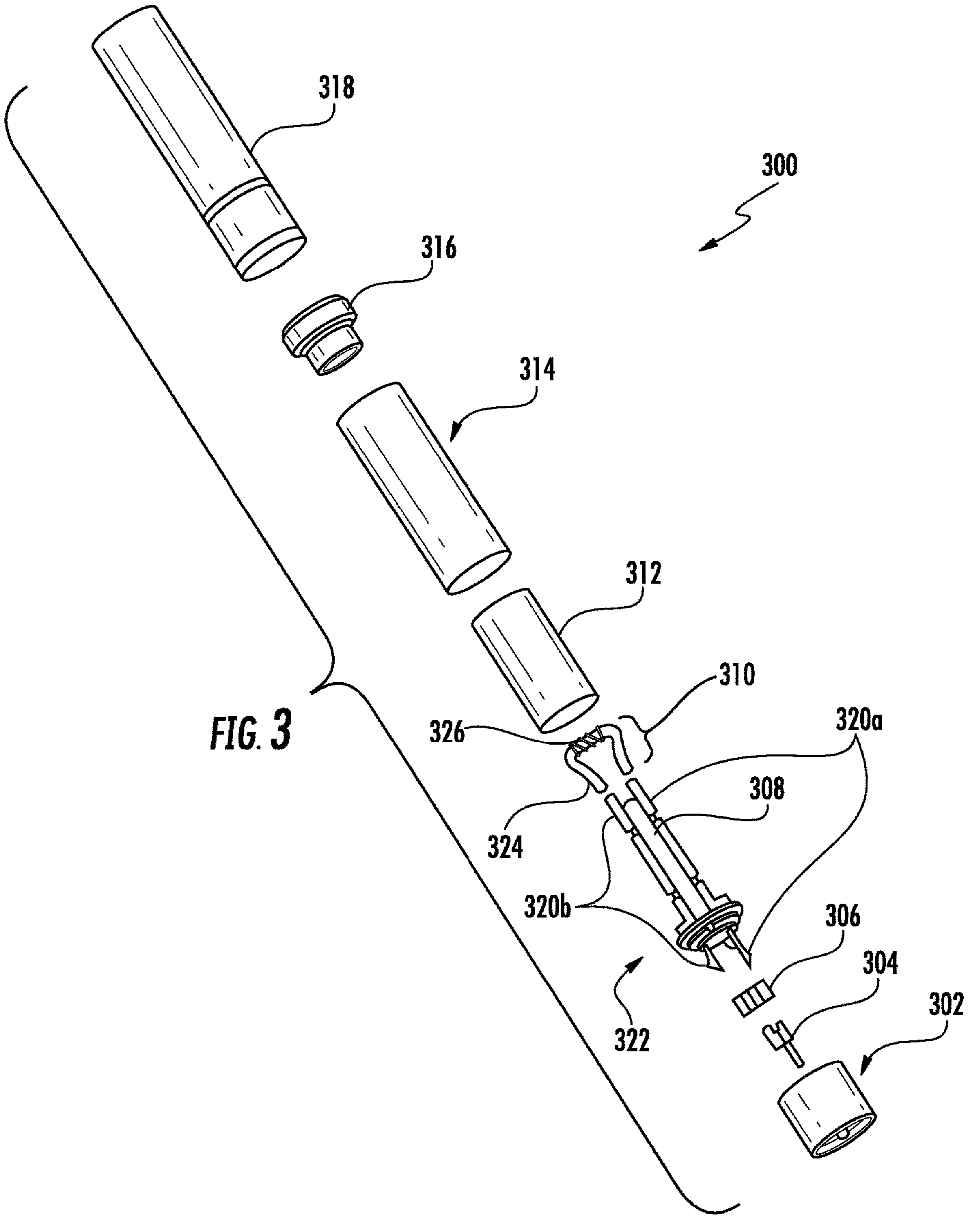
Figure 4:
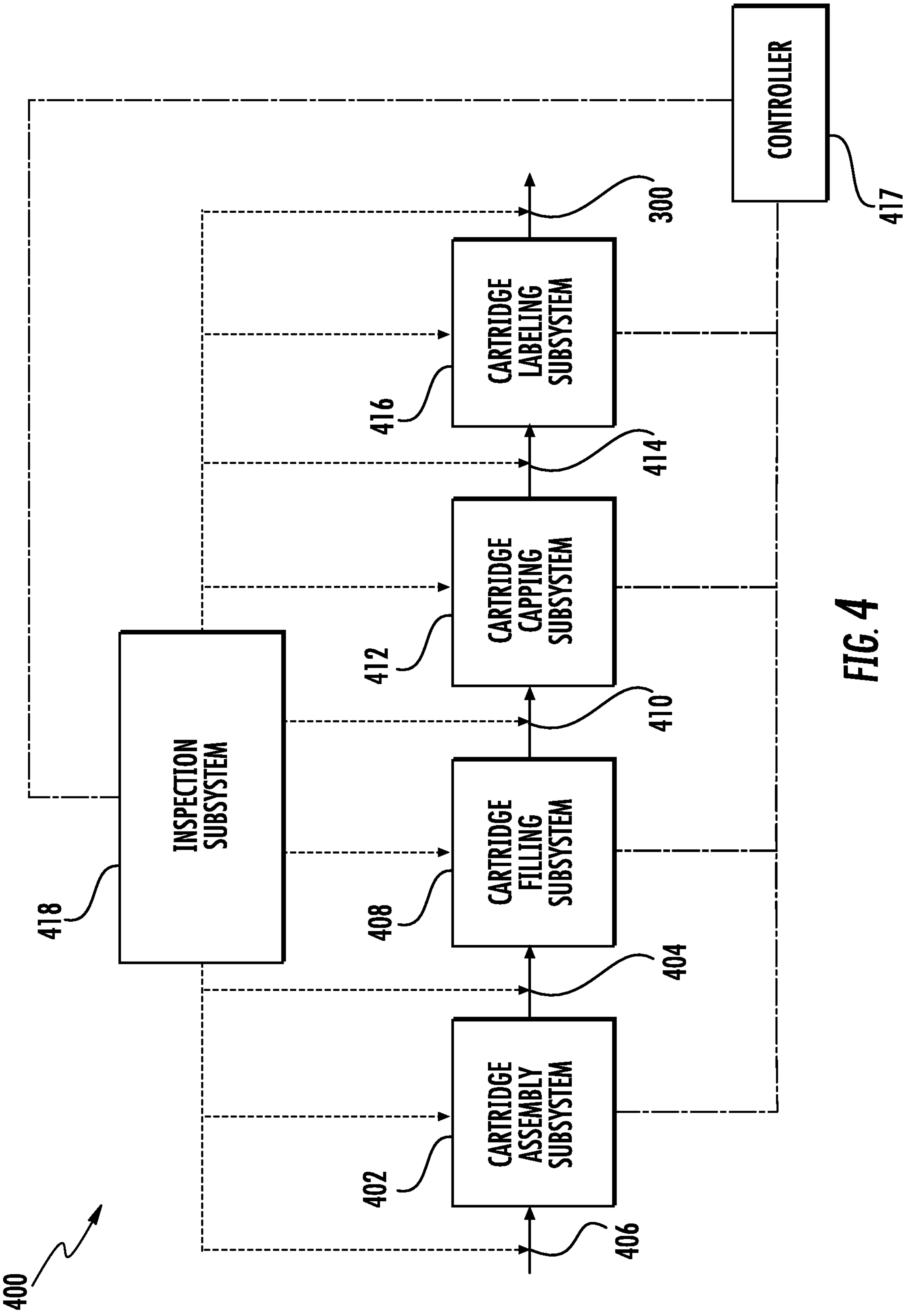
Figure 5:
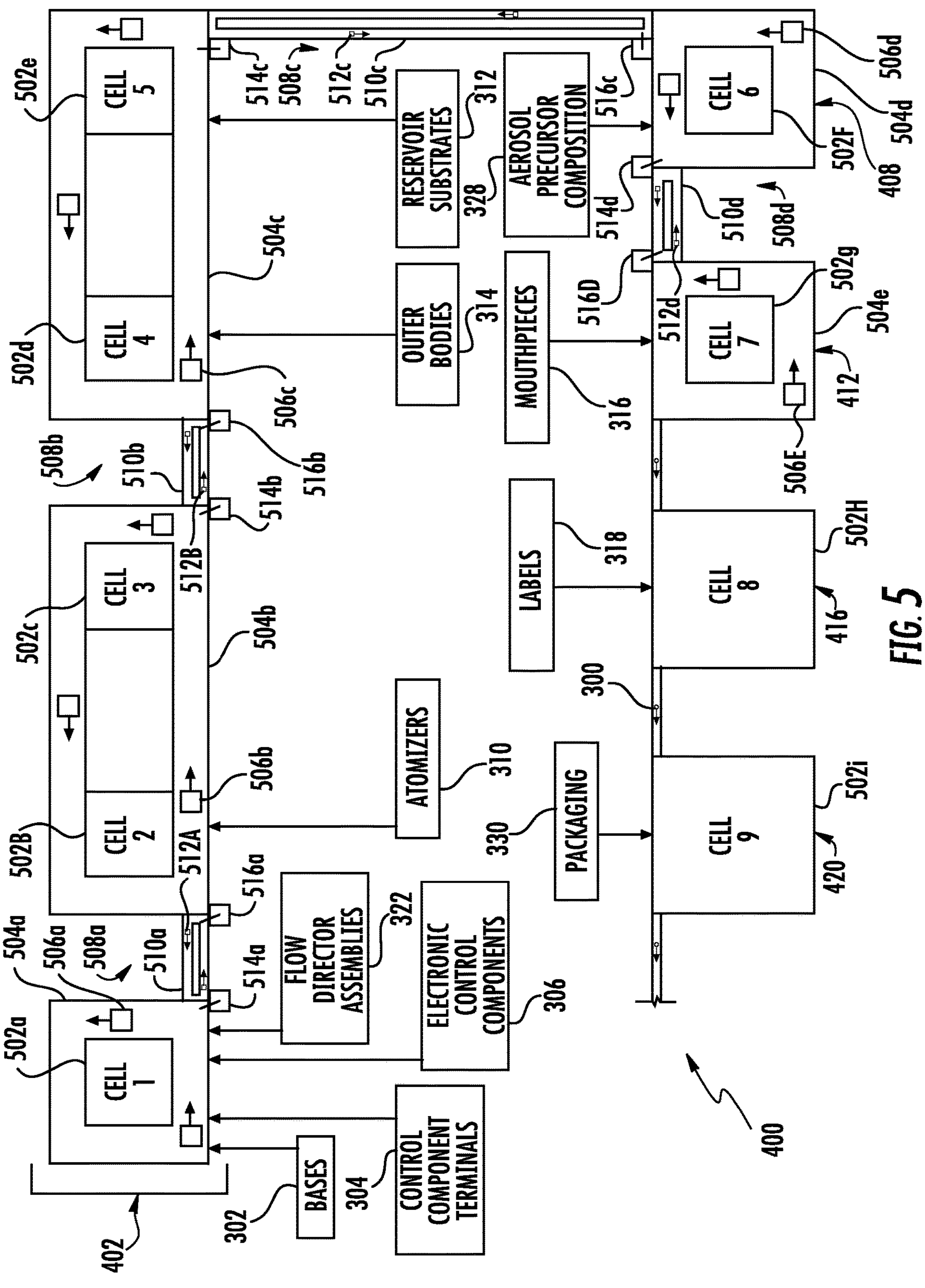
Figure 6:
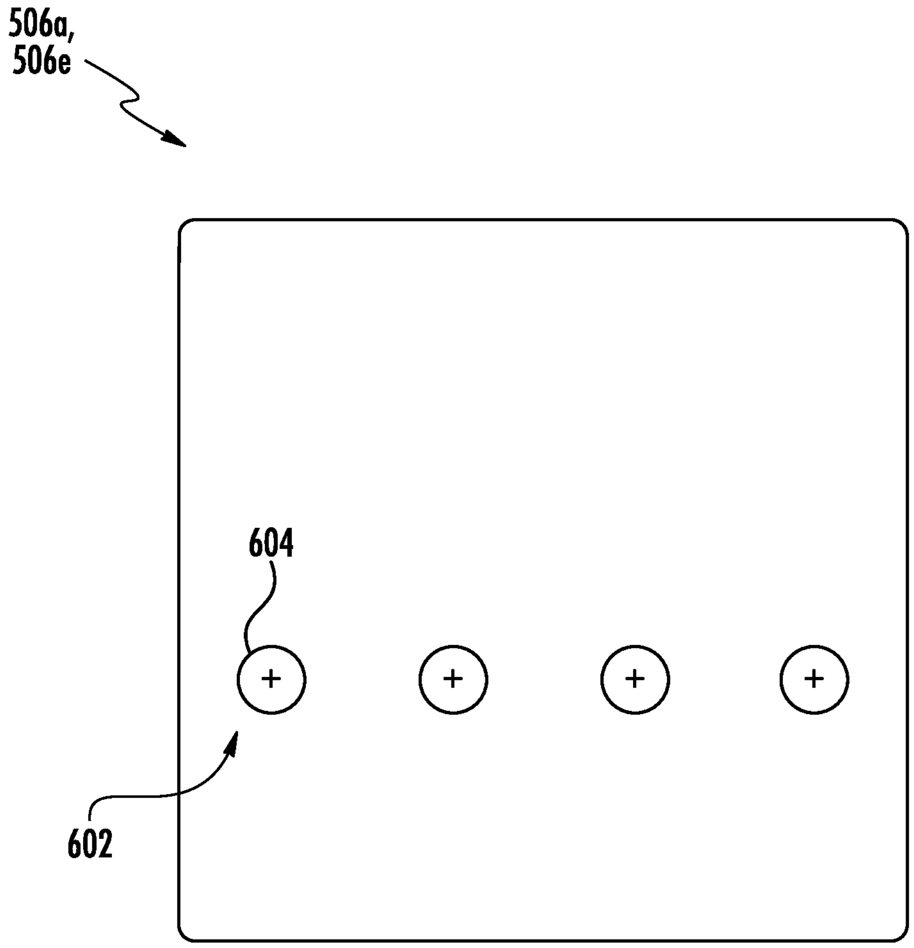
Figure 7:
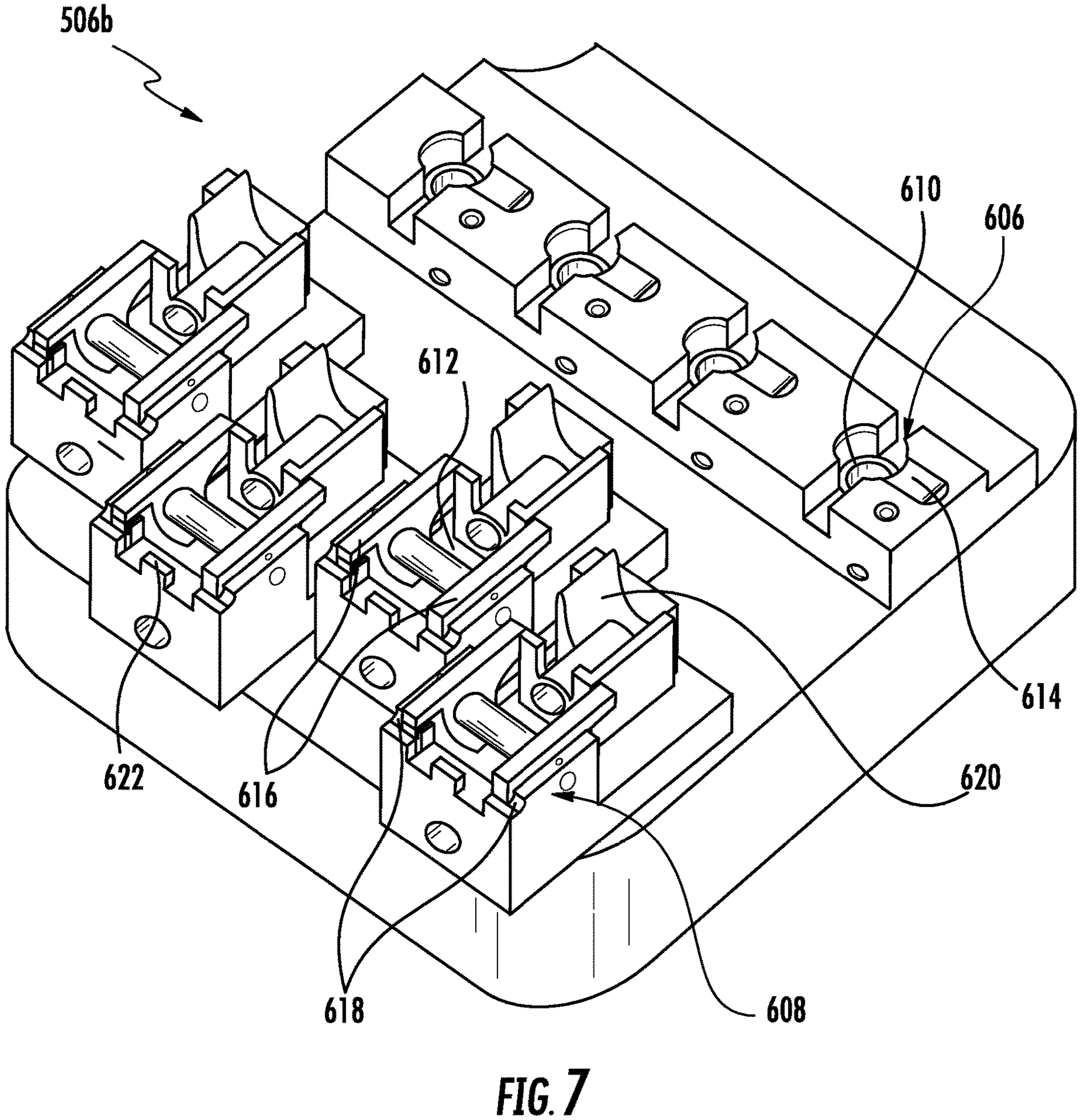
Figure 8:
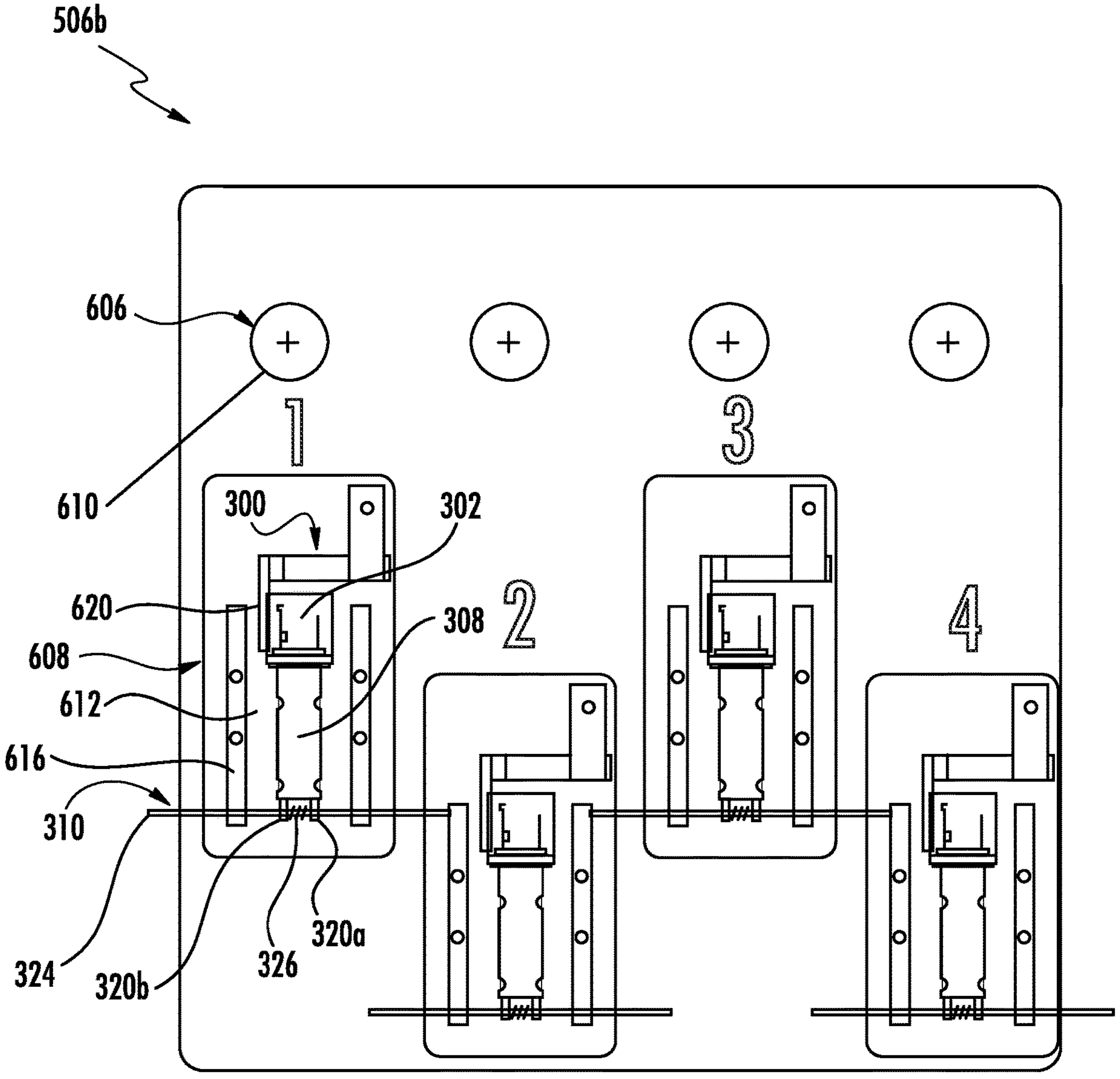
Figure 9:
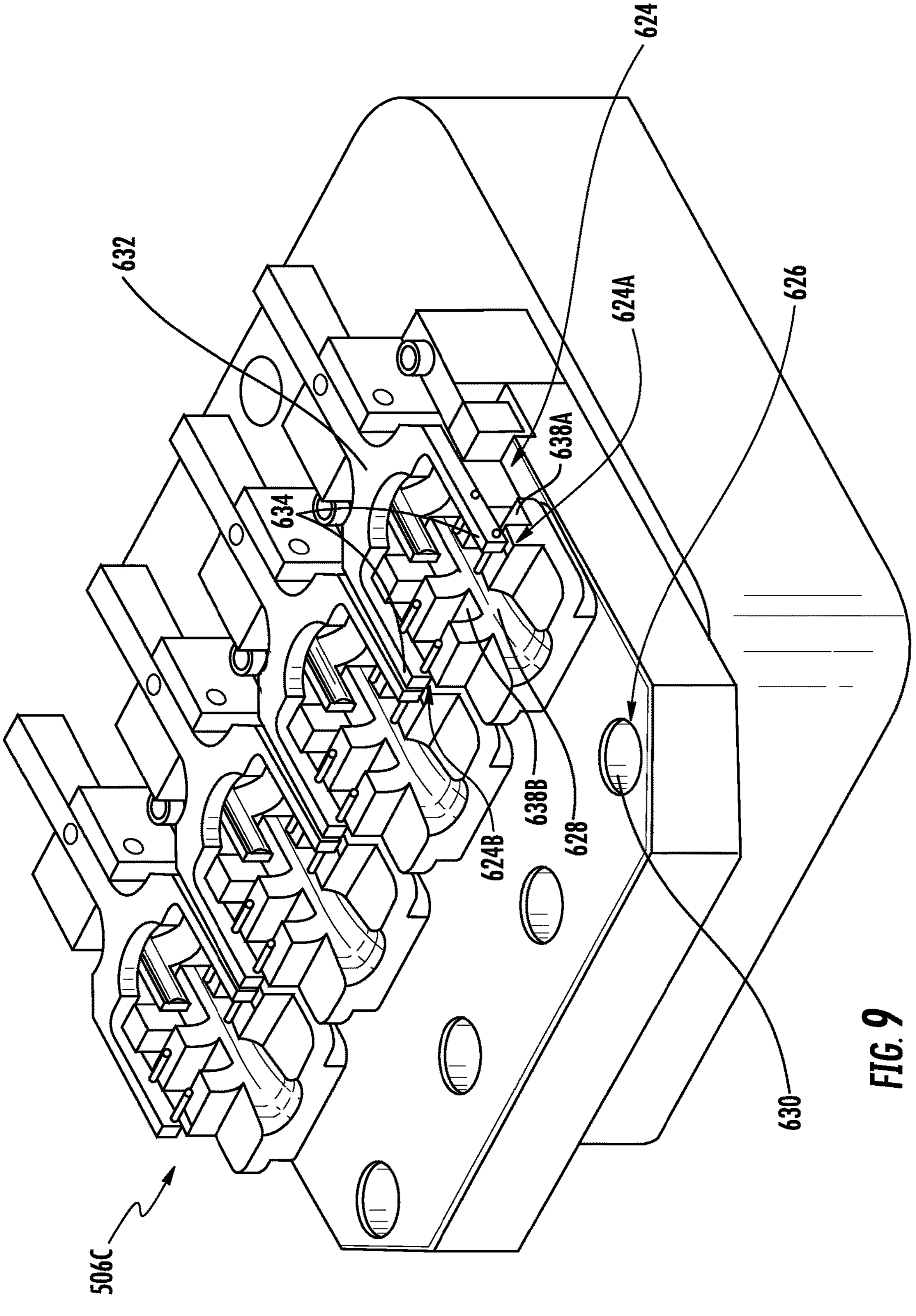
Figure 10:
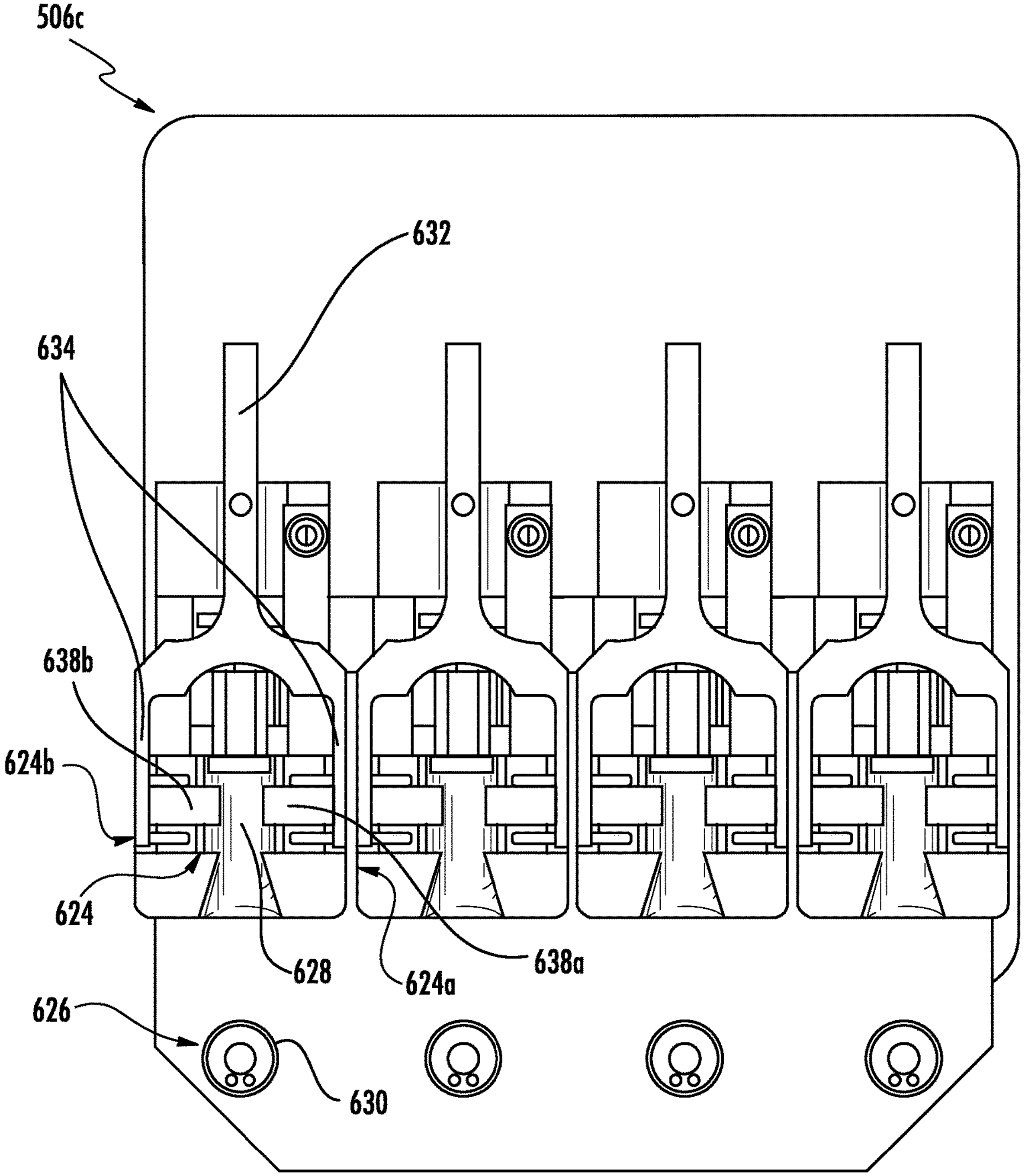
Figure 11:
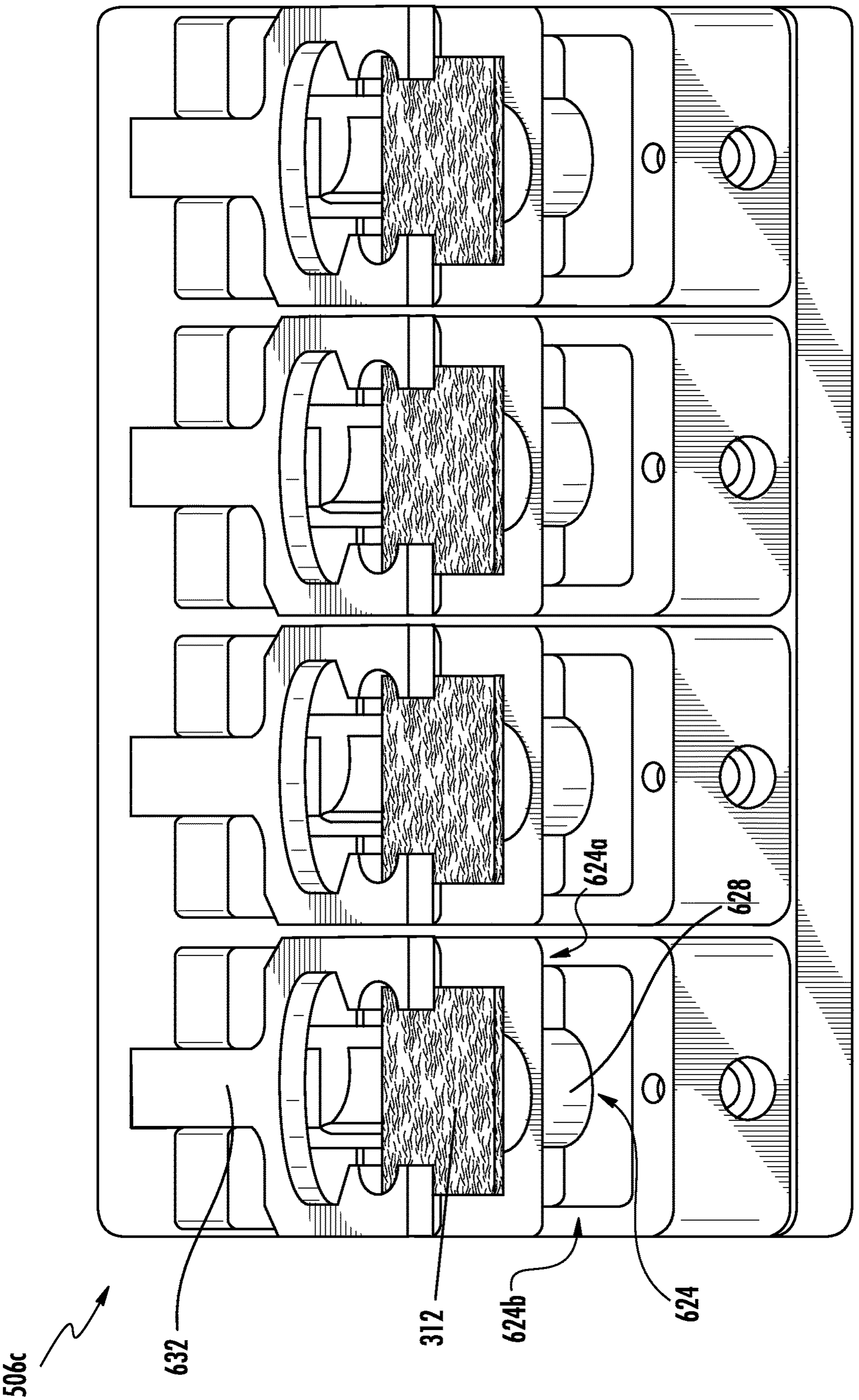
Figure 12:
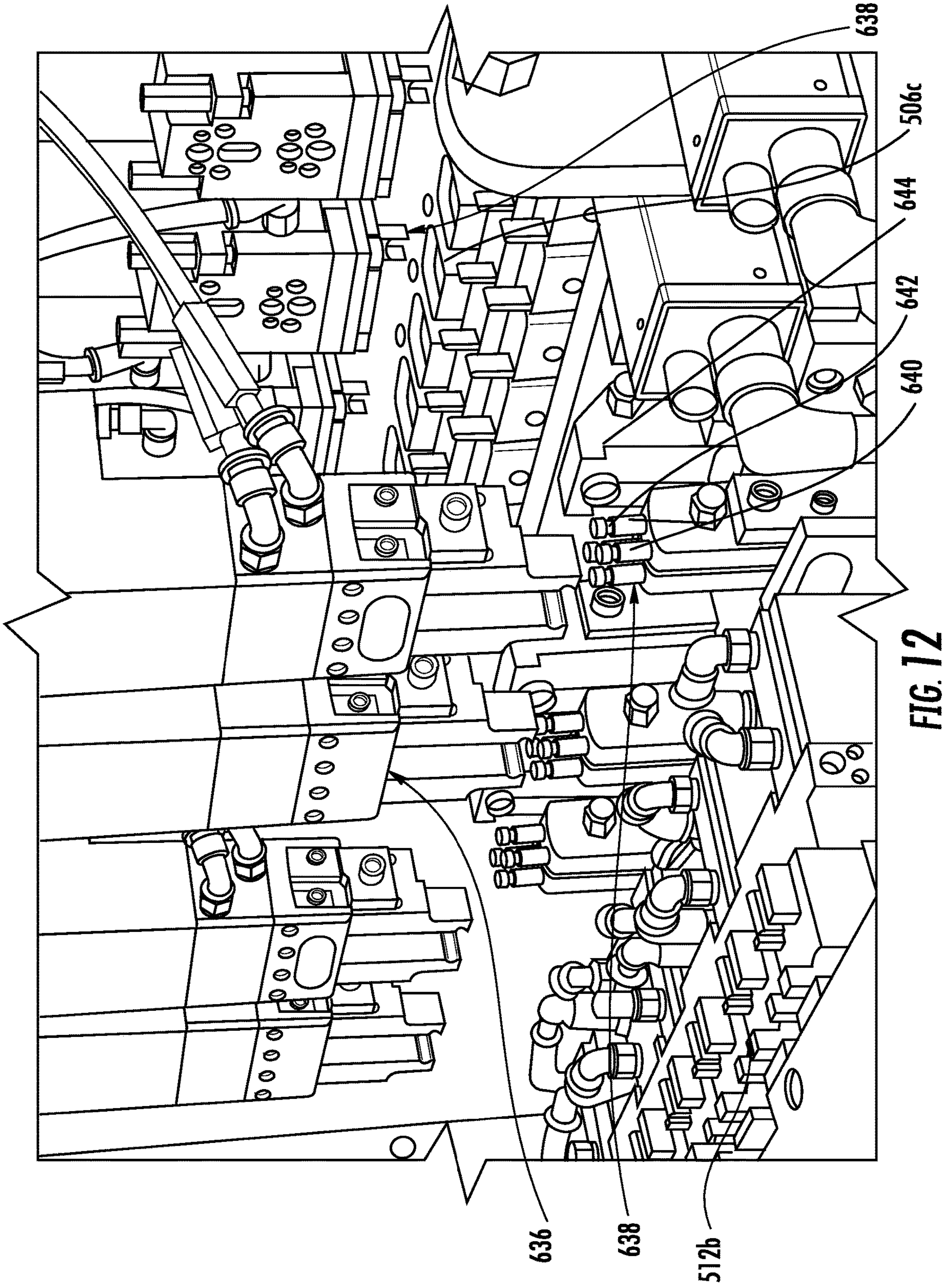
Figure 13:
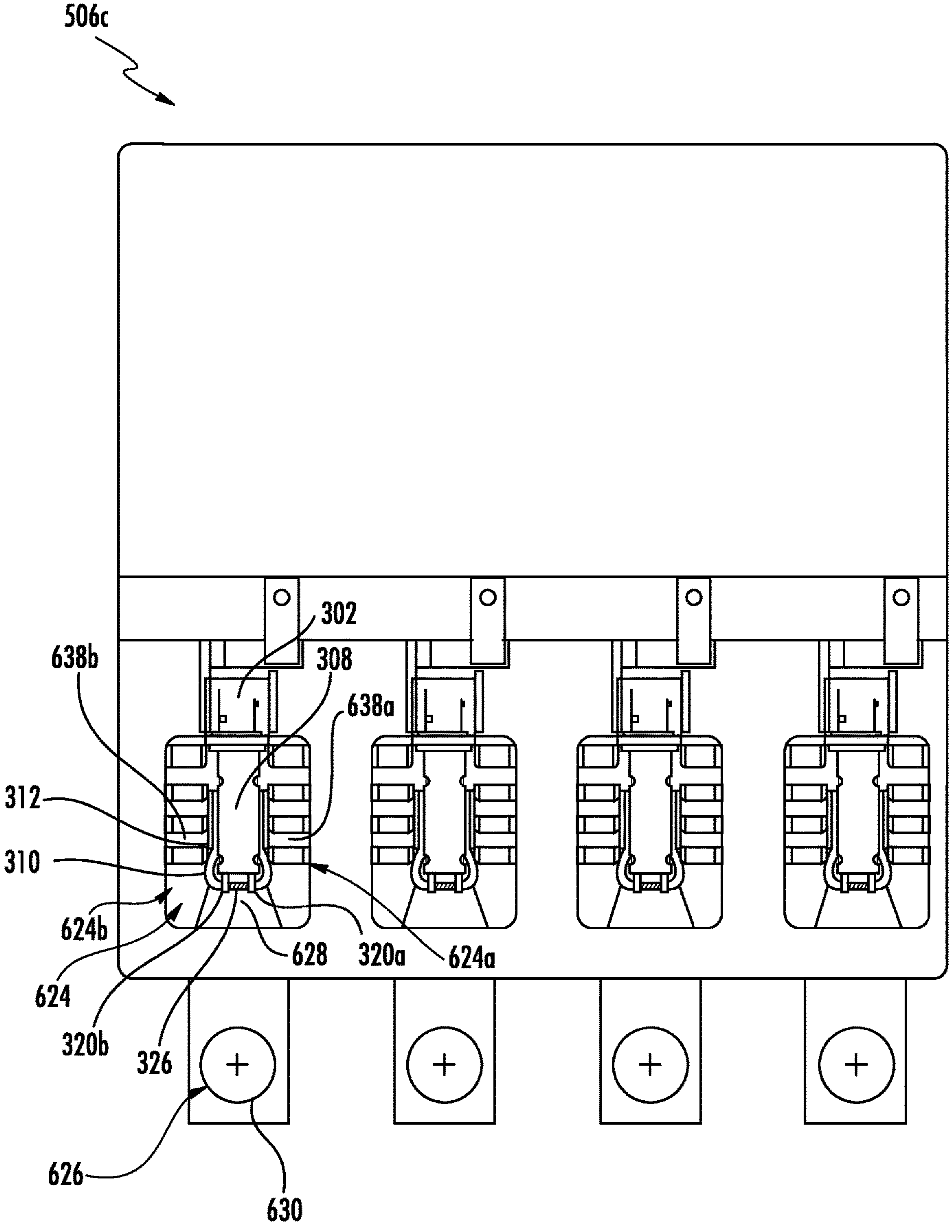
Figure 14:
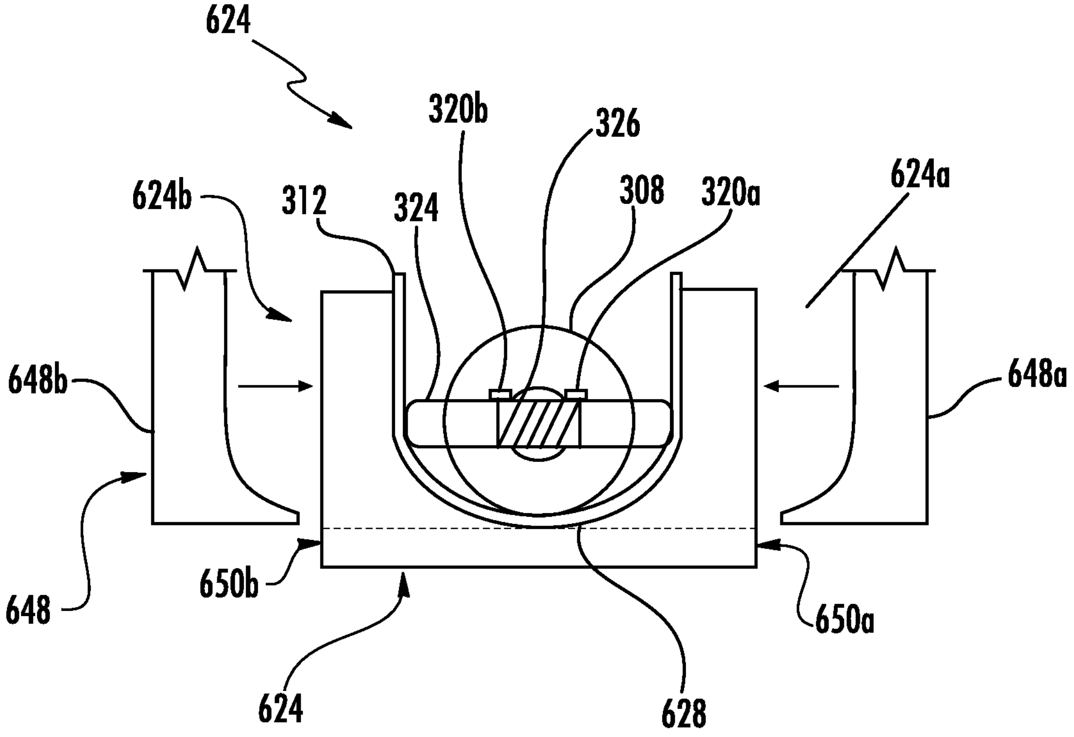
Figure 15:
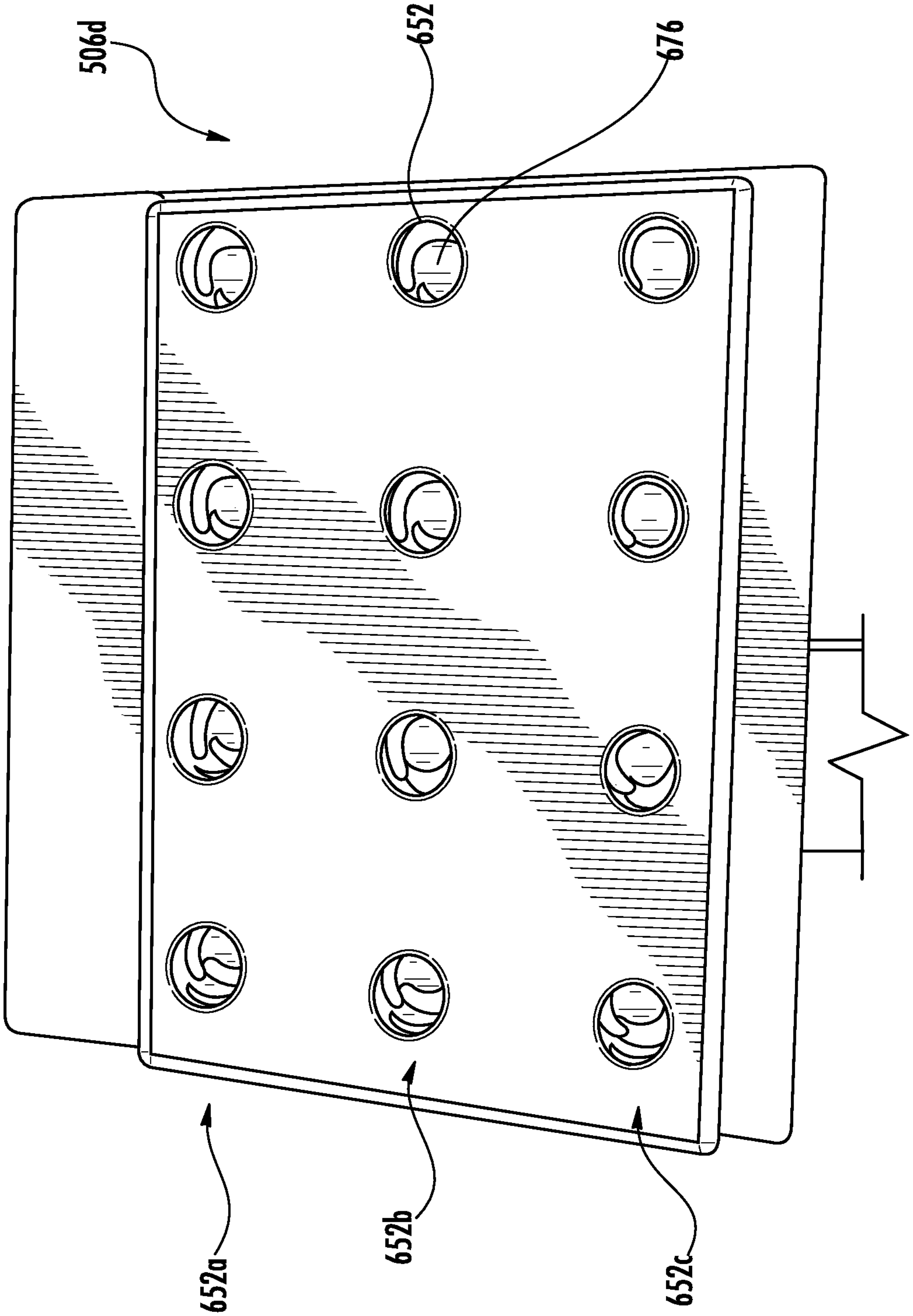
Figure 16:
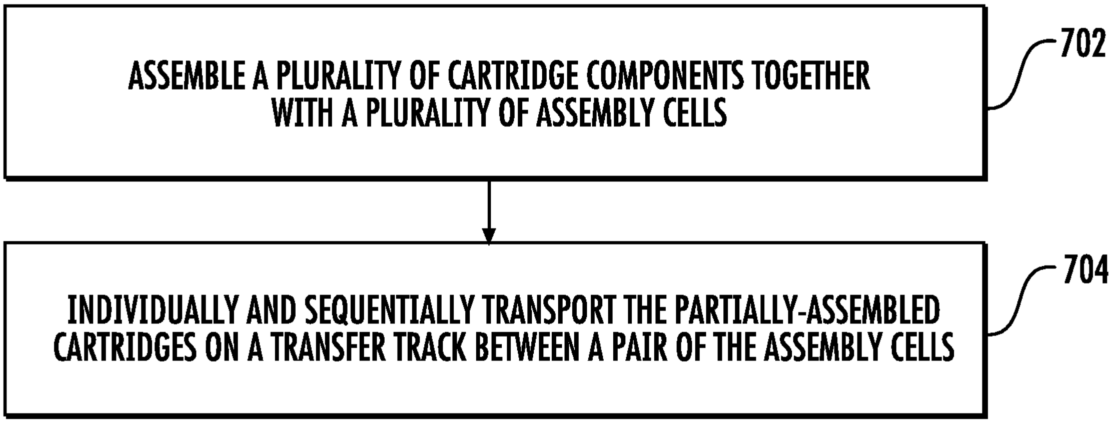
Figure 17:
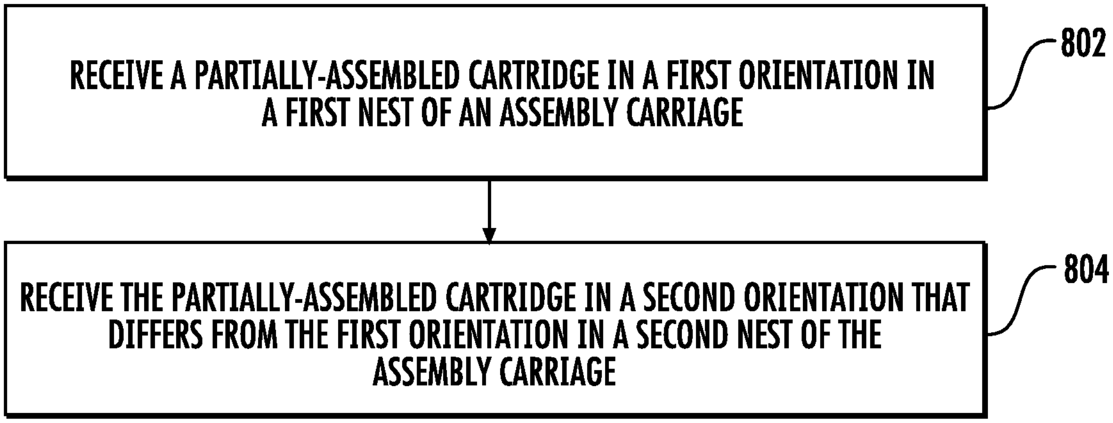
Figure 18:
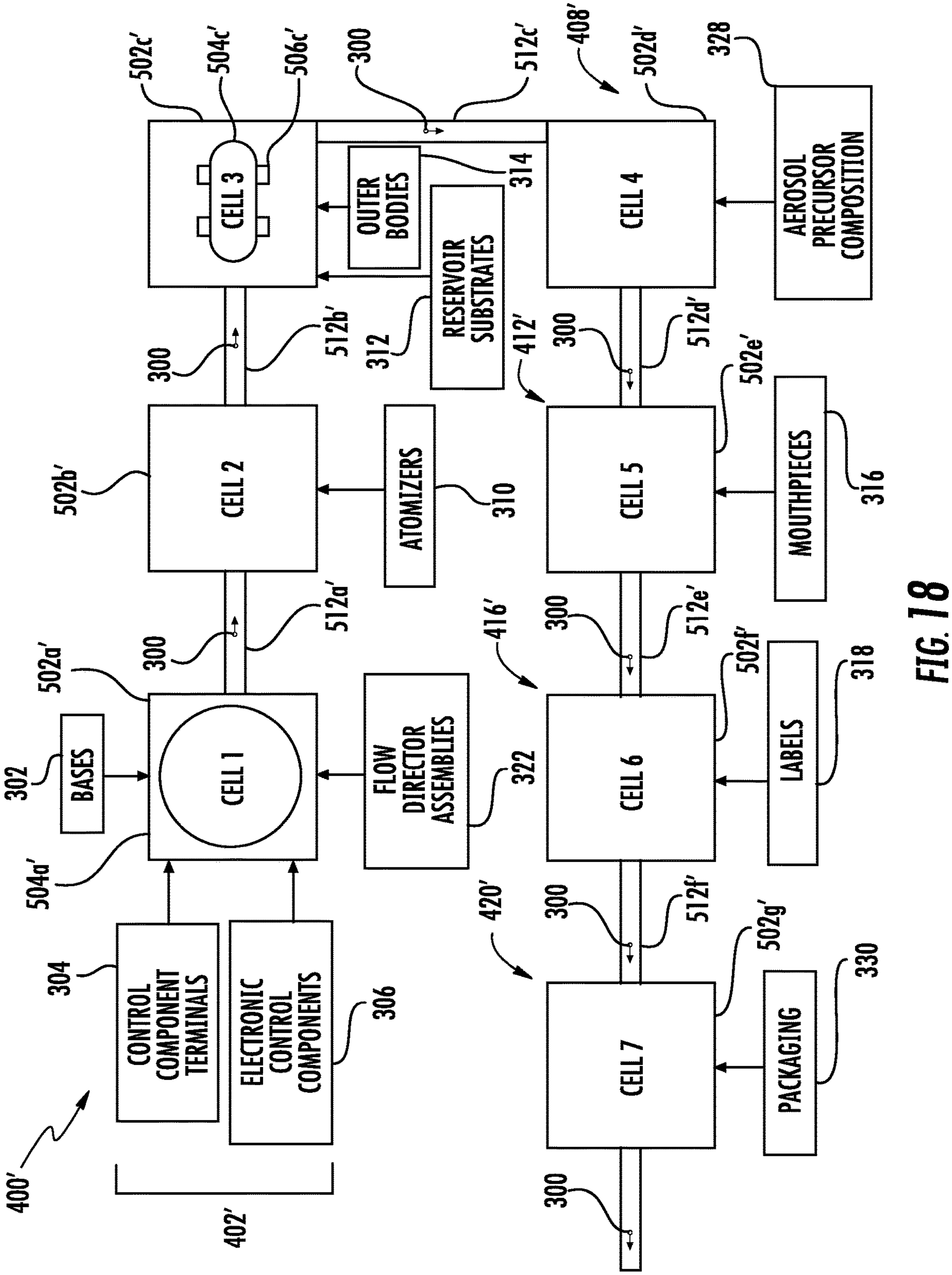
Figure 19:
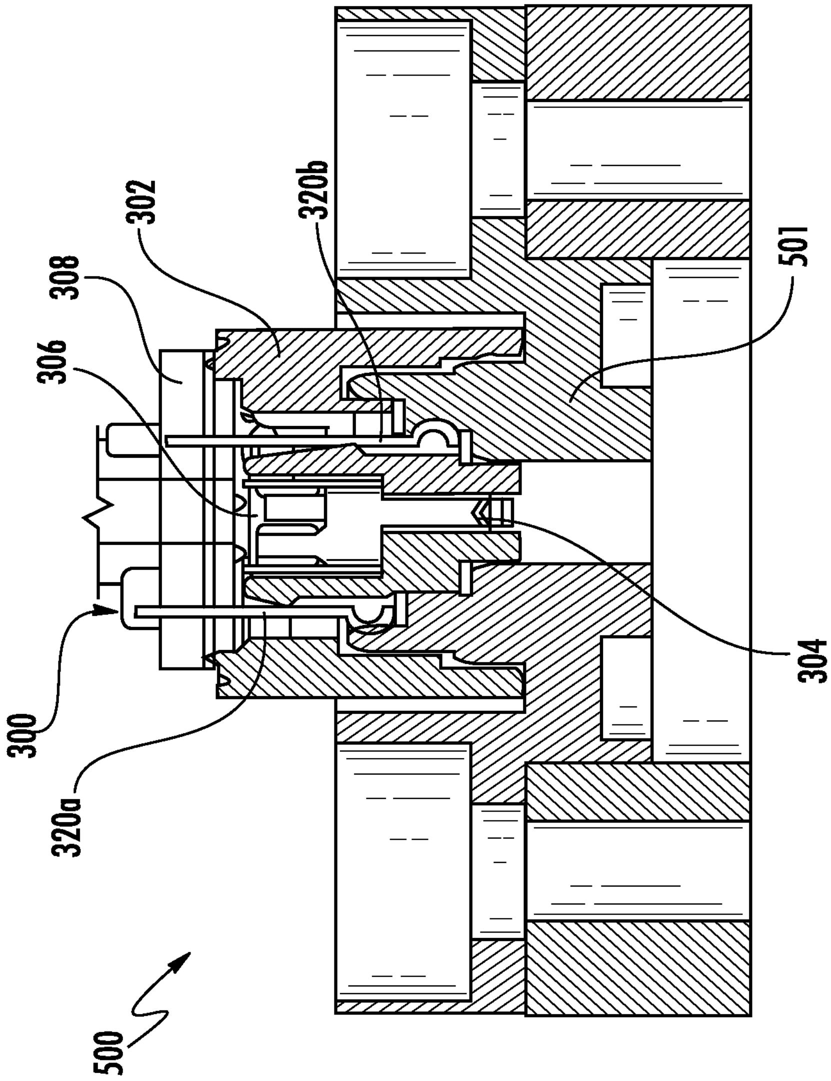
Figure 20:
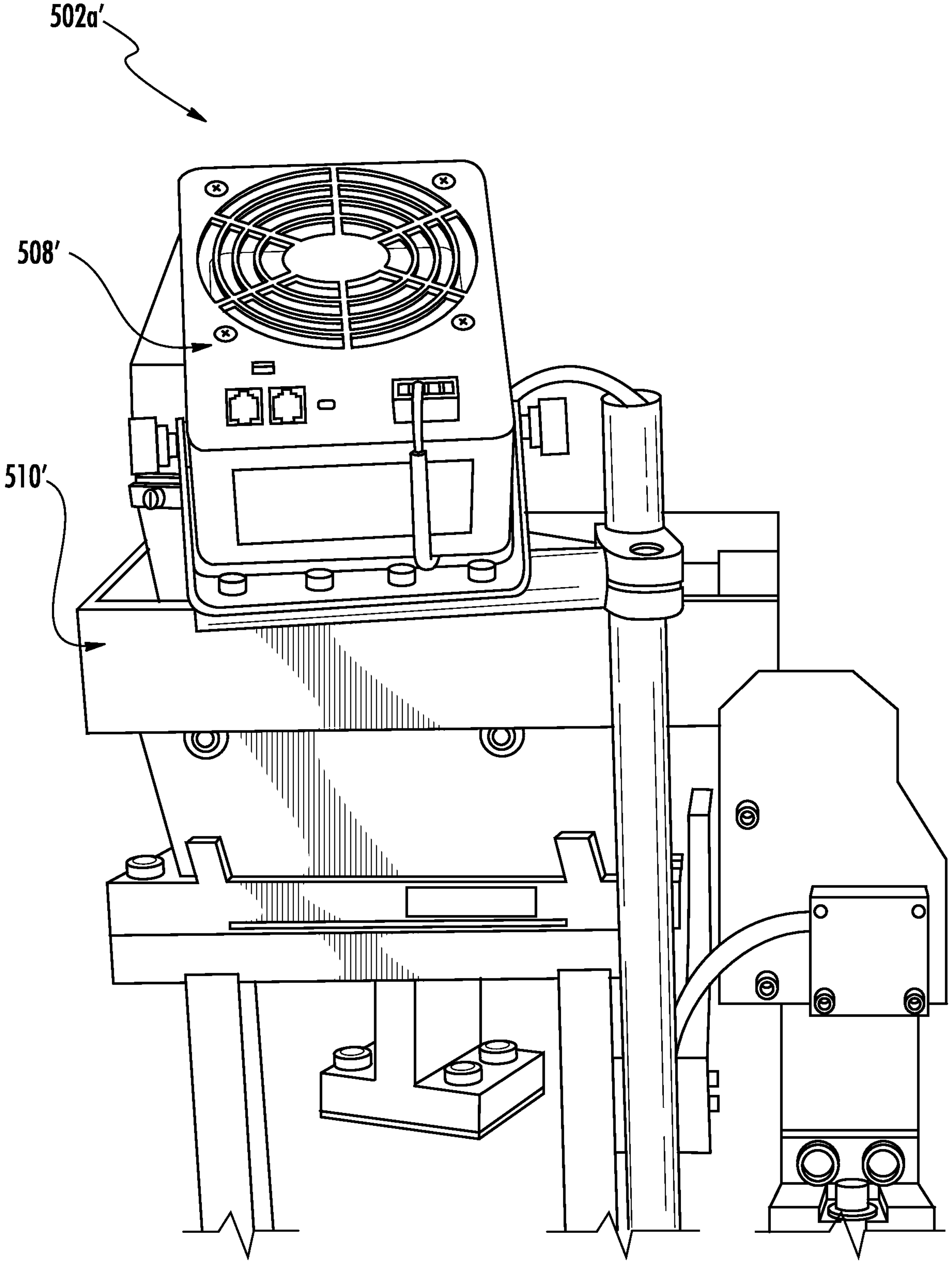
Figure 21:
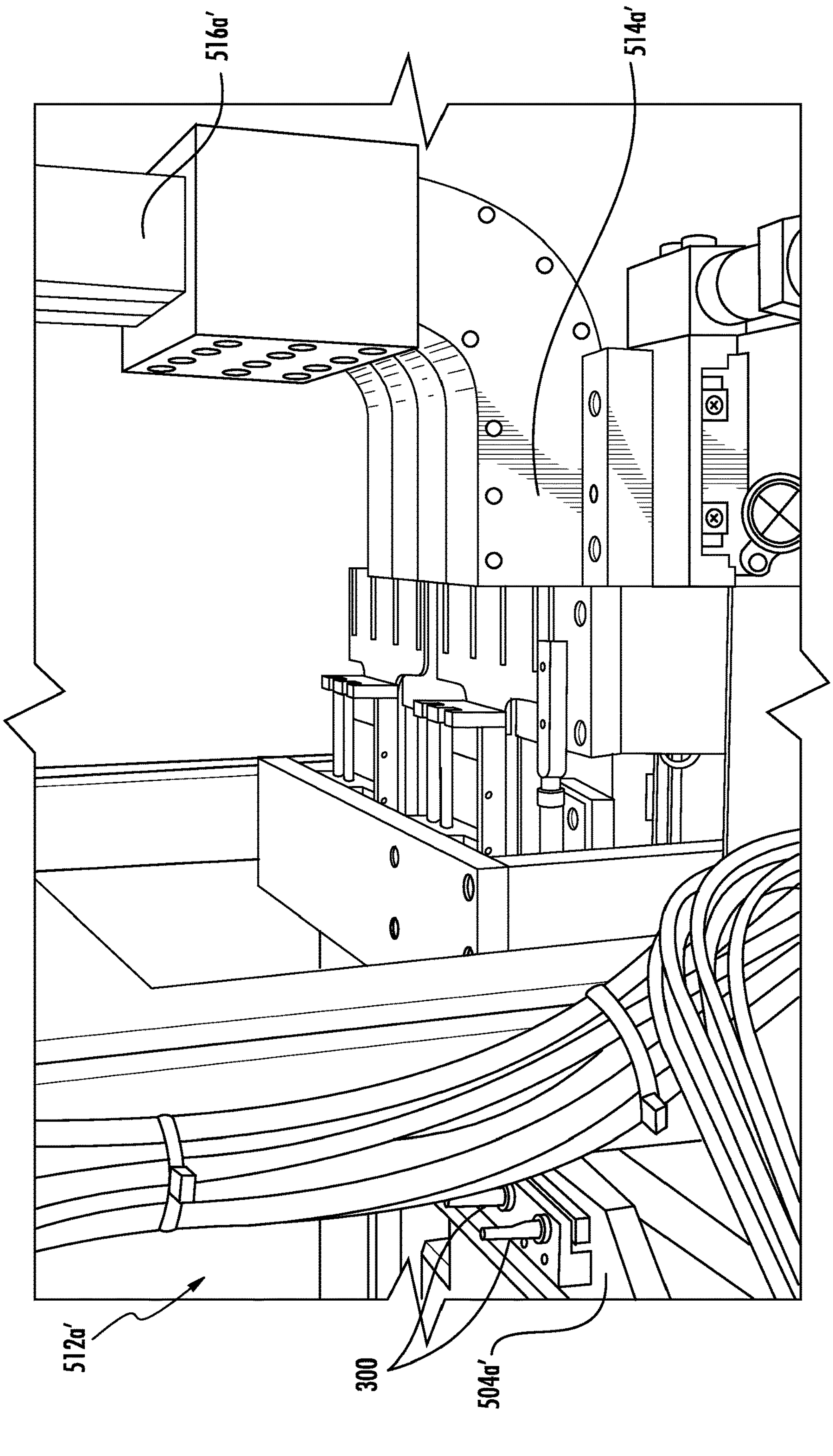
Figure 22:
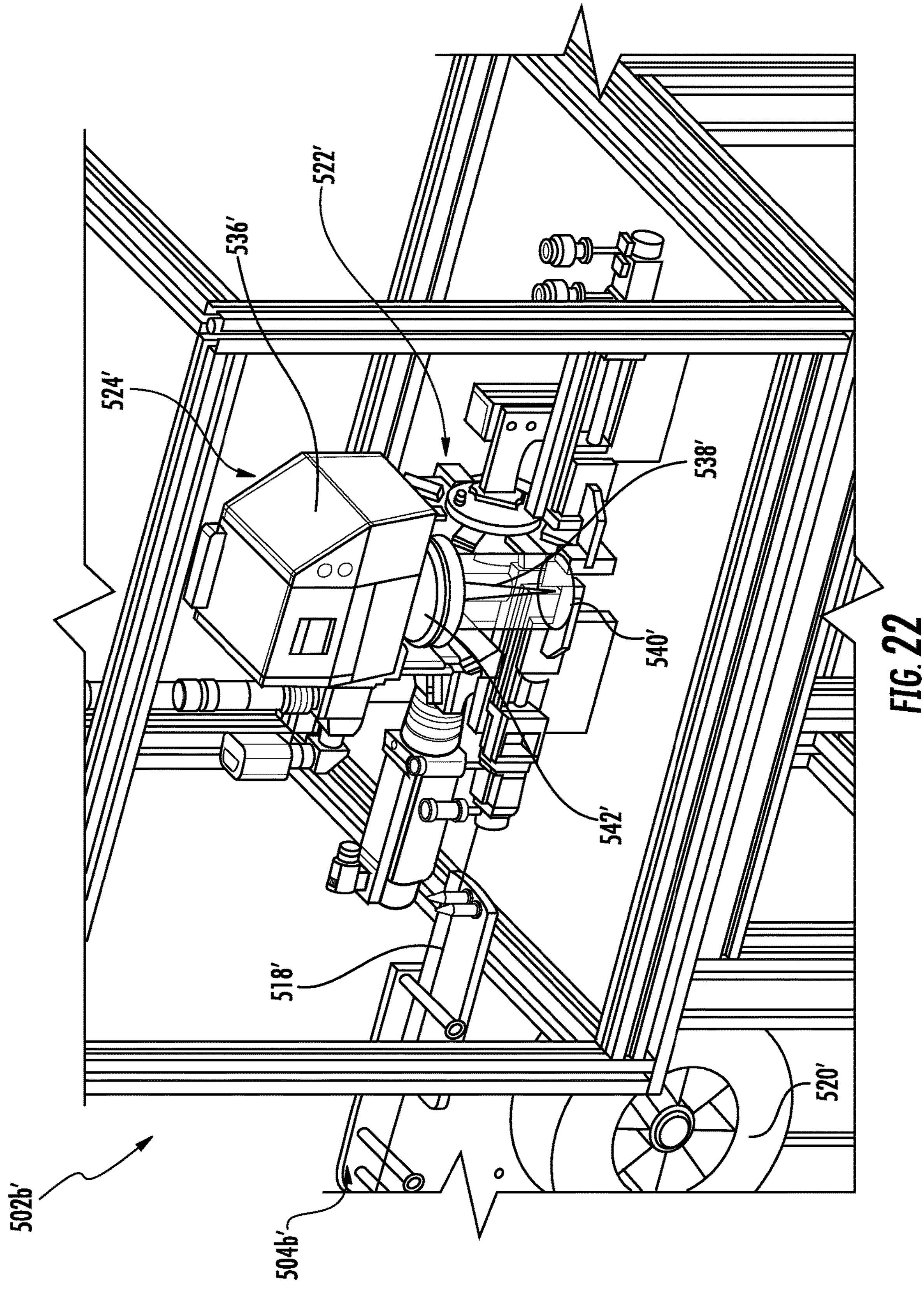
Figure 23:
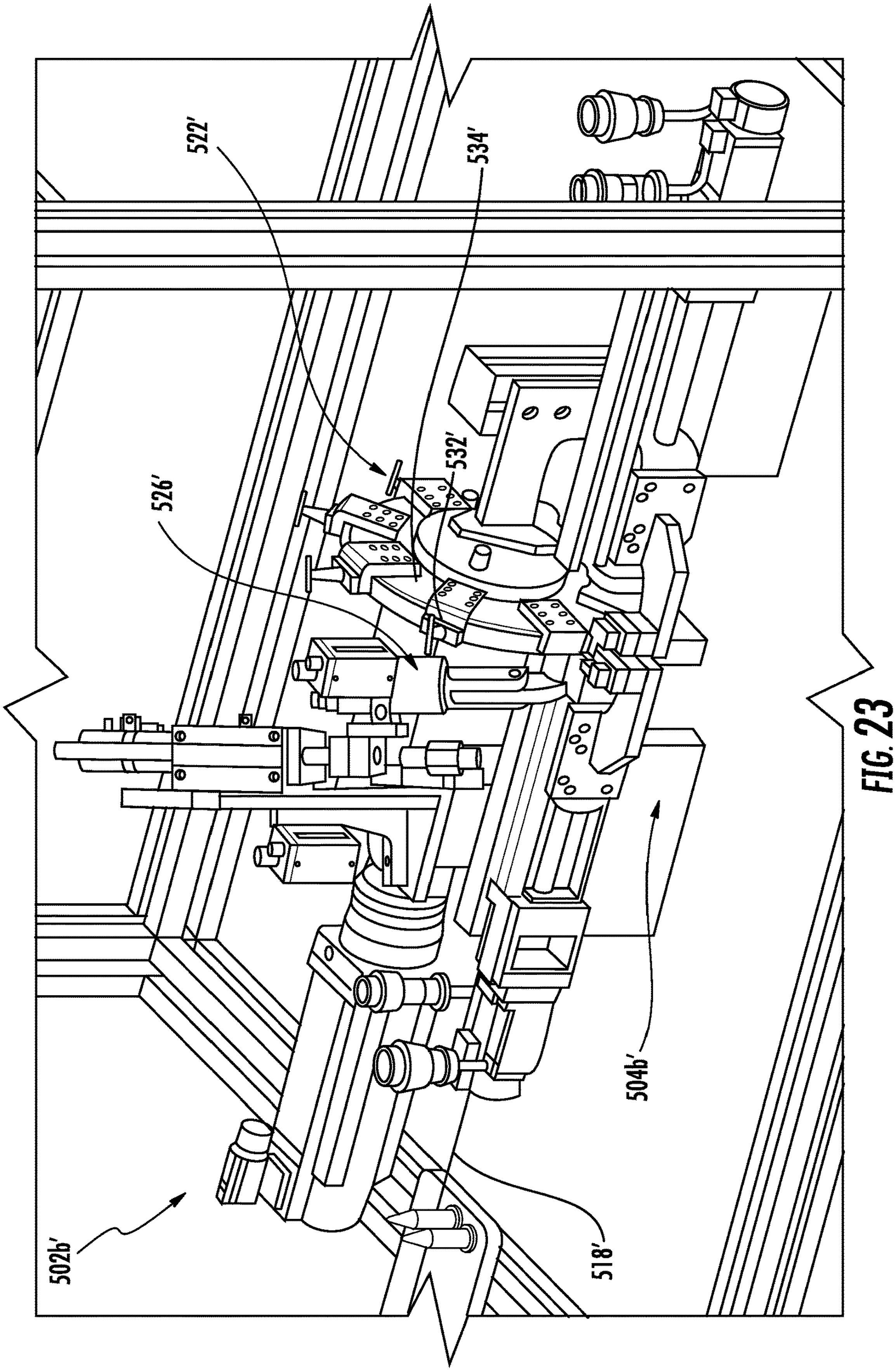
Figure 24:
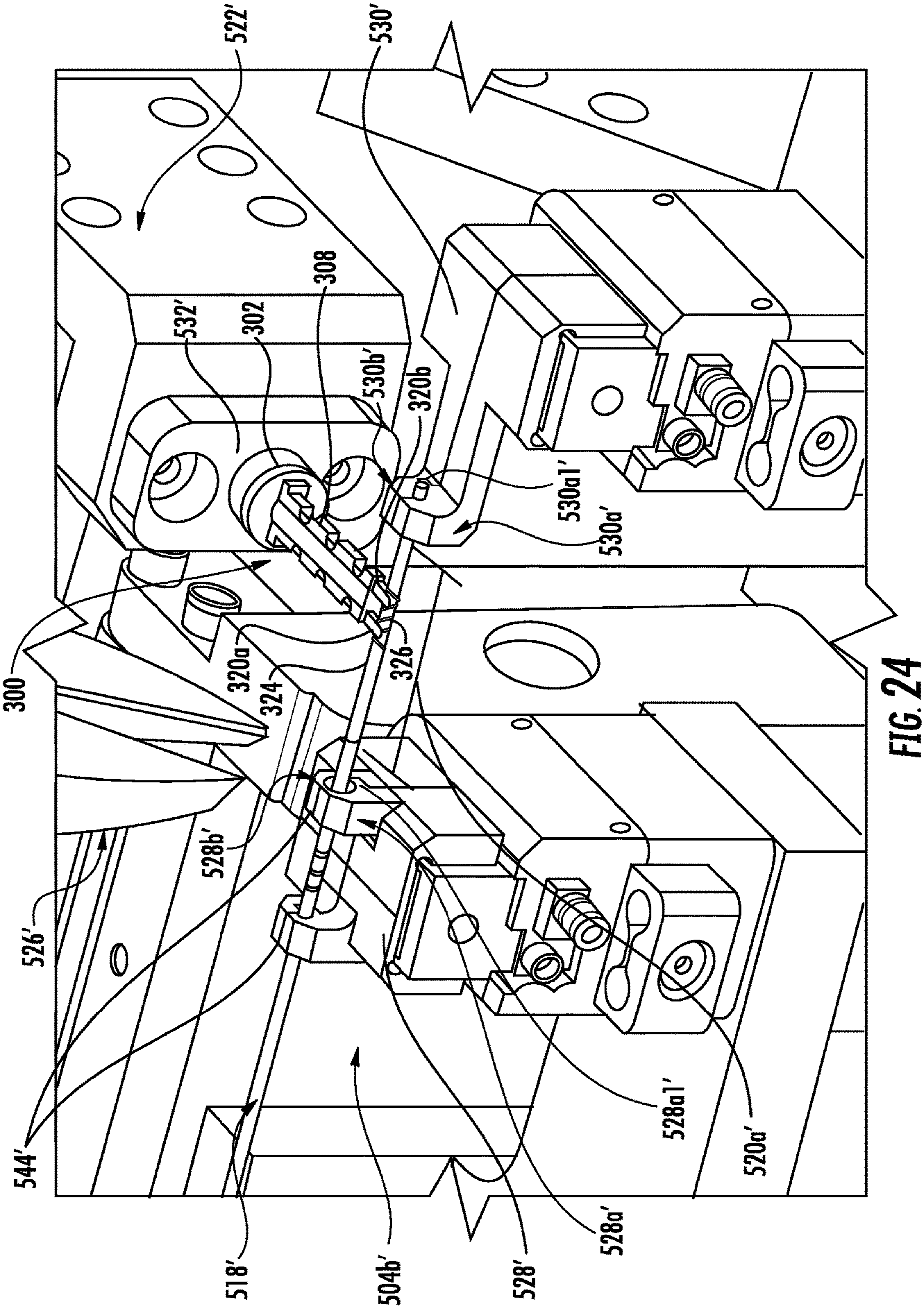
Figure 25:
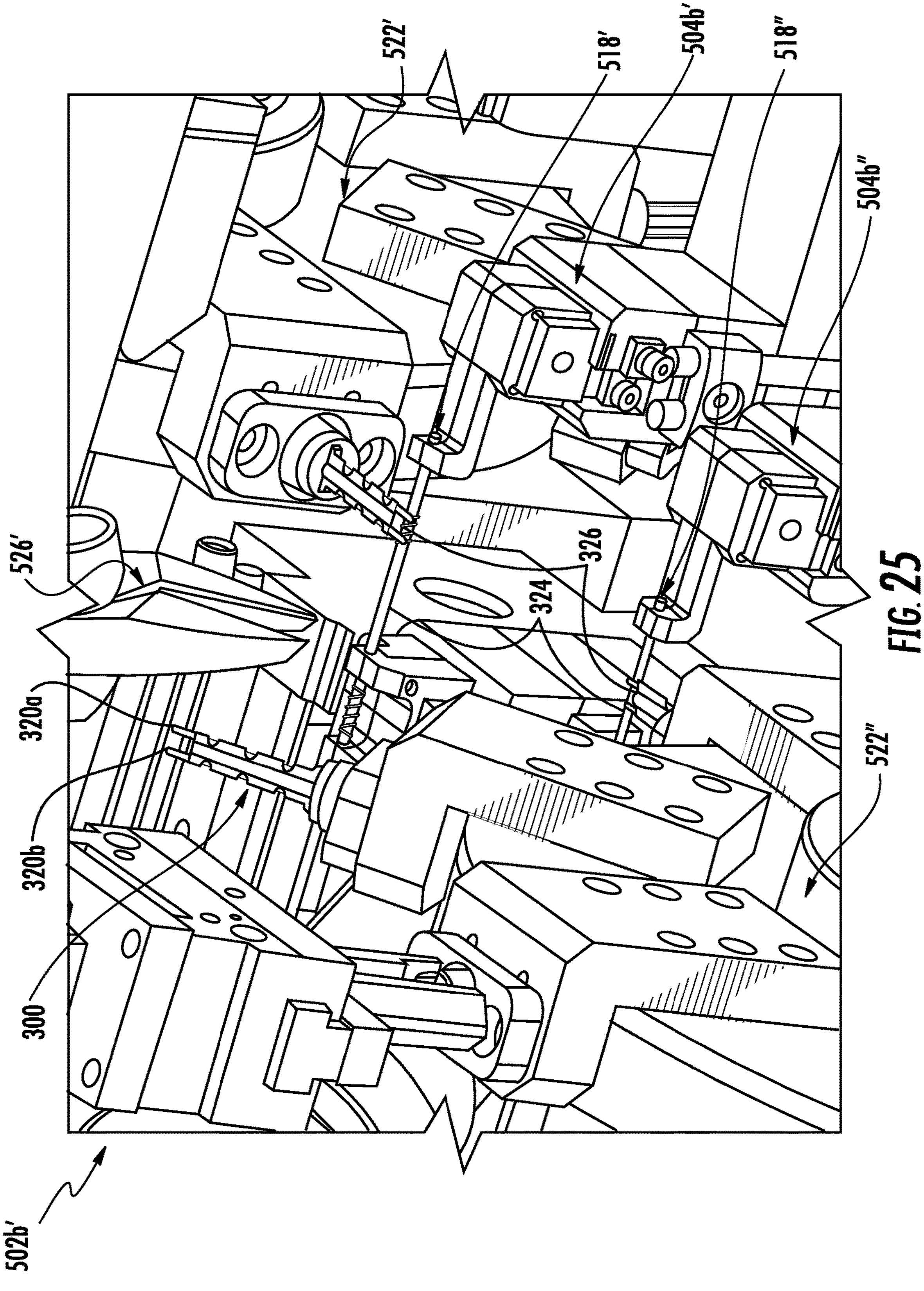
Figure 26:
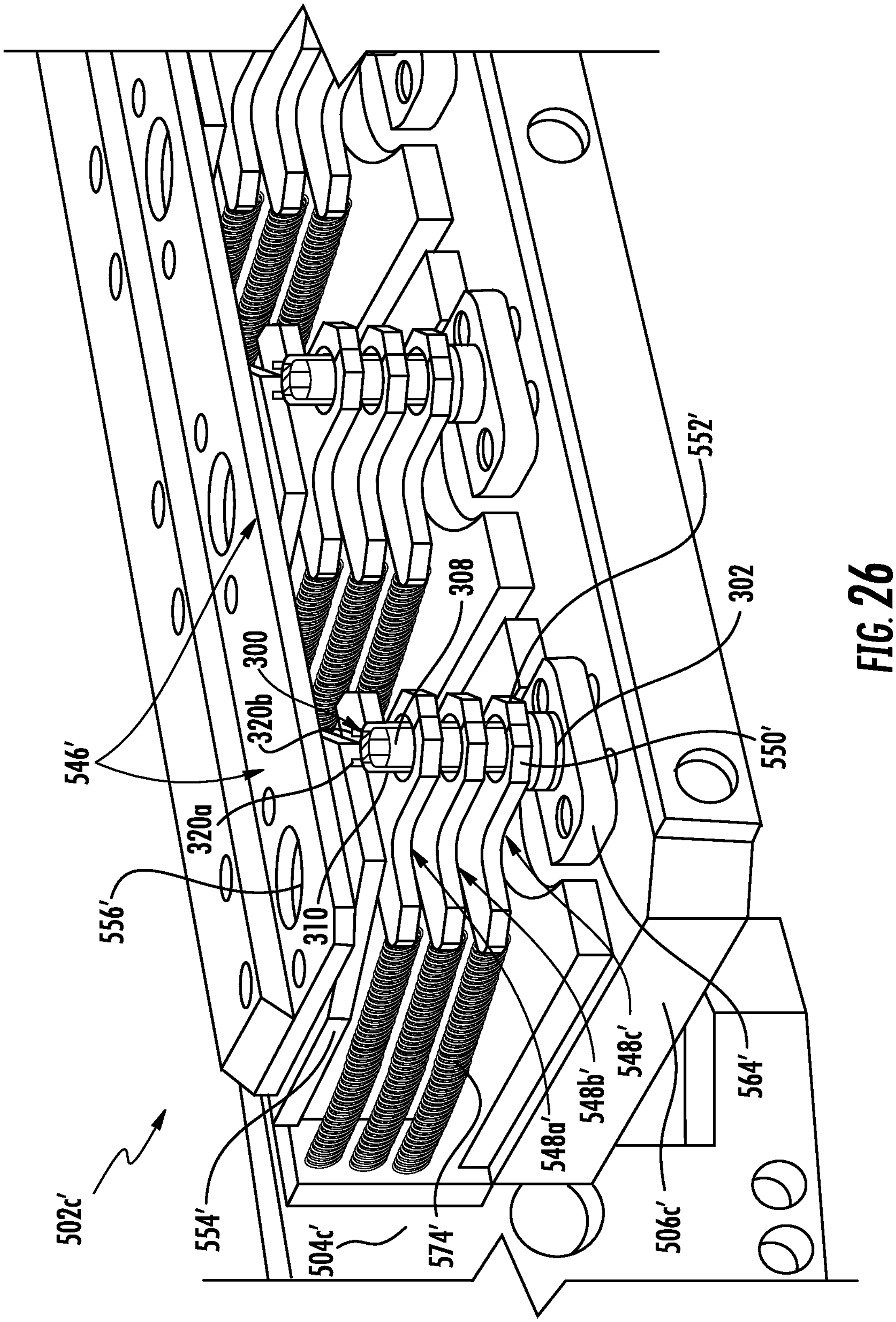
Figure 27:
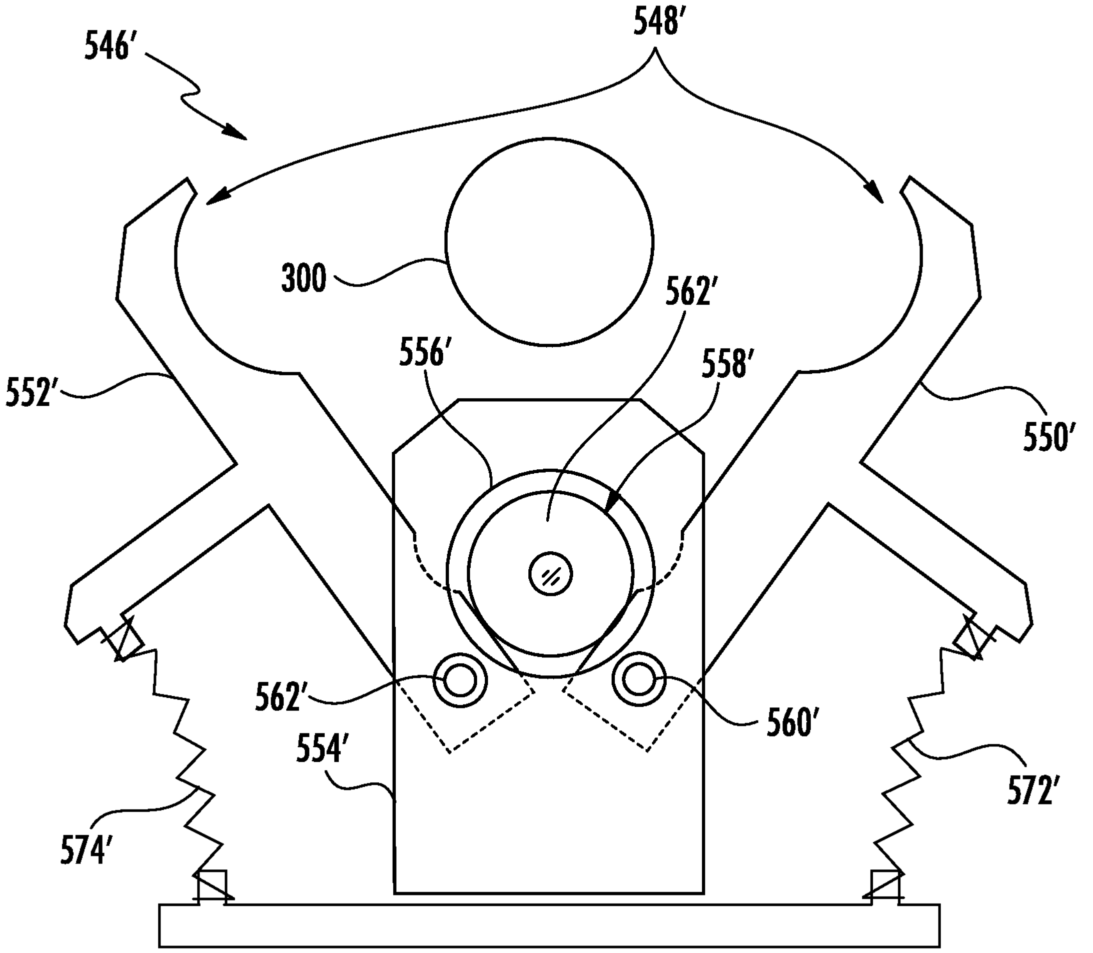
Figure 28:
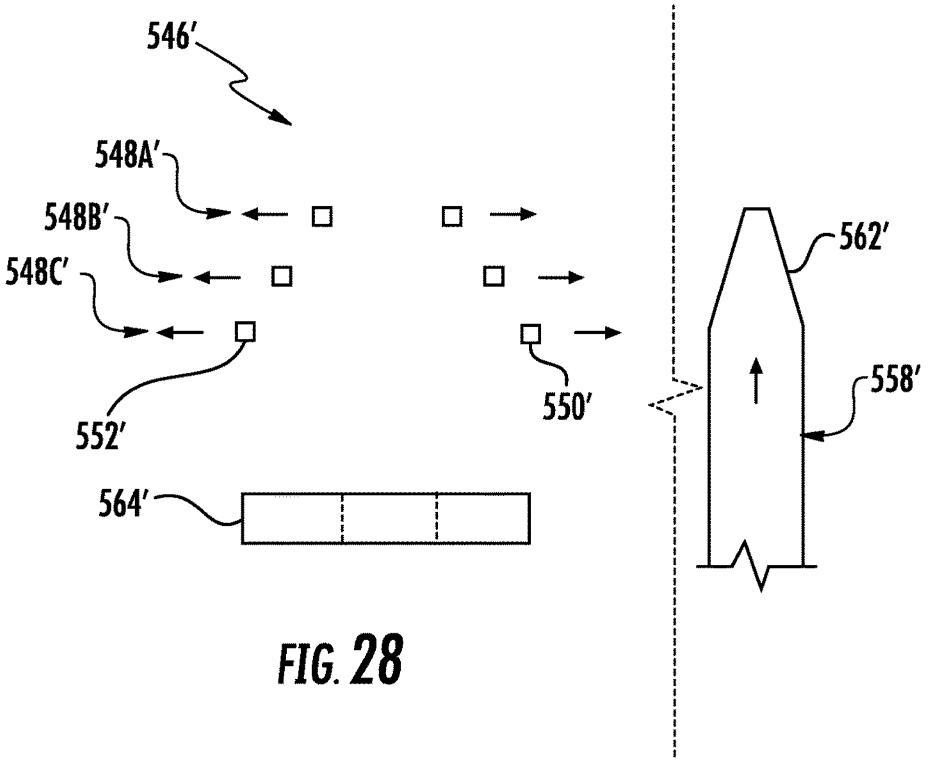
Figure 29:
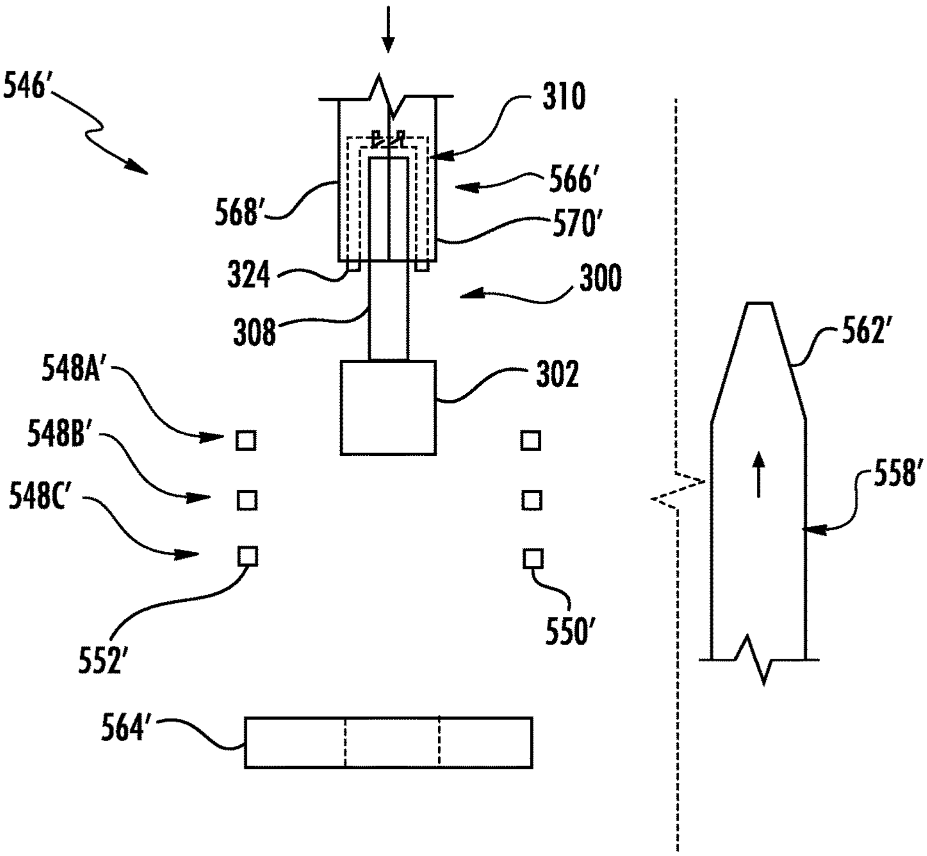
Figure 30:
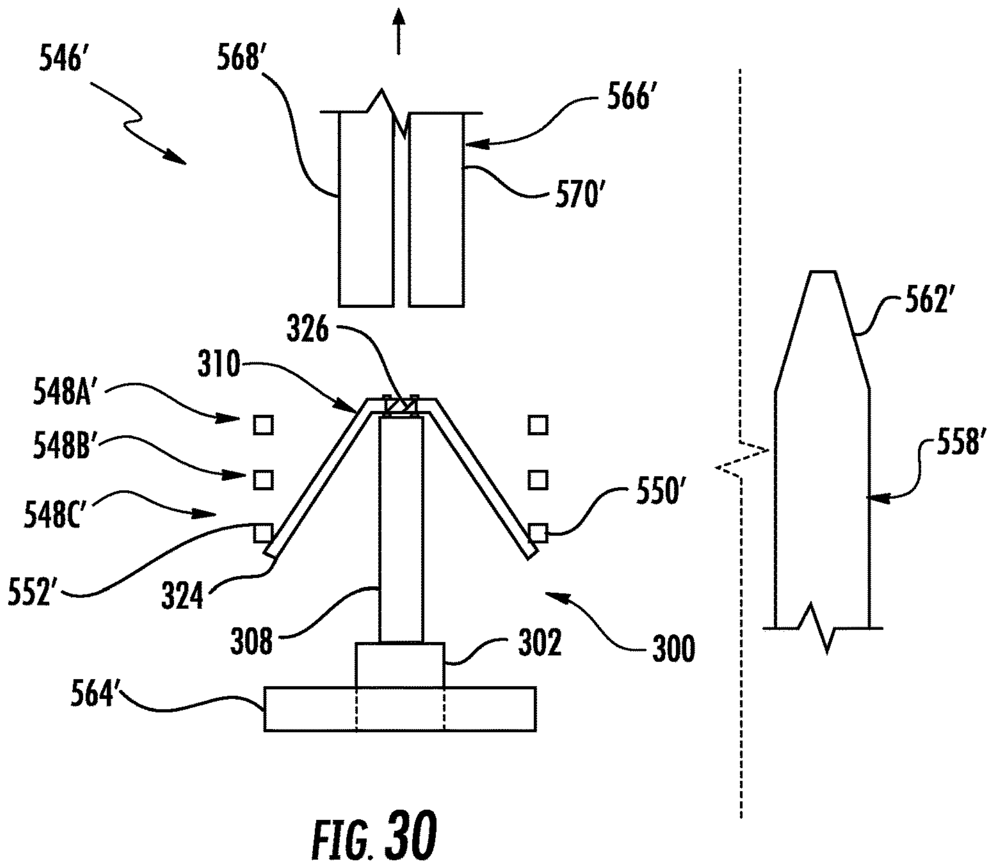
Figure 31:
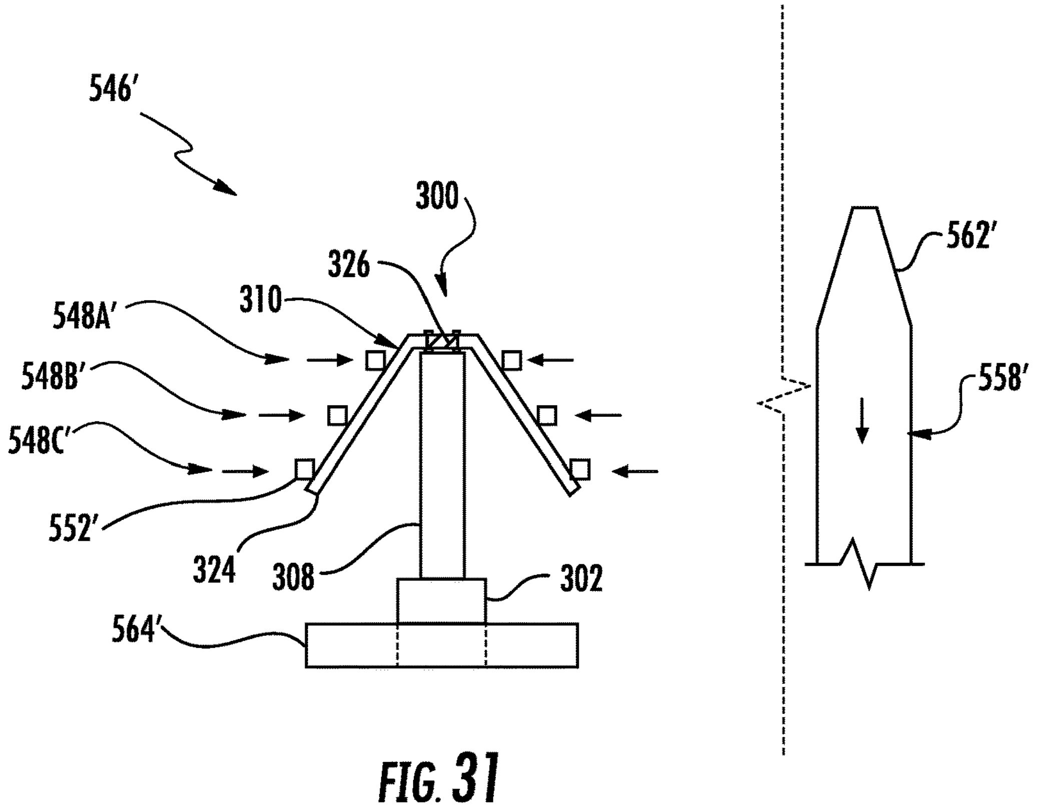
Figure 32:
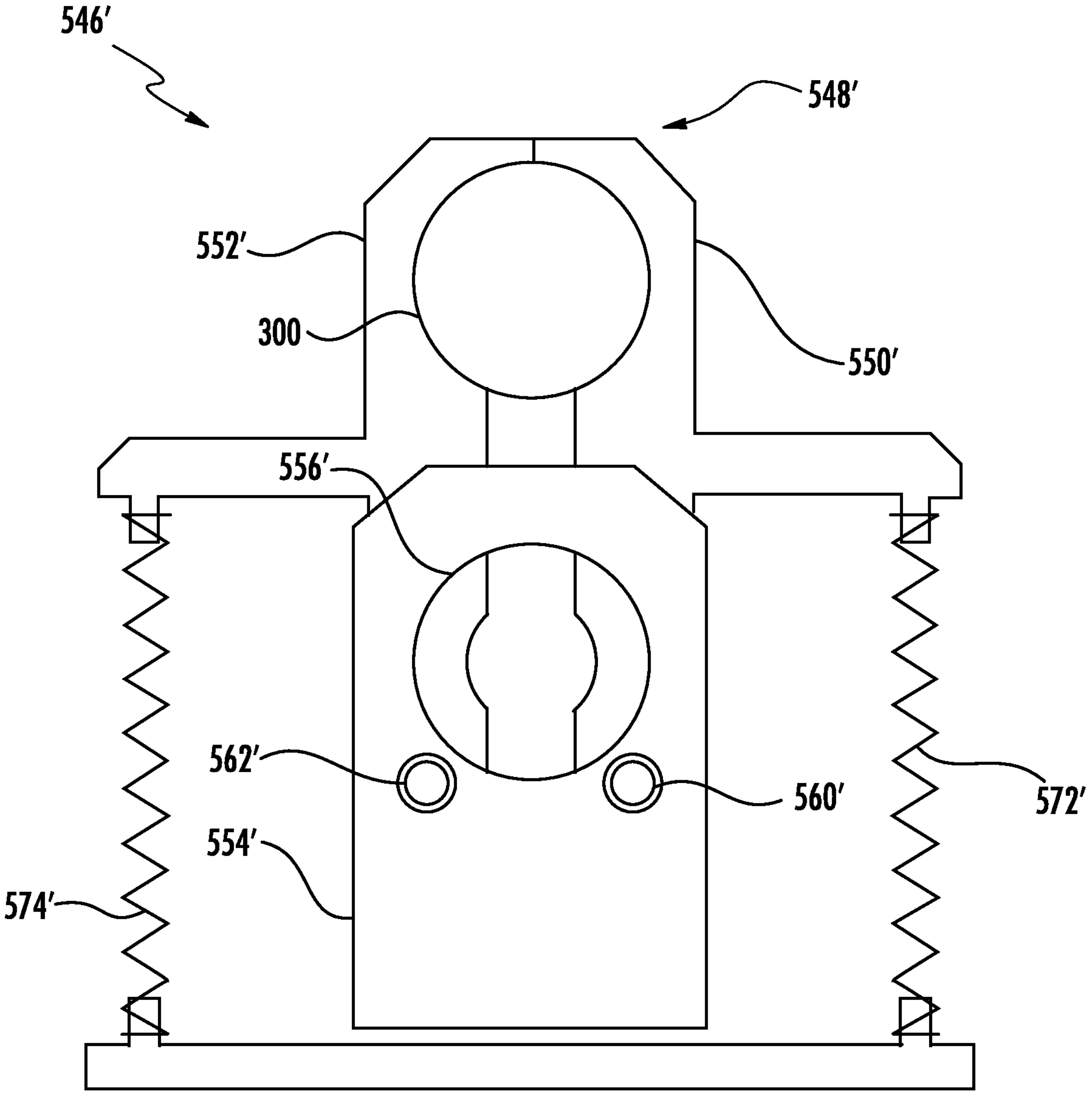
Figure 33:
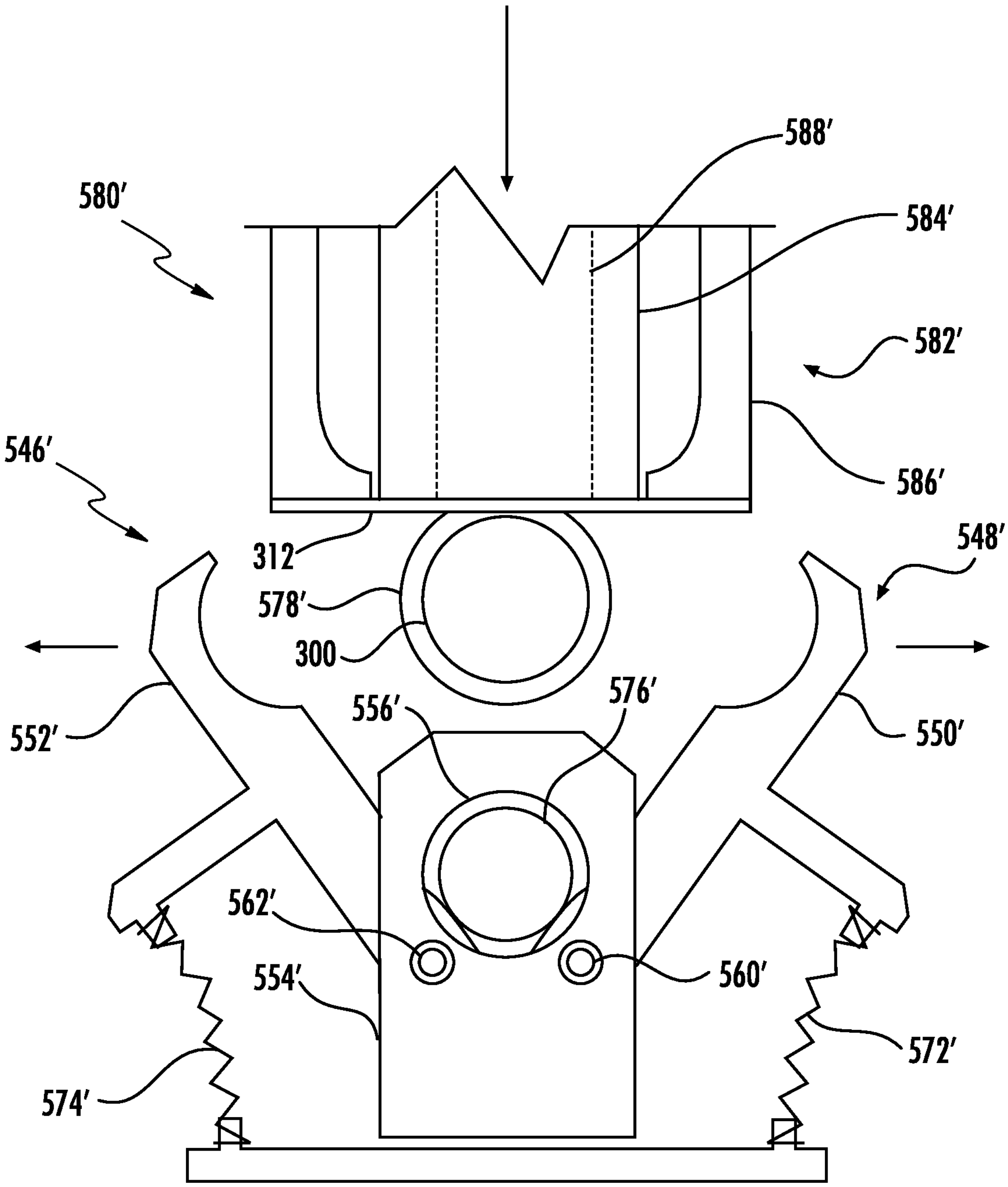
Figure 34:
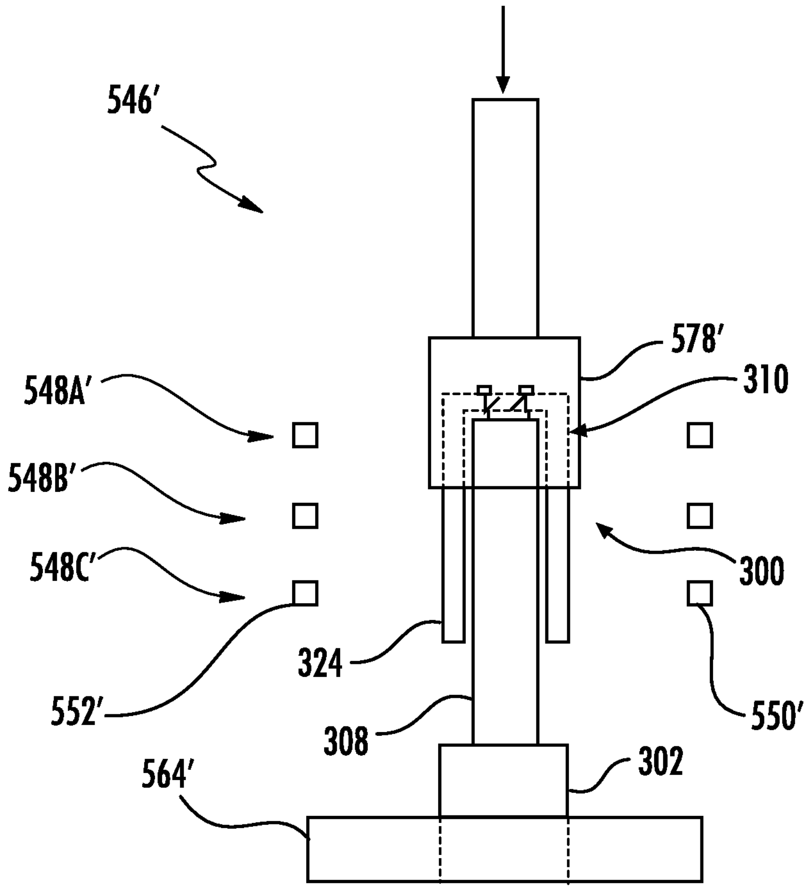
Figure 35:
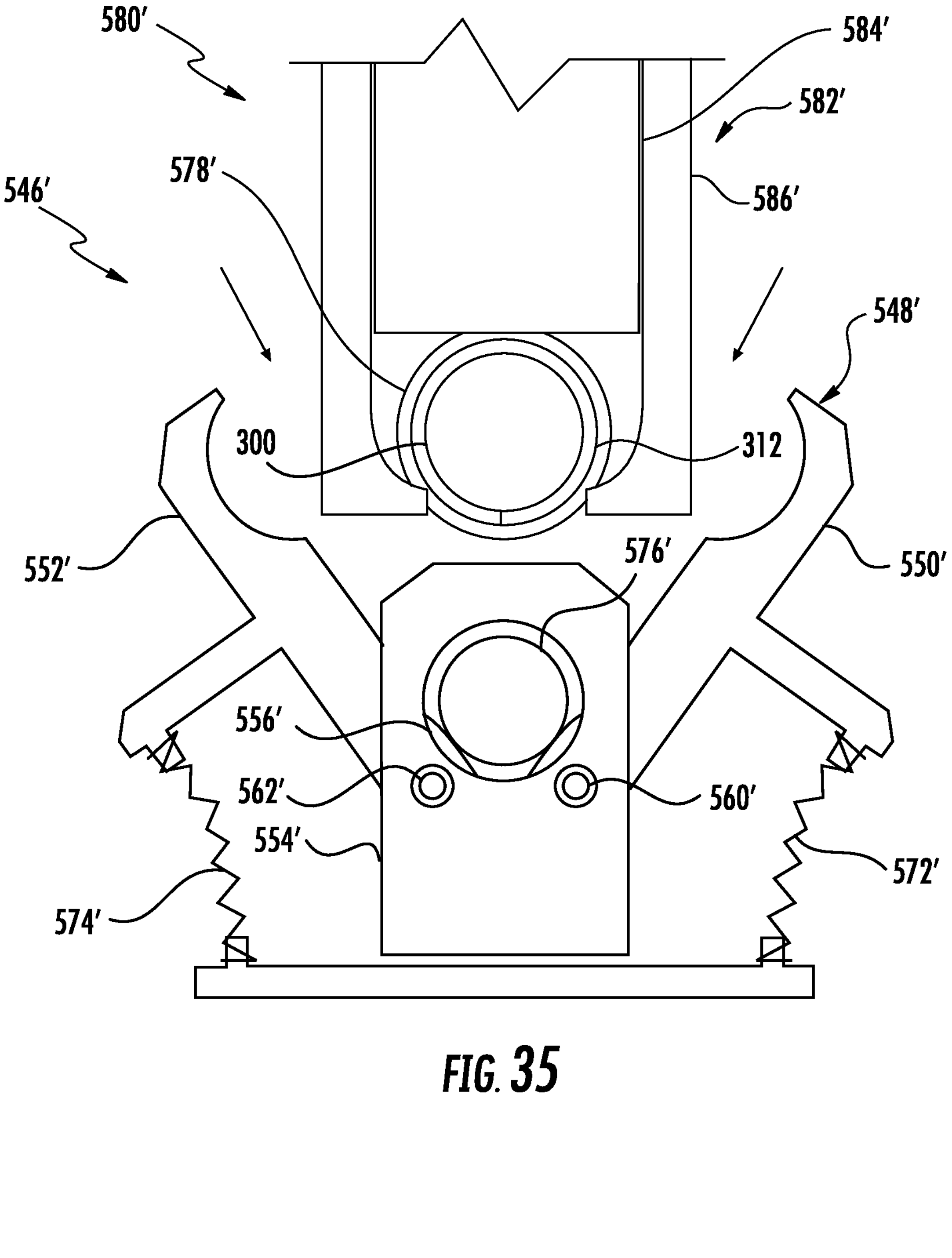
Figure 36:
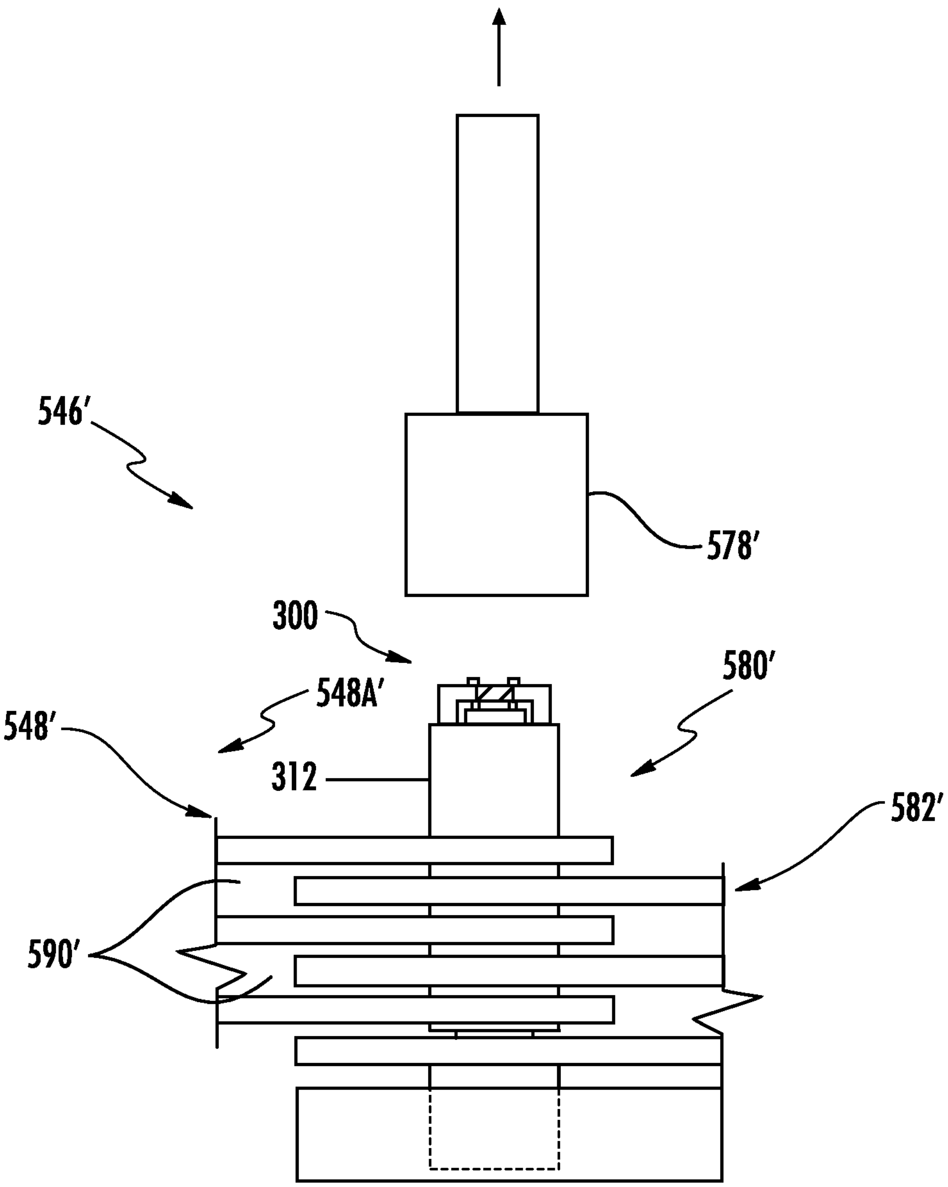
Figure 37:
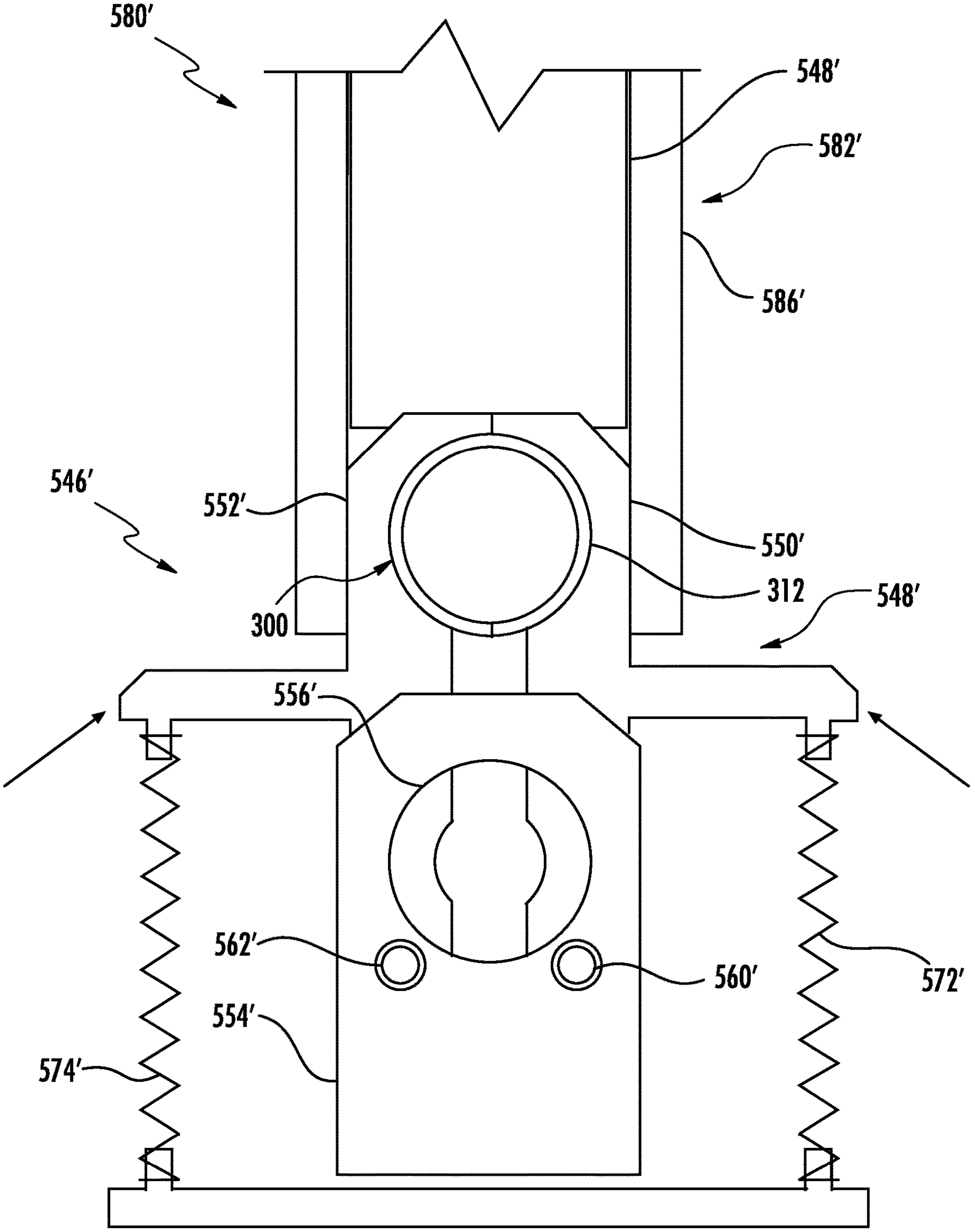
Figure 38:
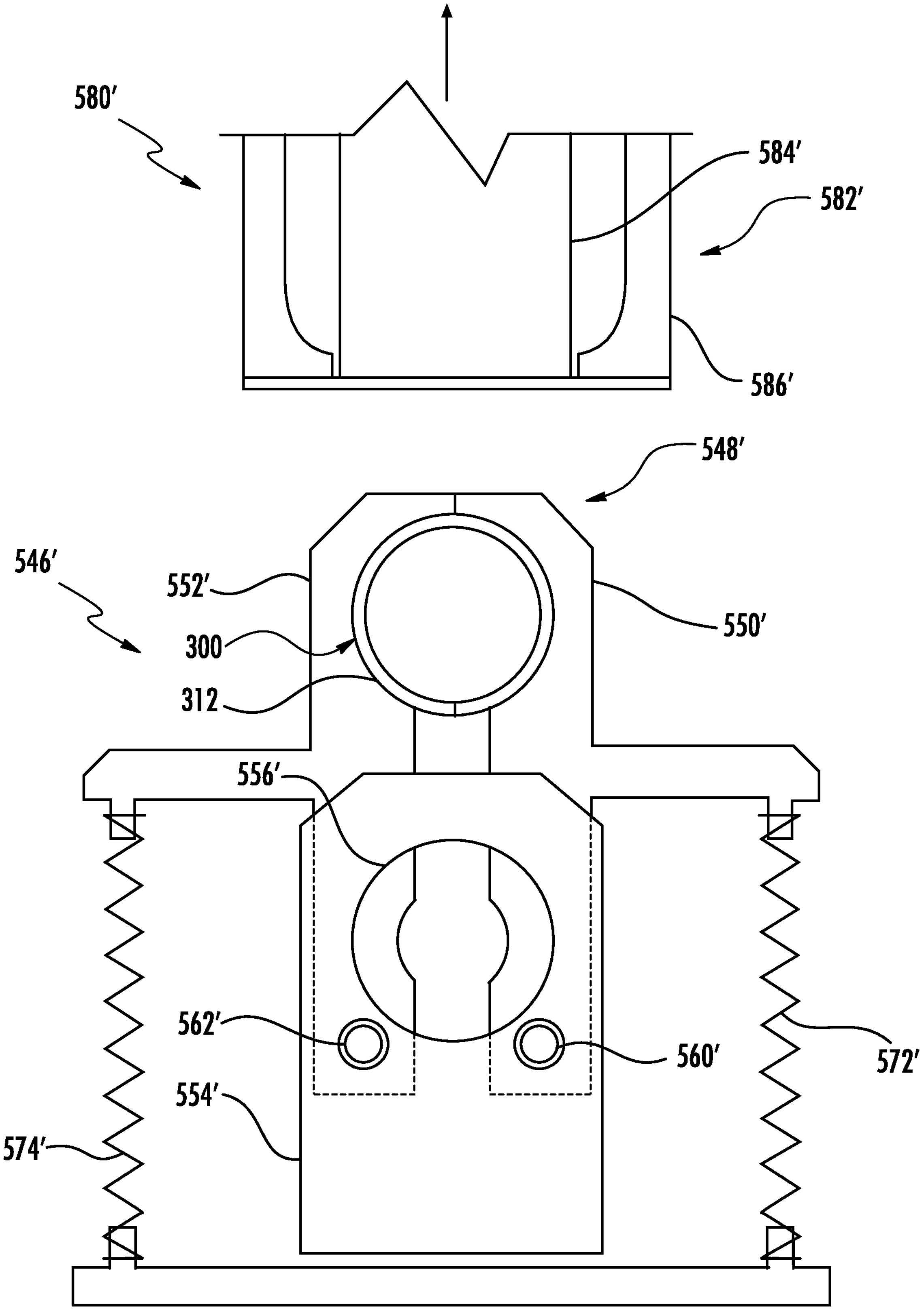
Figure 39:
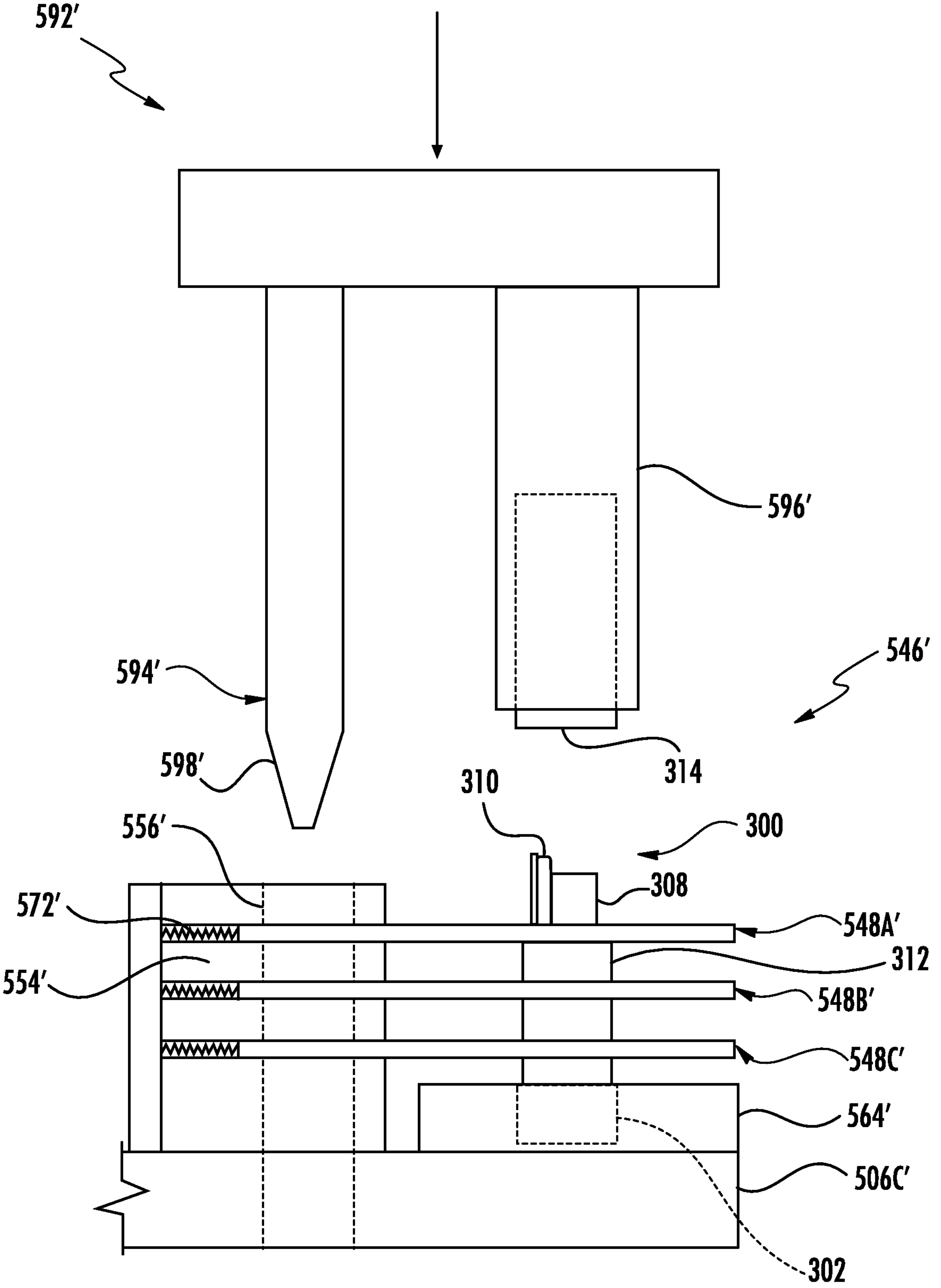
Figure 40:
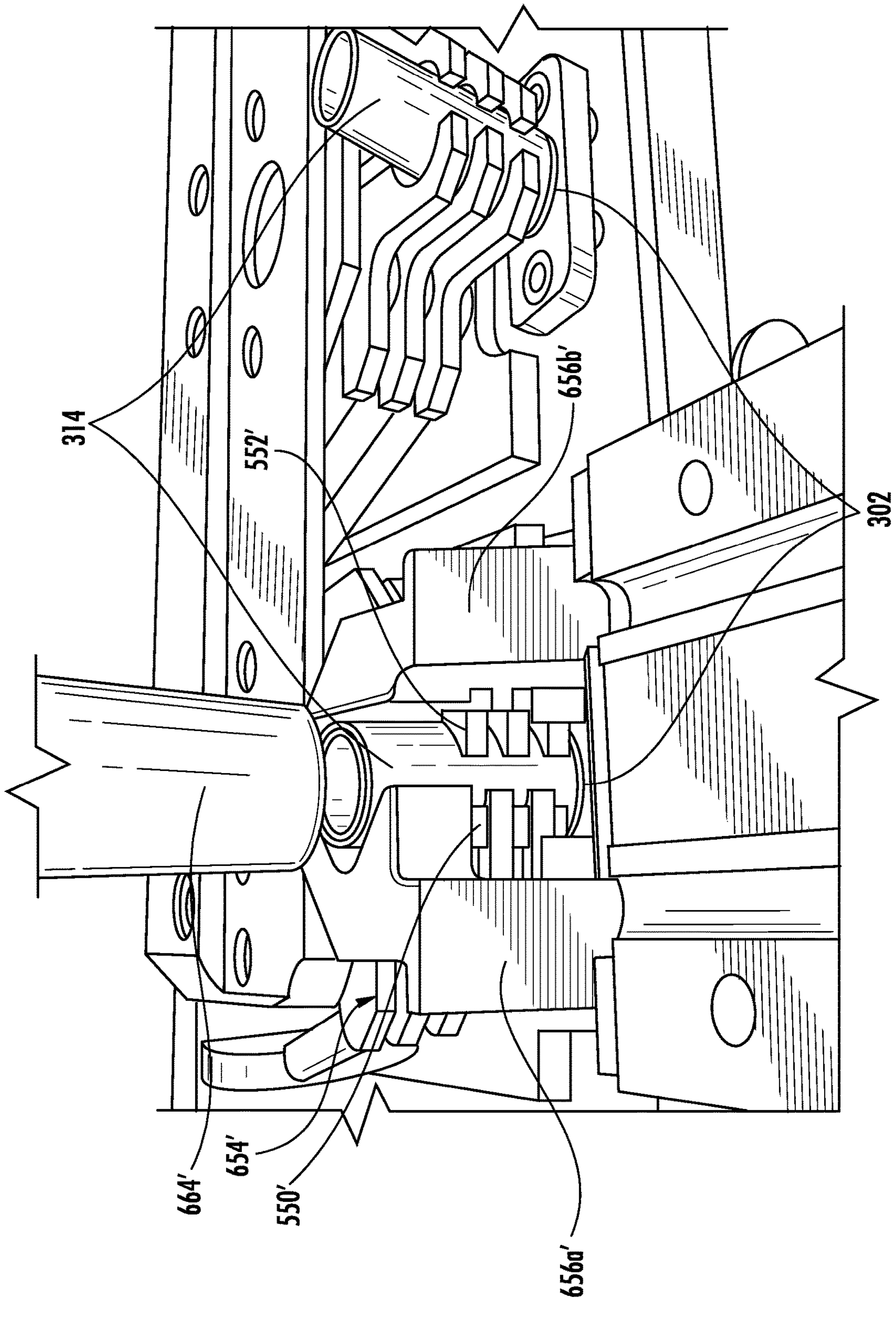
Figure 41:
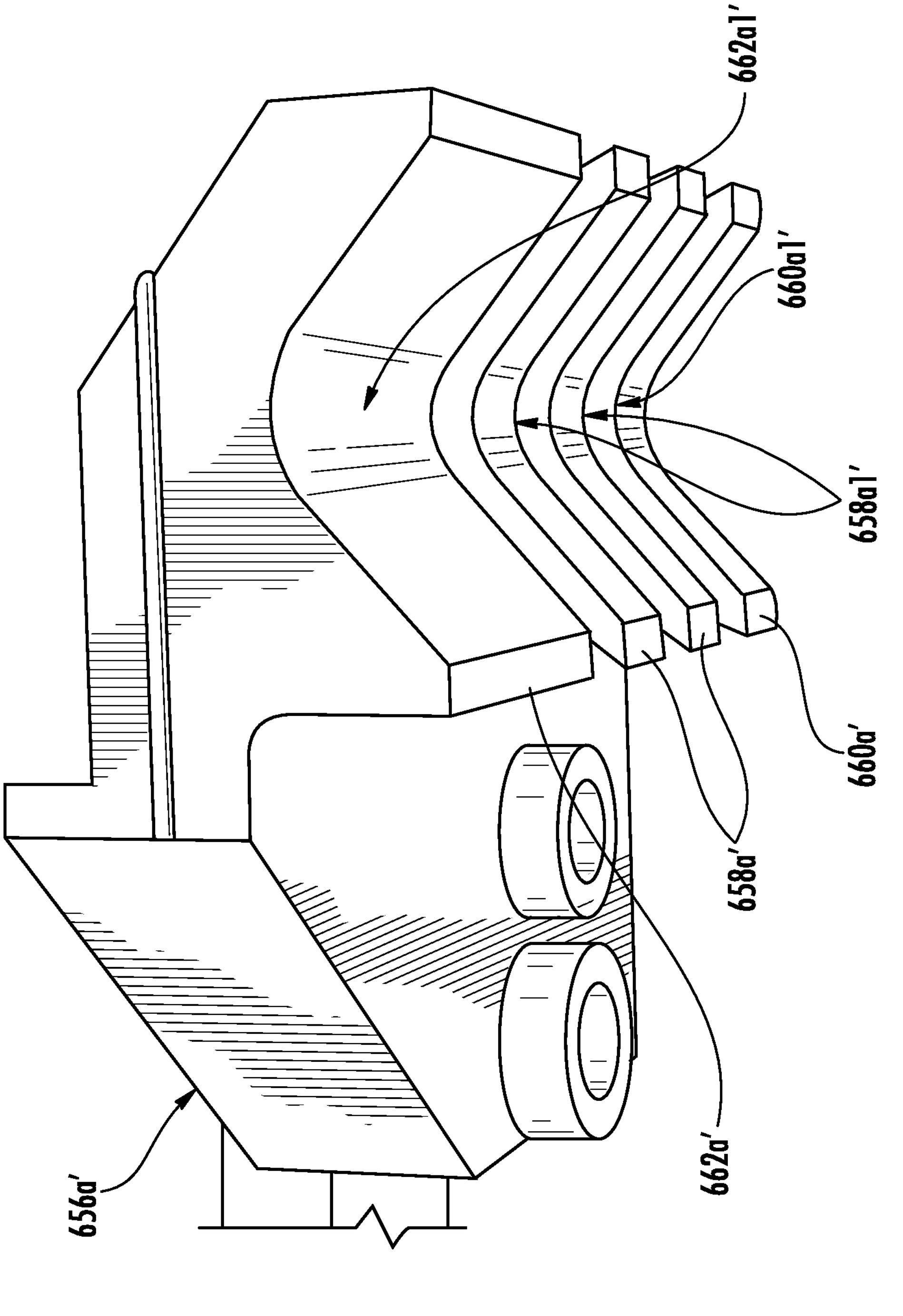
Figure 42:
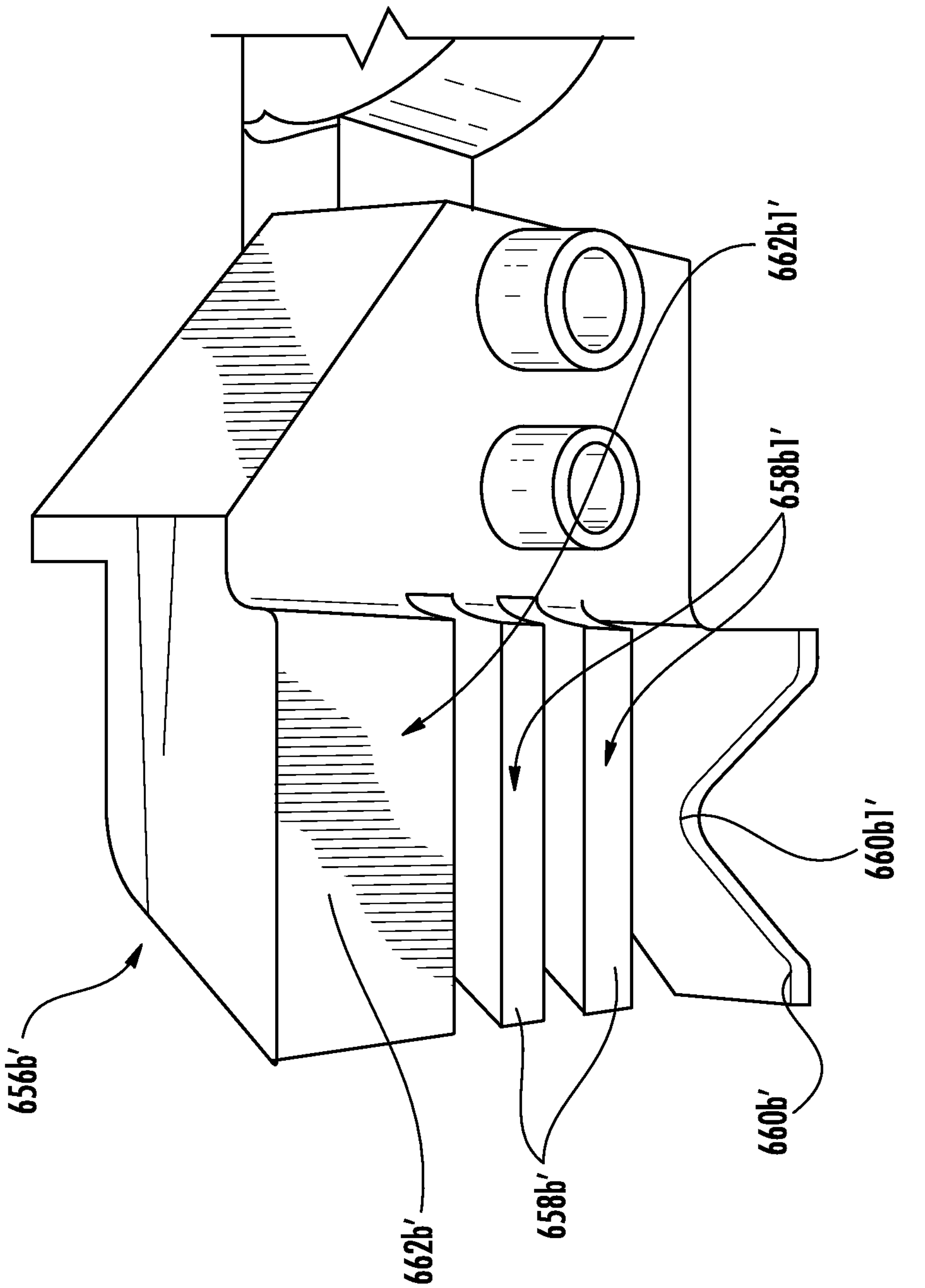
Figure 43:
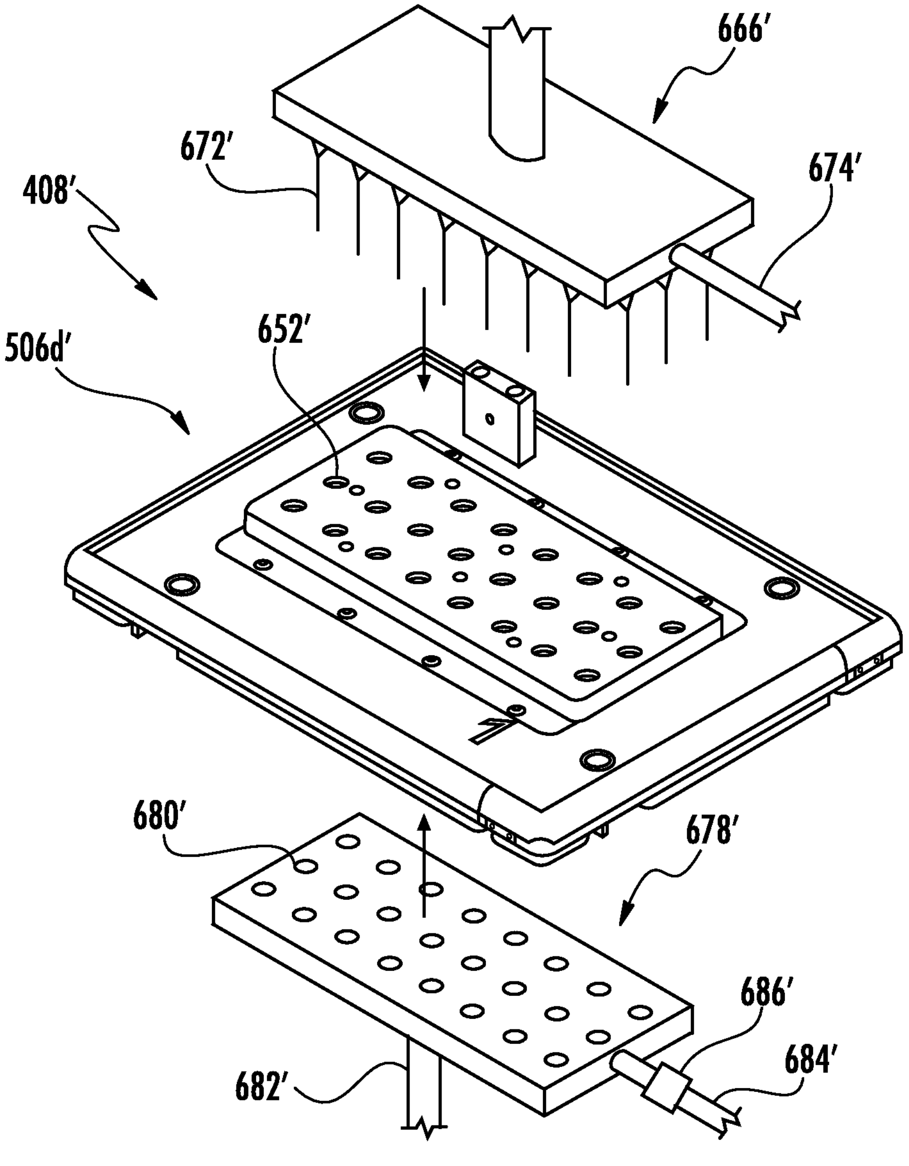
Figure 44:
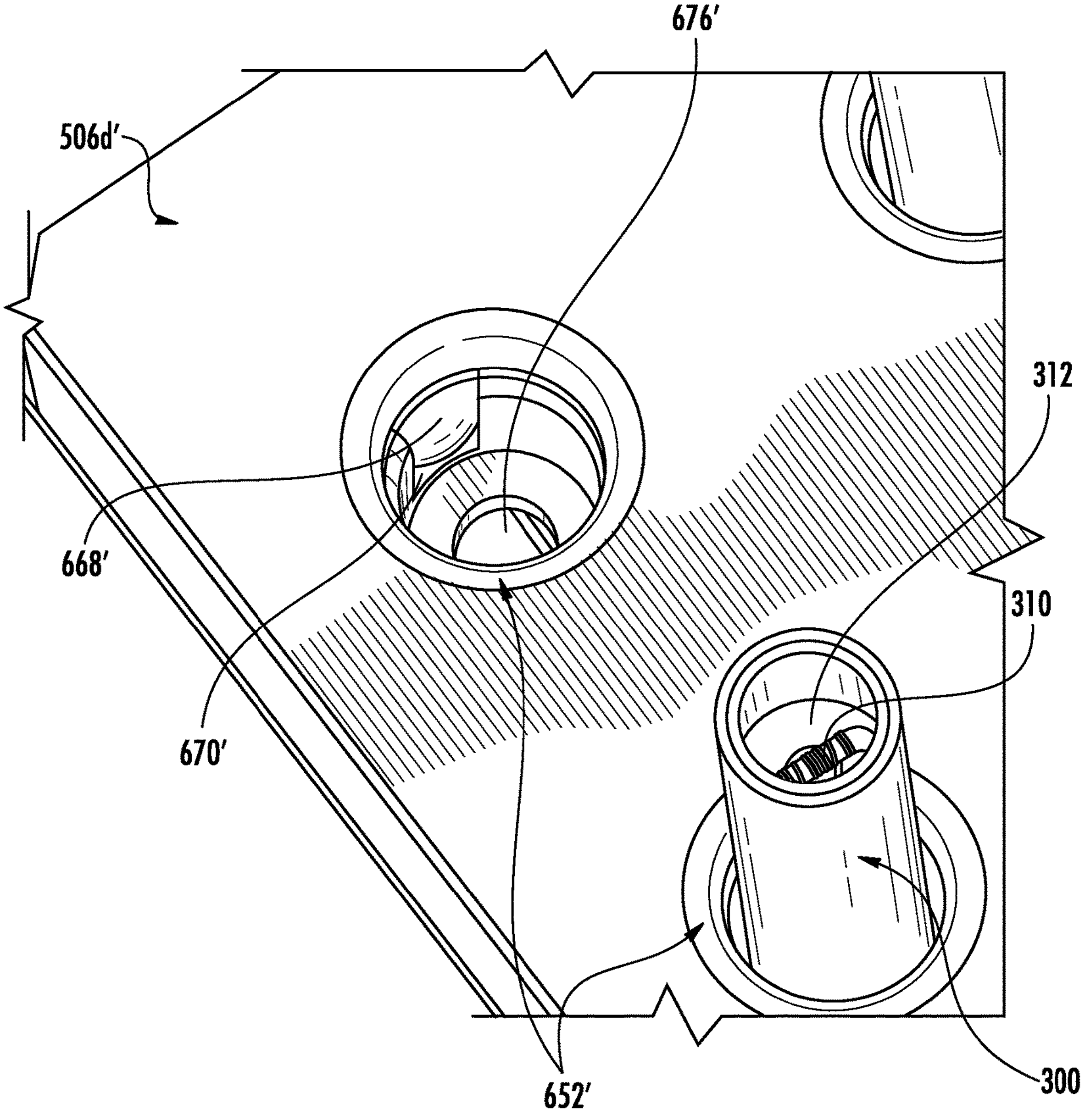
Figure 45:
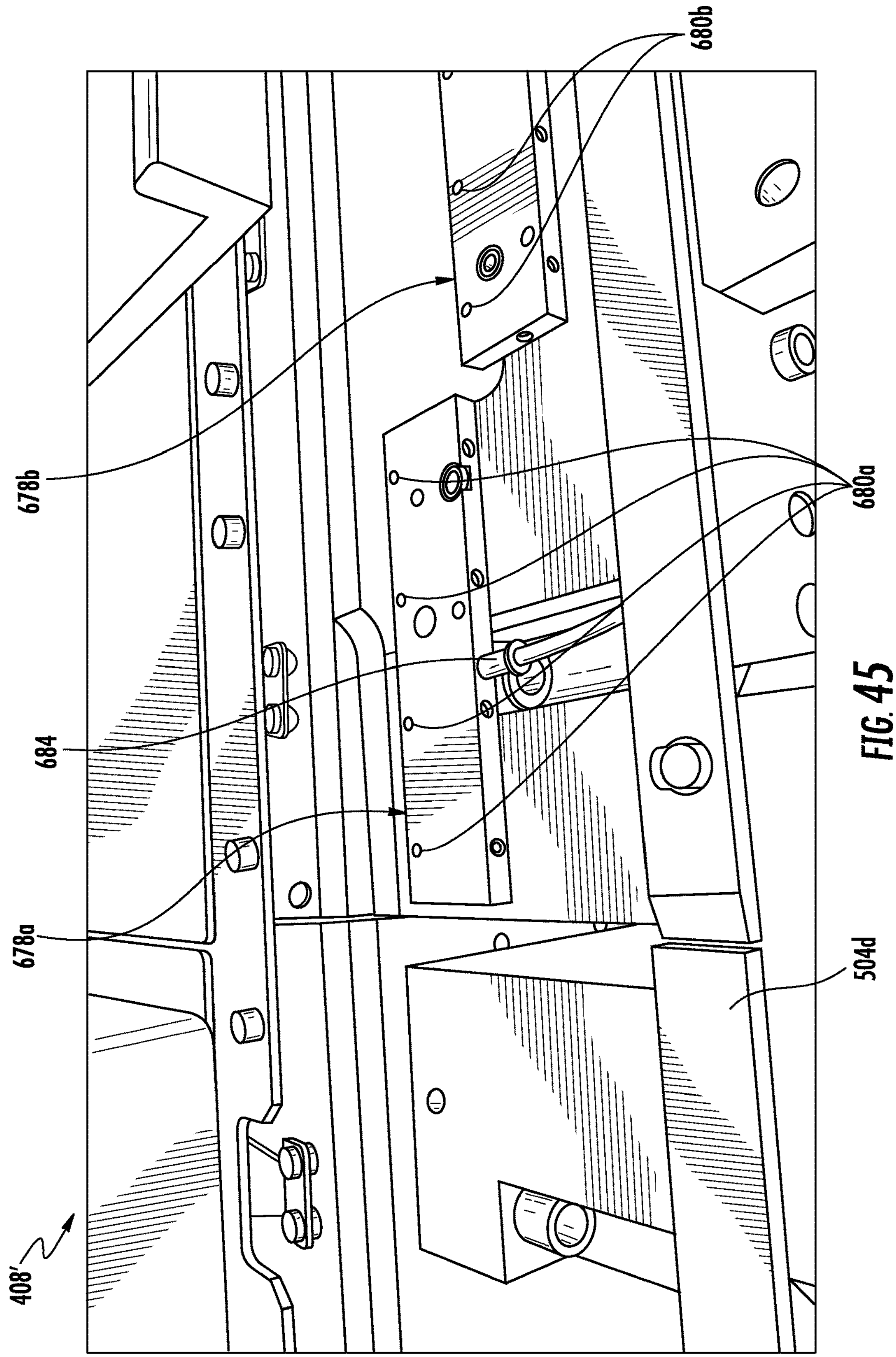
Figure 46:
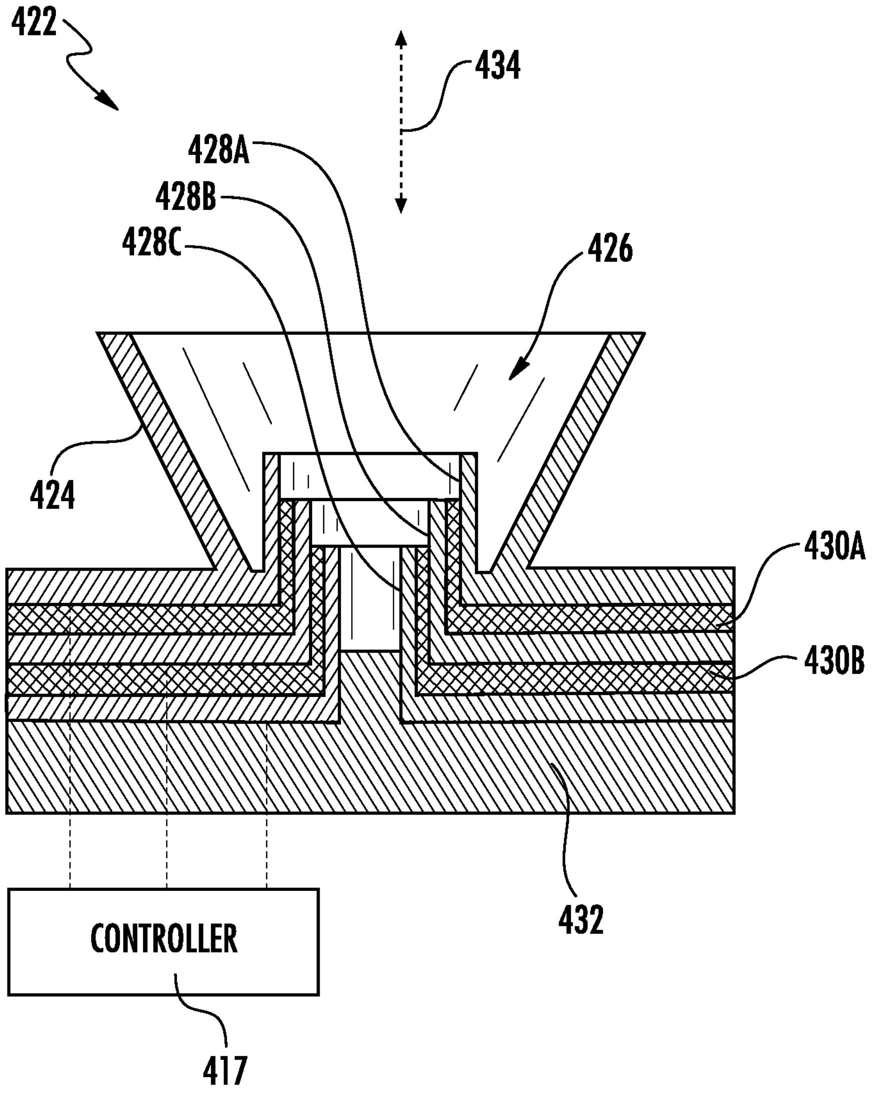
Figure 47:
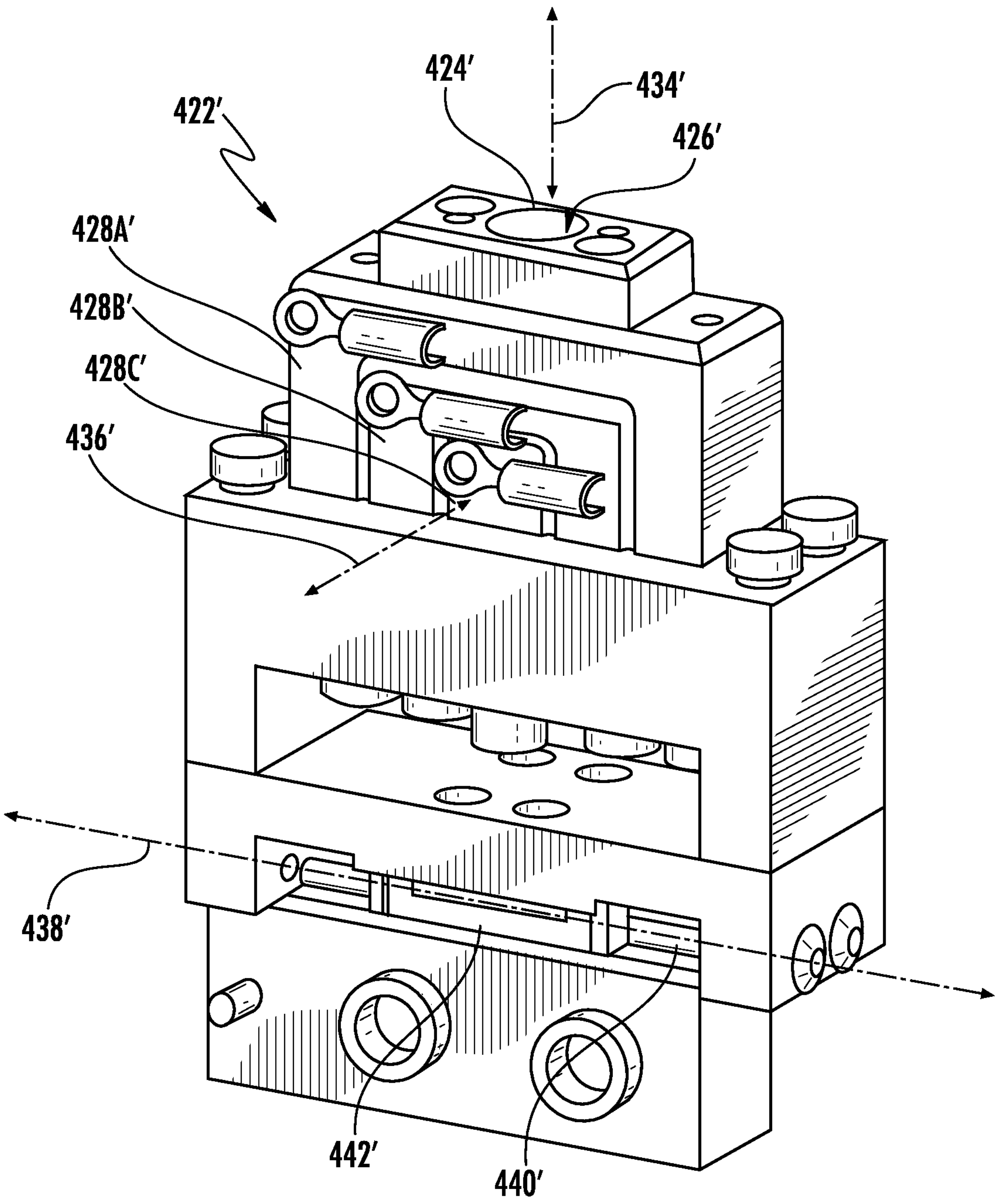
Figure 48:
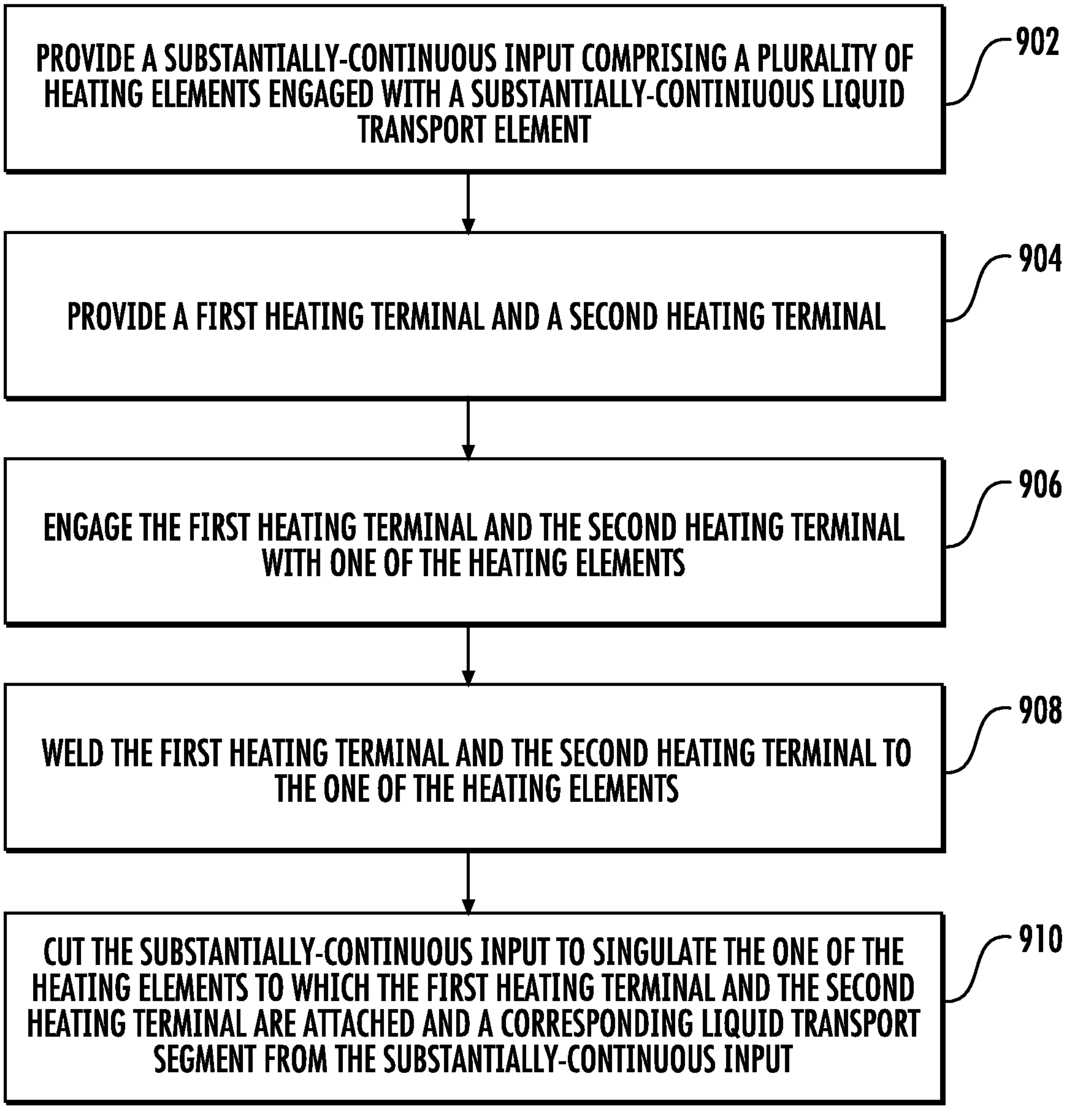
Figure 49:
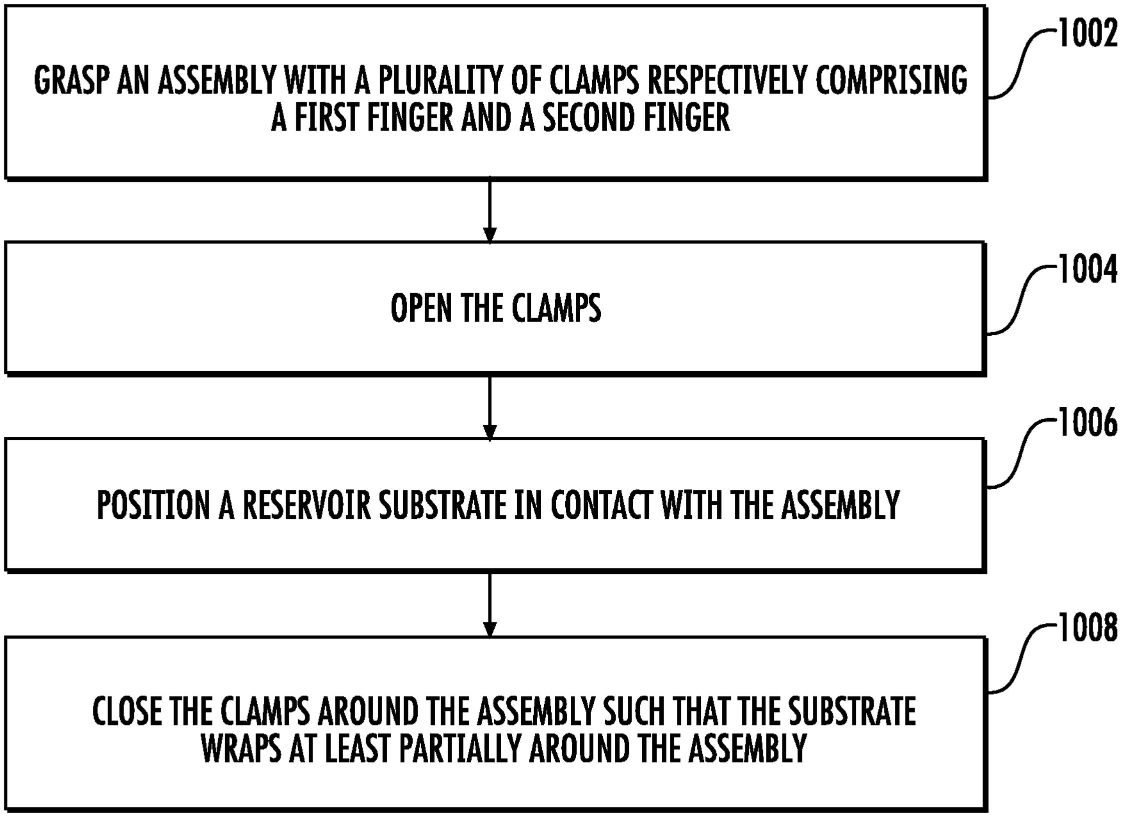
Figure 50:
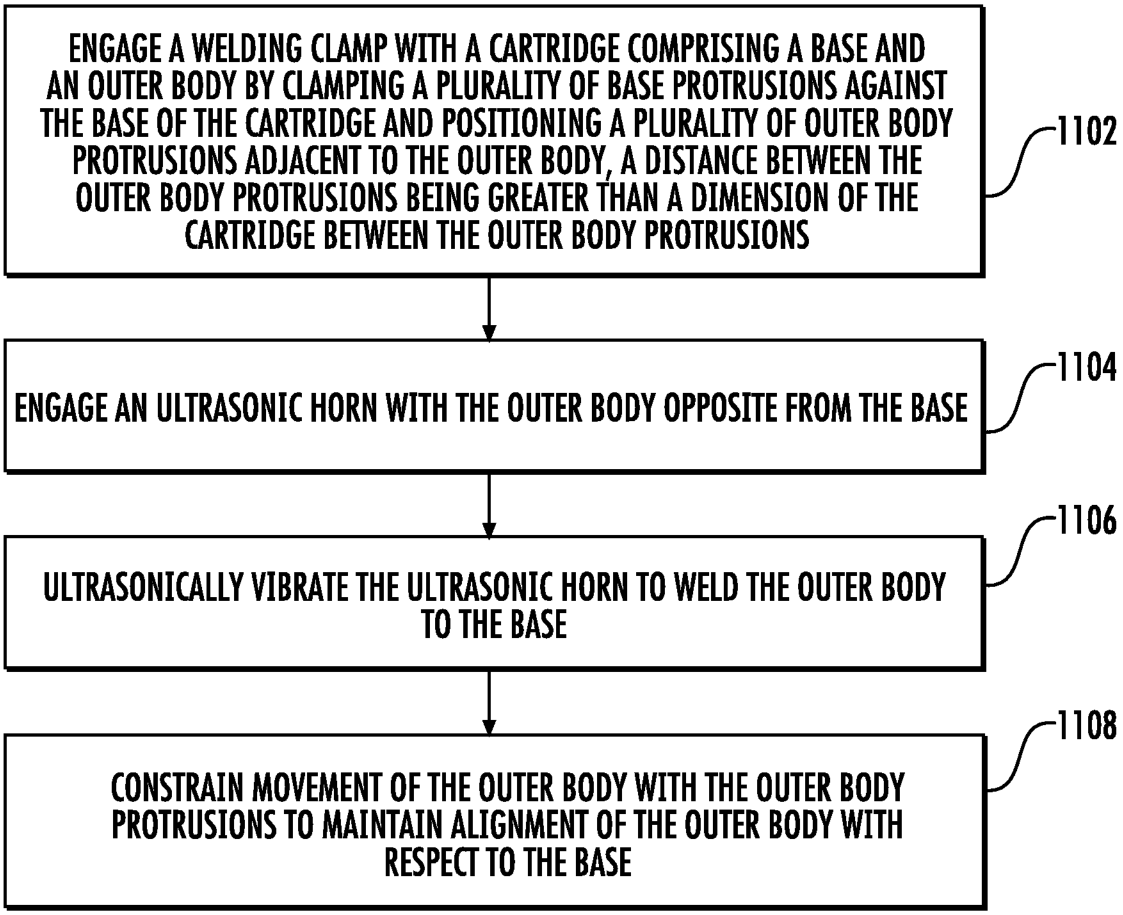
Figure 51:
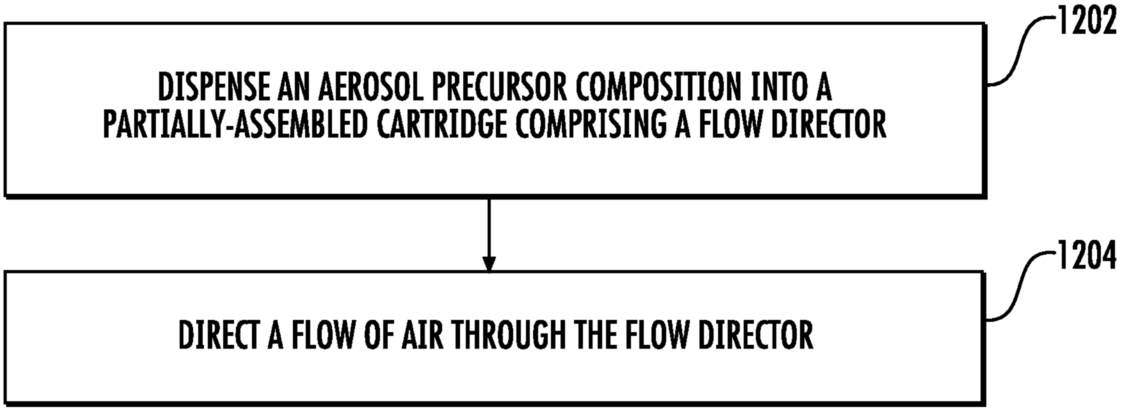
Figure 53:
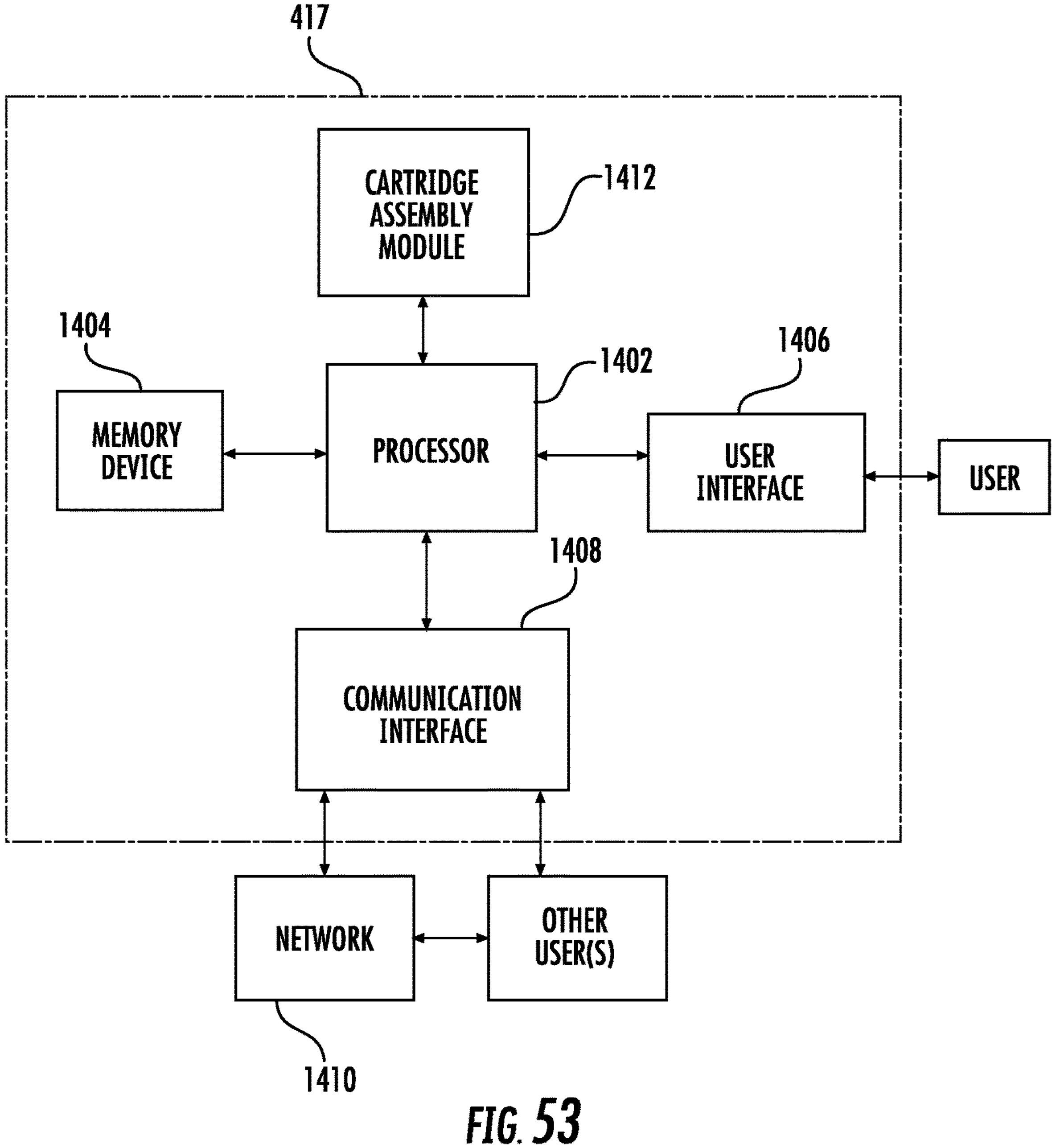

Having thus described the disclosure in the foregoing general terms, reference will now be made to the accompanying drawings, which are not necessarily drawn to scale, and wherein:

FIG. 1 illustrates an aerosol delivery device comprising a cartridge and a control body in an assembled configuration according to an example embodiment of the present disclosure;

FIG. 2 illustrates the control body of FIG. 1 in an exploded configuration according to an example embodiment of the present disclosure;

FIG. 3 illustrates the cartridge of FIG. 1 in an exploded configuration according to an example embodiment of the present disclosure;

FIG. 4 schematically illustrates a system for producing cartridges for an aerosol delivery device including a cartridge assembly subsystem, a cartridge filling subsystem, a cartridge capping subsystem, a cartridge labeling subsystem, and an inspection subsystem according to an example embodiment of the present disclosure;

FIG. 5 schematically illustrates an embodiment of the system of FIG. 4 further including a packaging subsystem according to an example embodiment of the present disclosure;

FIG. 6 illustrates a top view of an assembly carriage configured for usage at first and seventh assembly cells of the system of FIG. 5 according to an example embodiment of the present disclosure;

FIG. 7 illustrates a perspective view of an assembly carriage configured for usage at second and third assembly cells of the system of FIG. 5 according to an example embodiment of the present disclosure;

FIG. 8 illustrates a top view of the assembly carriage of FIG. 7 when a partially-assembled cartridge is received therein according to an example embodiment of the present disclosure;

FIG. 9 illustrates a perspective view of an assembly carriage configured for usage at fourth and fifth assembly cells of the system of FIG. 5 according to an example embodiment of the present disclosure;

FIG. 10 illustrates a top view of the assembly carriage of FIG. 9 according to an example embodiment of the present disclosure;

FIG. 11 illustrates a perspective view of the assembly carriage of FIG. 9 including a reservoir substrate received therein according to an example embodiment of the present disclosure;

FIG. 12 illustrates a folding apparatus configured to fold an atomizer according to an example embodiment of the present disclosure;

FIG. 13 illustrates a top view of the assembly carriage of FIG. 9 including a partially-assembled cartridge received therein according to an example embodiment of the present disclosure;

FIG. 14 schematically illustrates a partial front view of the partially-assembled cartridge in the assembly carriage of FIG. 9 and an end effector according to an example embodiment of the present disclosure;

FIG. 15 illustrates a top view of an assembly carriage configured for usage at a sixth assembly cell of the system of FIG. 5 according to an example embodiment of the present disclosure;

FIG. 16 schematically illustrates a method for assembling a plurality of cartridges for an aerosol delivery device according to an example embodiment of the present disclosure;

FIG. 17 schematically illustrates a method for assembling a cartridge for an aerosol delivery device according to an example embodiment of the present disclosure;

FIG. 18 schematically illustrates a second embodiment of the system of FIG. 4 further including a packaging subsystem according to the present disclosure;

FIG. 19 illustrates a sectional view through a welding fixture at a first assembly cell of the system of FIG. 18 according to an example embodiment of the present disclosure;

FIG. 20 illustrates a perspective view of an anti-static apparatus at the first assembly cell of the system of FIG. 18 according to an example embodiment of the present disclosure;

FIG. 21 illustrates a perspective view of a pneumatic inter-cell transporter positioned between the first assembly cell and a second assembly cell of the system of FIG. 18 according to an example embodiment of the present disclosure;

FIG. 22 illustrates a perspective view of the second assembly cell of the system of FIG. FIG. 18 according to an example embodiment of the present disclosure;

FIG. 23 illustrates an enlarged, partial perspective view of the second assembly cell of the system of FIG. 18 wherein a welder thereof is not shown according to an example embodiment of the present disclosure;

FIG. 24 illustrates an enlarged, partial perspective view of an input feeder and an assembly feeder of the second assembly cell of the system of FIG. 18 according to an example embodiment of the present disclosure;

FIG. 25 illustrates an enlarged, partial perspective view of multiple input feeders and multiple assembly feeders of the second assembly cell of the system of FIG. 18 according to an example embodiment of the present disclosure;

FIG. 26 illustrates an enlarged, partial view of a platform engaged with a rotary track at the third assembly cell of the system of FIG. 18 according to an example embodiment of the present disclosure;

FIG. 27 schematically illustrates a top view of an assembly gripper of the third assembly cell of the system of FIG. 18 wherein clamps of the assembly gripper are in an open configuration in order to receive a partially-assembled cartridge according to an example embodiment of the present disclosure;

FIG. 28 schematically illustrates a front view of the assembly gripper of FIG. 27 during sequential opening of the clamps thereof during insertion of an actuator pin in order to receive a partially-assembled cartridge according to an example embodiment;

FIG. 29 schematically illustrates a front view of the assembly gripper of FIG. 27 when the actuator pin is fully inserted and an assembly clamp is extending downwardly in order to receive a partially-assembled cartridge in the assembly gripper according to an example embodiment of the present disclosure;

FIG. 30 schematically illustrates a front view of the assembly gripper of FIG. 27 when the actuator pin is fully inserted and the assembly clamp is retracting after a partially-assembled cartridge is received in the assembly gripper according to an example embodiment of the present disclosure;

FIG. 31 schematically illustrates a front view of the assembly gripper of FIG. 27 during sequential closing of the clamps on a partially-assembled cartridge received in the assembly gripper during retraction of the actuator pin according to an example embodiment of the present disclosure;

FIG. 32 schematically illustrates a top view of the assembly gripper of the third assembly cell of the system of FIG. 18 wherein clamps of the assembly gripper are in a closed configuration after receipt of a partially-assembled cartridge according to an example embodiment of the present disclosure;

FIG. 33 schematically illustrates a bottom view of the assembly gripper of the third assembly cell of the system of FIG. 18 wherein clamps of the assembly gripper are in an open configuration prior to receipt of a reservoir substrate according to an example embodiment of the present disclosure;

FIG. 34 schematically illustrates a front view of the assembly gripper of the third assembly cell of the system of FIG. 18 wherein clamps of the assembly gripper are in an open configuration and a cap is engaging the partially-assembled cartridge according to an example embodiment of the present disclosure;

FIG. 35 schematically illustrates a bottom view of the assembly gripper of the third assembly cell of the system of FIG. 18 wherein clamps of the assembly gripper are in an open configuration and a substrate gripper is wrapping the reservoir substrate about the partially-assembled cartridge according to an example embodiment of the present disclosure;

FIG. 36 schematically illustrates a side view of the assembly gripper of the third assembly cell of the system of FIG. 18 wherein the cap is disengaged from the partially-assembled cartridge and retracting according to an example embodiment of the present disclosure;

FIG. 37 schematically illustrates a bottom view of the assembly gripper of the third assembly cell of the system of FIG. 18 wherein clamps of the assembly gripper are in a closed configuration and the assembly gripper and the substrate gripper engage the reservoir substrate of the partially-assembled cartridge according to an example embodiment of the present disclosure;

FIG. 38 schematically illustrates a bottom view of the assembly gripper of the third assembly cell of the system of FIG. 18 wherein clamps of the assembly gripper are in a closed configuration and engaging the reservoir substrate of the partially-assembled cartridge and the substrate gripper is retracting therefrom according to an example embodiment of the present disclosure;

FIG. 39 schematically illustrates a side view of the assembly gripper and an outer body coupling apparatus during coupling of an outer body to the partially-assembled cartridge according to an example embodiment of the present disclosure;

FIG. 40 illustrates a perspective view of a welding horn and welding clamp of the third assembly cell of the system of FIG. 18 according to an example embodiment of the present disclosure;

FIG. 41 illustrates a perspective view of a first cartridge gripper of the welding clamp of FIG. 40 according to an example embodiment of the present disclosure;

FIG. 42 illustrates a perspective view of a second cartridge gripper of the welding clamp of FIG. 40 according to an example embodiment of the present disclosure;

FIG. 43 illustrates a perspective view of a cartridge filling subsystem of the system of FIG. 18 according to an example embodiment of the present disclosure;

FIG. 44 illustrates an enlarged, partial view of an assembly carriage of the cartridge filling subsystem of FIG. 43 according to an example embodiment of the present disclosure;

FIG. 45 illustrates an embodiment of the cartridge filling subsystem of FIG. 43 including multiple manifolds according to an example embodiment of the present disclosure;

FIG. 46 illustrates a sectional view through a test fixture including a compliant member according to an example embodiment of the present disclosure;

FIG. 47 illustrates a perspective view of a test fixture including independently moveable electrical contacts according to an example embodiment of the present disclosure;

FIG. 48 schematically illustrates an aerosol delivery device assembly method according to an example embodiment of the present disclosure;

FIG. 49 schematically illustrates an additional aerosol delivery device assembly method according to an example embodiment of the present disclosure;

FIG. 50 schematically illustrates an aerosol delivery device ultrasonic welding method according to an example embodiment of the present disclosure;

FIG. 51 schematically illustrates an aerosol delivery device cartridge filling method according to an example embodiment of the present disclosure;

FIG. 52 schematically illustrates an aerosol delivery device test method according to an example embodiment of the present disclosure; and FIG. 53 schematically illustrates a controller according to an example embodiment of the present disclosure.

DETAILED DESCRIPTION OF PREFERRED EMBODIMENTS

The present disclosure will now be described more fully hereinafter with reference to exemplary embodiments thereof. These exemplary embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

The present disclosure provides descriptions of systems for assembling aerosol delivery devices. The aerosol delivery devices may use electrical energy to heat a material (preferably without combusting the material to any significant degree) to form an inhalable substance; such articles most preferably being sufficiently compact to be considered "hand-held" devices. An aerosol delivery device may provide some or all of the sensations (e.g., inhalation and exhalation rituals, types of tastes or flavors, organoleptic effects, physical feel, use rituals, visual cues such as those provided by visible aerosol, and the like) of smoking a cigarette, cigar, or pipe, without any substantial degree of combustion of any component of that article or device. The aerosol delivery device may not produce smoke in the sense of the aerosol resulting from by-products of combustion or pyrolysis of tobacco, but rather, that the article or device most preferably yields vapors (including vapors within aerosols that can be considered to be visible aerosols that might be considered to be described as smoke-like) resulting from volatilization or vaporization of certain components of the article or device, although in other embodiments the aerosol may not be visible. In highly preferred embodiments, aerosol delivery devices may incorporate tobacco and/or components derived from tobacco. As such, the aerosol delivery device can be characterized as an electronic smoking article such as an electronic cigarette or "e-cigarette."

While the systems are generally described herein in terms of embodiments associated with aerosol delivery devices such as so-called "e-cigarettes," it should be understood that the mechanisms, components, features, and methods may be embodied in many different forms and associated with a variety of articles. For example, the description provided herein may be employed in conjunction with embodiments of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of embodiments relating to aerosol delivery mechanisms by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Smoking articles of the present disclosure generally include a number of components provided within an outer shell or body. The overall design of the outer shell or body can vary, and the format or configuration of the outer body that can define the overall size and shape of the smoking article can vary. Typically, an elongated body resembling the shape of a cigarette or cigar can be a formed from a single, unitary shell; or the elongated body can be formed of two or more separable pieces. For example, a smoking article can comprise an elongated shell or body that can be substantially tubular in shape and, as such, resemble the shape of a conventional cigarette or cigar. However, various other shapes and configurations may be employed in other embodiments (e.g., rectangular or fob-shaped).

In one embodiment, all of the components of the smoking article are contained within one outer body or shell. Alternatively, a smoking article can comprise two or more shells that are joined and are separable. For example, a smoking article can possess at one end a control body comprising a shell containing one or more reusable components (e.g., a rechargeable battery and various electronics for controlling the operation of that article), and at the other end and removably attached thereto a shell containing a disposable portion (e.g., a disposable flavor-containing cartridge). More specific formats, configurations and arrangements of components within the single shell type of unit or within a multi-piece separable shell type of unit will be evident in light of the further disclosure provided herein. Additionally, various smoking article designs and component arrangements can be appreciated upon consideration of the commercially available electronic smoking articles.

Aerosol delivery devices of the present disclosure most preferably comprise some combination of a power source (i.e., an electrical power source), at least one control component (e.g., means for actuating, controlling, regulating and/or ceasing power for heat generation, such as by controlling electrical current flow from the power source to other components of the aerosol delivery device), a heater or heat generation component (e.g., an electrical resistance heating element or component commonly referred to as part of an "atomizer"), and an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined air flow path through the article such that aerosol generated can be withdrawn therefrom upon draw).

Alignment of the components within the aerosol delivery device of the present disclosure can vary. In specific embodiments, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery or other electrical power source (e.g., a capacitor) to provide current flow sufficient to provide various functionalities to the aerosol delivery device, such as powering of a heater, powering of control systems, powering of indicators, and the like. The power source can take on various embodiments. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery device of the present disclosure will be evident in light of the further disclosure provided hereinafter. Additionally, the selection of various aerosol delivery device components can be appreciated upon consideration of the commercially available electronic aerosol delivery devices. Further, the arrangement of the components within the aerosol delivery device can also be appreciated upon consideration of the commercially available electronic aerosol delivery devices.

One example embodiment of an aerosol delivery device 100 is illustrated in FIG. 1. In particular, FIG. 1 illustrates an aerosol delivery device 100 including a control body 200 and a cartridge 300. The control body 200 and the cartridge 300 can be permanently or detachably aligned in a functioning relationship. Various mechanisms may connect the cartridge 300 to the control body 200 to result in a threaded engagement, a press-fit engagement, an interference fit, a magnetic engagement, or the like. The aerosol delivery device 100 may be substantially rod-like, substantially tubular shaped, or substantially cylindrically shaped in some embodiments when the cartridge 300 and the control body 200 are in an assembled configuration. However, as noted above, various other configurations such as rectangular or fob-shaped may be employed in other embodiments.

In specific embodiments, one or both of the cartridge 300 and the control body 200 may be referred to as being disposable or as being reusable. For example, the control body 200 may have a replaceable battery or a rechargeable battery and/or capacitor and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments the cartridge 300 may comprise a single-use cartridge, as disclosed in U.S. Pat. No. 8,910,639 to Chang et al., which is incorporated herein by reference in its entirety.

FIG. 2 illustrates an exploded view of the control body 200 of the aerosol delivery device 100 according to an example embodiment of the present disclosure. As illustrated, the control body 200 may comprise a coupler 202, an outer body 204, a sealing member 206, an adhesive member 208 (e.g., KAPTON® tape), a flow sensor 210 (e.g., a puff sensor or pressure switch), a control component 212, a spacer 214, an electrical power source 216 (e.g., a battery, which may be rechargeable), a circuit board with an indicator 218 (e.g., a light emitting diode (LED)), a connector circuit 220, and an end cap 222. Examples of electrical power sources are described in U.S. Pat. App. Pub. No. 2010/0028766 by Peckerar et al., the disclosure of which is incorporated herein by reference in its entirety.

With respect to the flow sensor 210, representative current regulating components and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference also is made to the control schemes described in U.S. App. Pub. No. 2014/0270727 to Ampolini et al., which is incorporated herein by reference in its entirety.

In one embodiment the indicator 218 may comprise one or more light emitting diodes. The indicator 218 can be in communication with the control component 212 through the connector circuit 220 and be illuminated, for example, during a user drawing on a cartridge coupled to the coupler 202, as detected by the flow sensor 210. The end cap 222 may be adapted to make visible the illumination provided thereunder by the indicator 218. Accordingly, the indicator 218 may be illuminated during use of the aerosol delivery device 100 to simulate the lit end of a smoking article. However, in other embodiments the indicator 218 can be provided in varying numbers and can take on different shapes and can even be an opening in the outer body (such as for release of sound when such indicators are present).

Still further components can be utilized in the aerosol delivery device of the present disclosure. For example, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and WO 2010/003480 by Flick discloses a fluid flow sensing system indicative of a puff in an aerosol generating system; all of the foregoing disclosures being incorporated herein by reference in their entireties. Further examples of components related to electronic aerosol delivery articles and disclosing materials or components that may be used in the present article include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; and U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; WO 2010/091593 to Hon; and WO 2013/089551 to Foo, each of which is incorporated herein by reference in its entirety. A variety of the materials disclosed by the foregoing documents may be incorporated into the present devices in various embodiments, and all of the foregoing disclosures are incorporated herein by reference in their entireties.

FIG. 3 illustrates the cartridge 300 in an exploded configuration. As illustrated, the cartridge 300 may comprise a base 302, a control component terminal 304, an electronic control component 306, a flow director 308, an atomizer 310, a reservoir substrate 312, an outer body 314, a mouthpiece 316, a label 318, and first and second heating terminals 320*a*, 320*b* according to an example embodiment of the present disclosure.

In some embodiments the first and second heating terminals 320*a*, 320*b* may be embedded in, or otherwise coupled to, the flow director 308. For example, the first and second heating terminals 320*a*, 320*b* may be insert molded in the flow director 308. Accordingly, the flow director 308 and the first and second heating terminals are collectively referred to herein as a flow director assembly 322. Additional description with respect to the first and second heating terminals 320*a*, 320*b* and the flow director 308 is provided in U.S. Pat. Pub. No. 2015/0335071 to Brinkley et al., which is incorporated herein by reference in its entirety.

The atomizer 310 may comprise a liquid transport element 324 and a heating element 326. The cartridge may additionally include a base shipping plug engaged with the base and/or a mouthpiece shipping plug engaged with the mouthpiece in order to protect the base and the mouthpiece and prevent entry of contaminants therein prior to use as disclosed, for example, in U.S. Pat. No. 9,220,302 to Depiano et al., which is incorporated herein by reference in its entirety.

The base 302 may be coupled to a first end of the outer body 314 and the mouthpiece 316 may be coupled to an opposing second end of the outer body to substantially or fully enclose other components of the cartridge 300 therein. For example, the control component terminal 304, the electronic control component 306, the flow director 308, the atomizer 310, and the reservoir substrate 312 may be substantially or entirely retained within the outer body 314. The label 318 may at least partially surround the outer body 314, and optionally the base 302, and include information such as a product identifier thereon. The base 302 may be configured to engage the coupler 202 of the control body 200 (see, e.g., FIG. 2). In some embodiments the base 302 may comprise anti-rotation features that substantially prevent relative rotation between the cartridge and the control body as disclosed in U.S. Pat. App. Pub. No. 2014/0261495 to Novak et al., which is incorporated herein by reference in its entirety.

The reservoir substrate 312 may be configured to hold an aerosol precursor composition. Representative types of aerosol precursor components and formulations are also set forth and characterized in U.S. Pat. No. 7,726,320 to Robinson et al. and U.S. Pat. No. 8,881,737 to Collett et al., and U.S. Pat. Pub. Nos. 2013/0008457 to Zheng et al.; 2013/0213417 to Chong et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC. Embodiments of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; and U.S. Pat. No. 8,627,828 to Strickland et al.; as well as US Pat. Pub. Nos. 2010/0018539 to Brinkley et al. and 2010/0170522 to Sun et al.; and PCT WO 97/06786 to Johnson et al., all of which are incorporated by reference herein.

The reservoir substrate 312 may comprise a plurality of layers of nonwoven fibers formed into the shape of a tube encircling the interior of the outer body 314 of the cartridge 300. Thus, liquid components, for example, can be sorptively retained by the reservoir substrate 312. The reservoir substrate 312 is in fluid connection with the liquid transport element 324. Thus, the liquid transport element 324 may be configured to transport liquid from the reservoir substrate 312 to the heating element 326 via capillary action or other liquid transport mechanisms.

As illustrated, the liquid transport element 324 may be in direct contact with the heating element 326. As further illustrated in FIG. 3, the heating element 326 may comprise a wire defining a plurality of coils wound about the liquid transport element 324. In some embodiments the heating element 326 may be formed by winding the wire about the liquid transport element 324 as described in U.S. Pat. No. 9,210,738 to Ward et al., which is incorporated herein by reference in its entirety. Further, in some embodiments the wire may define a variable coil spacing, as described in U.S. Pat. App. Pub. No. 2014/0270730 to DePiano et al., which is incorporated herein by reference in its entirety. Various embodiments of materials configured to produce heat when electrical current is applied therethrough may be employed to form the heating element 326. Example materials from which the wire coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials; and ceramic (e.g., a positive or negative temperature coefficient ceramic).

However, various other embodiments of methods may be employed to form the heating element 326, and various other embodiments of heating elements may be employed in the atomizer 310. For example, a stamped heating element may be employed in the atomizer, as described in U.S. Pat. App. Pub. No. 2014/0270729 to DePiano et al., which is incorporated herein by reference in its entirety. Further to the above, additional representative heating elements and materials for use therein are described in U.S. Pat. No. 5,060,671 to Counts et al.; U.S. Pat. No. 5,093,894 to Deevi et al.; U.S. Pat. No. 5,224,498 to Deevi et al.; U.S. Pat. No. 5,228,460 to Sprinkel Jr., et al.; U.S. Pat. No. 5,322,075 to Deevi et al.; U.S. Pat. No. 5,353,813 to Deevi et al.; U.S. Pat. No. 5,468,936 to Deevi et al.; U.S. Pat. No. 5,498,850 to Das; U.S. Pat. No. 5,659,656 to Das; U.S. Pat. No. 5,498,855 to Deevi et al.; U.S. Pat. No. 5,530,225 to Hajaligol; U.S. Pat. No. 5,665,262 to Hajaligol; U.S. Pat. No. 5,573,692 to Das et al.; and U.S. Pat. No. 5,591,368 to Fleischhauer et al., the disclosures of which are incorporated herein by reference in their entireties. Further, chemical heating may be employed in other embodiments. Various additional examples of heaters and materials employed to form heaters are described in U.S. Pat. No. 8,881,737 to Collett et al., which is incorporated herein by reference, as noted above.

A variety of heater components may be used in the present aerosol delivery device. In various embodiments, one or more microheaters or like solid state heaters may be used. Microheaters and atomizers incorporating microheaters suitable for use in the presently disclosed devices are described in U.S. Pat. No. 8,881,737 to Collett et al., which is incorporated herein by reference in its entirety.

The first heating terminal 320*a* and the second heating terminal 320*b* (e.g., negative and positive heating terminals) are configured to engage opposing ends of the heating element 326 and to form an electrical connection with the control body 200 (see, e.g., FIG. 2) when the cartridge 300 is connected thereto. Further, when the control body 200 is coupled to the cartridge 300, the electronic control component 306 may form an electrical connection with the control body through the control component terminal 304. The control body 200 may thus employ the electronic control component 212 (see, FIG. 2) to determine whether the cartridge 300 is genuine and/or perform other functions. Further, various examples of electronic control components and functions performed thereby are described in U.S. Pat. App. Pub. No. 2014/0096781 to Sears et al., which is incorporated herein by reference in its entirety.

During use, a user may draw on the mouthpiece 316 of the cartridge 300 of the aerosol delivery device 100 (see, FIG.

1). This may pull air through an opening in the control body 200 (see, e.g., FIG. 2) or in the cartridge 300. For example, in one embodiment an opening may be defined between the coupler 202 and the outer body 204 of the control body 200 (see, e.g., FIG. 2), as described in U.S. Pat. No. 9,220,302 to DePiano et al., which is incorporated herein by reference in its entirety. However, the flow of air may be received through other parts of the aerosol delivery device 100 in other embodiments. As noted above, in some embodiments the cartridge 300 may include the flow director 308. The flow director 308 may be configured to direct the flow of air received from the control body 200 to the heating element 326 of the atomizer 310.

A sensor in the aerosol delivery device 100 (e.g., the flow sensor 210 in the control body 200) may sense the puff. When the puff is sensed, the control body 200 may direct current to the heating element 326 through a circuit including the first heating terminal 320*a* and the second heating terminal 320*b*. Accordingly, the heating element 326 may vaporize the aerosol precursor composition directed to an aerosolization zone from the reservoir substrate 312 by the liquid transport element 324. Thus, the mouthpiece 326 may allow passage of air and entrained vapor (i.e., the components of the aerosol precursor composition in an inhalable form) from the cartridge 300 to a consumer drawing thereon.

Various other details with respect to the components that may be included in the cartridge 300 are provided, for example, in U.S. Pat. App. Pub. No. 2014/0261495 to DePiano et al., which is incorporated herein by reference in its entirety. In this regard, FIG. 7 thereof illustrates an enlarged exploded view of a base and a control component terminal; FIG. 8 thereof illustrates an enlarged perspective view of the base and the control component terminal in an assembled configuration; FIG. 9 thereof illustrates an enlarged perspective view of the base, the control component terminal, an electronic control component, and heating terminals in an assembled configuration; FIG. 10 thereof illustrates an enlarged perspective view of the base, the atomizer, and the control component in an assembled configuration; FIG. 11 thereof illustrates an opposing perspective view of the assembly of FIG. 10 thereof; FIG. 12 thereof illustrates an enlarged perspective view of the base, the atomizer, the flow director, and the reservoir substrate in an assembled configuration; FIG. 13 thereof illustrates a perspective view of the base and an outer body in an assembled configuration; FIG. 14 thereof illustrates a perspective view of a cartridge in an assembled configuration; FIG. 15 thereof illustrates a first partial perspective view of the cartridge of FIG. 14 thereof and a coupler for a control body; FIG. 16 thereof illustrates an opposing second partial perspective view of the cartridge of FIG. 14 thereof and the coupler of FIG. 15 thereof; FIG. 17 thereof illustrates a perspective view of a cartridge including a base with an anti-rotation mechanism; FIG. 18 thereof illustrates a perspective view of a control body including a coupler with an anti-rotation mechanism; FIG. 19 thereof illustrates alignment of the cartridge of FIG. 17 with the control body of FIG. 18; FIG. 20 thereof illustrates an aerosol delivery device comprising the cartridge of FIG. 17 thereof and the control body of FIG. 18 thereof with a modified view through the aerosol delivery device illustrating the engagement of the anti-rotation mechanism of the cartridge with the anti-rotation mechanism of the connector body; FIG. 21 thereof illustrates a perspective view of a base with an anti-rotation mechanism; FIG. 22 thereof illustrates a perspective view of a coupler with an anti-rotation mechanism; and FIG. 23 thereof illustrates a sectional view through the base of FIG. 21 thereof and the coupler of FIG. 22 thereof in an engaged configuration. Various other details with respect to the components that may be included in the cartridge 300 are provided, for example, in U.S. Pat. Pub. No. 2015/0335071 to Brinkley et al., filed May 23, 2014, which is incorporated herein by reference in its entirety.

Various components of an aerosol delivery device according to the present disclosure can be chosen from components described in the art and commercially available. Reference is made for example to the reservoir and heater system for controllable delivery of multiple aerosolizable materials in an electronic smoking article disclosed in U.S. Pat. App. Pub. No. 2014/0000638 to Sebastian et al., which is incorporated herein by reference in its entirety.

In another embodiment substantially the entirety of the cartridge may be formed from one or more carbon materials, which may provide advantages in terms of biodegradability and absence of wires. In this regard, the heating element may comprise carbon foam, the reservoir substrate may comprise carbonized fabric, and graphite may be employed to form an electrical connection with the power source and control component. An example embodiment of a carbon-based cartridge is provided in U.S. Pat. App. Pub. No. 2013/0255702 to Griffith et al., which is incorporated herein by reference in its entirety.

As described above, cartridges of aerosol delivery devices may include a number of components. Some of the components may be relatively small and/or relatively delicate. Accordingly, precise manufacturing techniques may be required to form the aerosol delivery devices. In this regard, aerosol delivery devices have traditionally been formed via manual assembly by humans.

However, use of manual labor to assemble aerosol delivery devices suffers from certain detriments. In this regard, the quality of aerosol delivery devices produced via manual labor is only as good as the workers performing the labor. Further, even skilled workers may make errors from time-to-time. Additionally, manual labor may be relatively costly. Thus, as result of these issues and other issues associated with the production of aerosol delivery devices via manual labor, it may be desirable to produce aerosol delivery devices in an automated manner. Accordingly, automated production of cartridges for aerosol delivery devices is discussed hereinafter, which may provide enhanced repeatability, lower costs, and/or avoid other issues noted above.

In this regard, FIG. 4 schematically illustrates an embodiment of a system 400 for assembling cartridges (e.g., the above-described cartridges 300) for an aerosol delivery device (e.g., the above-described aerosol delivery device 100). Note that the above-described aerosol delivery device 100 is provided by way of example. In this regard, the methods, systems, and apparatuses described herein may be employed to form various embodiments of cartridges that differ from the above described cartridges in one or more respects.

As illustrated, the system 400 may include various subsystems that perform particular functions in the formation of the completed cartridges 300. Note that although the subsystems are illustrated as being separate from one another, the subsystems may overlap. For example, in some embodiments common equipment may perform two or more functions (e.g., assembly and filling or capping and labeling, etc.), rather than the particular functions being performed by separate equipment.

Further, the various subsystems and portions thereof may be separately usable. In this regard, although the subsystems and portions thereof are generally described herein as being usable together, this is by way of example. Accordingly, any of the subsystems or portions thereof described herein may be usable by themselves or in any combination with some or all of the other subsystems and portions thereof described herein, or used in combination with other systems. Example embodiments of other automated systems for assembling cartridges for aerosol delivery devices which may be employed in conjunction with the systems disclosed herein are disclosed in U.S. Pat. Pub. No. 2015/0223522 to Ampolini et al. and U.S. patent application Ser. No. 14/716,112 to Guenther et al., filed May 19, 2015, which are incorporated herein by reference in their entireties. Further, although particular embodiments of portions of the subsystems are disclosed hereinafter, these embodiments are provided for example purposes only. Accordingly, in some embodiments the subsystems may include fewer or additional portions. Thus, each portion of each subsystem, and each portion of the overall system is not required in all embodiments.

As illustrated, the subsystems may include a cartridge assembly subsystem 402 configured to form unfilled cartridges 404 from components 406 (e.g., the base 302, the first and second heating terminals 320*a*, 320*b* (see, e.g., FIG. 3), etc.). A cartridge filling subsystem 408 may fill the unfilled cartridges 404 to produce filled cartridges 410. A cartridge capping subsystem 412 may cap the filled cartridges 410 to produce capped cartridges 414. A cartridge labeling subsystem 416 may apply labels to the capped cartridges 414 to complete the cartridges 300.

The system 400 may additionally include an inspection subsystem 418. The inspection subsystem 418 may inspect the components 406, the unfilled cartridges 404, the filled cartridges 410, the capped cartridges 414, and/or the completed cartridges 300. Further, in some embodiments the cartridges may be inspected at intermediate states of completion at one or more of the cartridge assembly subsystem 402, the cartridge filling subsystem 408, the cartridge capping subsystem 412, and the cartridge labeling subsystem 416. Accordingly, the cartridges 300 and components thereof may be inspected before, during, and after completion thereof.

The system 400 may further include at least one controller 417. The controller 417 may be configured to control the cartridge assembly subsystem 402, the cartridge filling subsystem 408, the cartridge capping subsystem 412, and/or the cartridge labeling subsystem 416. In this regard, the controller 417 may be configured to receive data from one or more the sensors and output instructions based thereon, in addition to otherwise directing the operations described herein. Note that although a single controller is illustrated, in other embodiments the controller may include a plurality of controllers that control fewer than all of the functions and subsystems of the system, and which may or may not communicate with one another.

Note that some or all of the system 400 may be automated. In this regard, as described hereinafter, robotic apparatuses may be employed in some embodiments of the system 400. The robotic apparatuses may be provided from various robotic manufacturers including, by way of example, DENSO Robotics of Long Beach, Calif., FANUC of Rochester Hills, Mich., Mitsubishi Electric Automation of Vernon Hills, Ill., EPSON Robots of Carson, Calif., Siemens Automation Technology of Munich, Germany, Mikron Corporation of Denver, Colo., and ATC Automation of Cookeville, Tenn.

A more detailed illustration of an example embodiment of the system 400 of FIG. 4 is illustrated in FIG. 5. As illustrated, the system 400 may include the cartridge assembly subsystem 402, the cartridge filling subsystem 408, the cartridge capping subsystem 412, and the cartridge labeling subsystem 416. Further, the system 400 may include a packaging subsystem 420. The packaging subsystem 420 may be configured to package the completed cartridges 300. Note that although the controller 417 and the inspection subsystem 418 are not separately illustrated in FIG. 5, these components may additionally be included in the system 400 as described above with respect to FIG. 4.

As illustrated in FIG. 5, the subsystems 402, 408, 412, 416, 420 may respectively include one or more assembly cells 502*a-i* (collectively, "assembly cells 502"). An assembly cell, as used herein, refers to a group of robotic machinery configured to perform one or more tasks. For example, in the embodiment illustrated in FIG. 5, the cartridge assembly subsystem 402 is divided into five assembly cells 502*a-e*. Further, the cartridge filling subsystem 408, the cartridge capping subsystem 412, the cartridge labeling subsystem 416, and the packaging subsystem 420 each respectively comprise an assembly cell 502*f-i*.

Preferably, the system 400 may be configured to rapidly produce the cartridges 300 with minimal human interaction being required. In this regard, the assembly cells 502*a-i* may be collectively configured to assemble a plurality of cartridge components together and/or perform additional functions with respect to the cartridges 300. The system 400 may include certain features configured to improve the interaction between the assembly cells 502.

For example, the system 400 may include one or more assembly tracks 504*a-e* (collectively, "assembly tracks 504"). In the illustrated embodiment, a first assembly cell 502*a* includes an assembly track 504*a*, second and third assembly cells 502*b*, 502*c* share an assembly track 504*b*, fourth and fifth assembly cells 502*d*, 502*e* share an assembly track 504*c*, a sixth assembly cell 502*f* includes an assembly track 504*d*, and a seventh assembly cell 502*h* includes an assembly track 504*e*.

The assembly tracks 504 may be configured to circulate assembly carriages 506*a-e* (collectively, "assembly carriages 506") thereon. The circulating assembly carriages 506 may be configured to engage a plurality of assemblies comprising one or more cartridge components 300-326. The assemblies are also referred to as partially-assembled cartridges 300. Thereby, the cartridges 300 may be assembled by combining the cartridge components 300-326 generally in an additive manner.

As noted above, the assembly tracks 504 may circulate the assembly carriages 506. Thereby, the assembly carriages 506 may be reused in the formation of a plurality of the cartridges 300 by returning to an initial starting point on the assembly tracks 504 following the removal of one or more partially or fully assembled cartridges 300 therefrom. Accordingly, cartridge assembly operations may be iteratively repeated for additional cartridge components directed thereto after the offloading of the one or more partially or fully assembled cartridges 300 assembled thereon.

In some embodiments each of the assembly carriages 506 may be configured to receive cartridge components for a single cartridge 300. Thereby, each of the assembly carriages 506 may be employed to assemble components for an individual cartridge 300 during each cycle. However, in other embodiments the assembly carriages 506 may be configured to receive cartridge components for a plurality of cartridges 300. Thereby, each of the assembly carriages 506 may be employed to assemble a plurality of cartridges 300. In this regard, by engaging, transporting, and assembling a plurality of the partially-assembled cartridges 300 on one of the assembly carriages 506, the rate at which the cartridges are assembled may be increased.

In order to perform each of the assembly operations associated with producing the cartridges 300, the partially-assembled cartridges may be transported to each of the assembly cells 502. Accordingly, one option is to assemble each cartridge on a single assembly carriage, which may be transported amongst each of the assembly cells. However, the assembly operations performed by each of the assembly cells 502 and the cartridge components employed in the assembly operations may vary considerably. Accordingly, Applicants have determined that assembly of the cartridges 300 may beneficially occur with usage of a plurality of differing assembly carriages in the system 400. Accordingly, each track 504 may include one or more assembly carriages 506 associated therewith, and the assembly carriages associated with one track may differ from the assembly carriages associated with one or more of the other assembly tracks.

Accordingly, the system 400 may further comprise one or more transfer apparatuses 508*a-d* (collectively, "transfer apparatuses 508"). The transfer apparatuses 508 may be configured to transfer the partially-assembled cartridges 300 between a pair of the assembly cells 502. Thereby, the partially-assembled cartridges 300 may be transferred from the assembly carriage 506 at a first one of the cells 502 to a second one of the cells.

In order to transfer the partially-assembled cartridges 300, the transfer assemblies 508 may each include a transfer track 510*a-d* (collectively, "transfer tracks 510"). In some embodiments the partially-assembled cartridges 300 may be transported directly on the transfer track 510. In another embodiment the transfer assemblies 508 may respectively include one or more transfer carriages 512*a-d* (collectively, "transfer carriages 512") configured to engage partially-assembled cartridges 300, and the transfer carriages may transport the partially-assembled cartridges via movement of the transfer track 510. The transfer carriages 512 may circulate on the respective transfer tracks 508. Thereby, the transfer carriages 512 may be reused to transfer the partially-assembled cartridges 300 between the assembly cells 502.

Each transfer apparatus 508 may further comprise a first transfer member 514*a-d* (collectively, "first transfer members 514") configured to disengage the partially-assembled cartridges 300 from the assembly carriages 512 on an assembly track 504 of a first one of the pair of the assembly cells 502 and engage the partially-assembled cartridges with a respective one of the transfer carriages 512 on the transfer track 510. Further, each transfer apparatus 508 may comprise a second transfer member 516*a-d* (collectively, "second transfer members 516") configured to disengage the partially-assembled cartridges 300 from the transfer carriages 512 and engage the partially-assembled cartridges with one of the assembly carriages 506 of a second one of the pair of the assembly cells 502. The first and second transfer members 514, 516 may each comprise a robotic arm in some embodiments.

In one embodiment the transfer carriages 512 may be configured to engage and simultaneously transfer each of the partially-assembled cartridges 300 held by one of the assembly carriages 506. However, in another embodiment the transfer carriages 512 may be configured to engage a single one of the partially-assembled cartridges 300 at a time. Thereby, the transfer apparatuses 508 may individually and sequentially transfer the partially-assembled cartridges 300 between the pair of the assembly cells 504.

By sequentially transporting the partially-assembled cartridges 300, certain benefits may be provided. In this regard, the partially-assembled cartridges 300 may be inspected by the inspection subsystem 418 (see, FIG. 4) at each assembly cell 502. Further, some of the partially-assembled cartridges 300 may be removed from the system 400 to allow for further analysis thereof, for example, to ensure that the cartridges meet certain quality control standards. Accordingly, some of the partially-assembled cartridges 300 may be removed from the normal assembly flow during the production of the cartridges. As a result, some of the partially-assembled cartridges 300 may be removed from the assembly carriages 506 for inspection and/or disposal.

Thus, if the transfer carriages 512 were to be configured to hold the same number of partially-assembled carriages 300 as the assembly carriage 506 upstream thereof, the transfer carriages would in some instances include fewer partially-assembled cartridges than a capacity thereof. Accordingly, the transfer carriages 512 may be configured to hold fewer partially-assembled cartridges 300 than the assembly carriages 506 from which the partially-assembled cartridges are received. For example, as noted above, in one embodiment the transfer carriages 512 may be configured to engage a single one of the partially-assembled cartridges 300 at a time. Thereby, the second transfer member 516 may transfer the partially-assembled cartridges 300 to assembly carriages 506 at the downstream assembly cell 502. As a result of the partially-assembled cartridges 300 being transferred individually, the second transfer member 516 may continue engaging the partially-assembled carriages directed thereto until the assembly carriage 506 at the downstream assembly cell 502 is full, such that each assembly carriage is full.

By employing the transfer assemblies 508 to singulate the partially-assembled cartridges 300 in this manner, issues with respect to assembly carriages 506 transporting fewer partially-assembled cartridges than a capacity thereof may be avoided. In this regard, as noted above, the second transfer members 516 may engage partially-assembled cartridges with the assembly carriages 506 at the downstream assembly cell 502 until the capacity thereof is reached. In contrast, if the partially-assembled cartridges 300 were to be transported to each of the assembly cells on the same carriage throughout the assembly process, the removal of partially-assembled cartridges for inspection or quality control purposes would result in the carriages transporting fewer partially-assembled cartridges than the capacity thereof. Accordingly, usage of separate assembly tracks 504 and transfer tracks 510 may be desirable for this additional reason.

In some embodiments each assembly cell 502 may include a respective assembly track 504. In another embodiment some of the assembly cells 502 may share an assembly track. For example, in the embodiment illustrated in FIG. 5, the second and third assembly cells 502*b*, 502*c* share the assembly track 504*b*. Similarly, the fourth and fifth assembly cells 502*d*, 502*e* share the assembly track 504*c*. In this regard, the assembly operations performed at the assembly cells 502 sharing one of the assembly tracks 504 may be suitable for usage of the same assembly carriage 506 such that usage of separate assembly tracks may not be necessary.

Operation of the system 400 is described hereinafter. As may be understood, the operations described herein may be performed in various other orders and in various other manners. Further, it should be understood that the assembly operations performed will vary depending on the particular embodiment of the cartridge undergoing production. Although the system 400 is described herein as producing the cartridges 300 of FIG. 3, it should be understood that the system 400 could be employed to produce various other embodiments of cartridges.

At the first assembly cell 502*a*, the assembly carriage 506*a* on the assembly track 504*a* may receive a plurality of the bases 302. A vision system rotates the bases 302 to a desired orientation that may be maintained through some or all of the cartridge assembly process. The control component terminals 304 are engaged with the bases 302. The electronic control components 306 are engaged with the control component terminals 304. The electronic control components 306 may be programed through the control component terminals 304. The flow director assemblies 322 are engaged with the bases 302. The flow director assemblies 322 are welded or otherwise affixed to the bases 302 (e.g., via ultrasonic welding).

Defective partially-assembled cartridges 300 may be identified (e.g., by the inspection subsystem 418; see, FIG. 4) and removed. Samples of the partially-assembled cartridges 300 may also be removed for further quality control inspections. The remaining partially-assembled cartridges 300 may be unloaded and transported by the transfer assembly 508*a* to the second assembly cell 502*b*. The assembly carriage 506*a* at the first assembly cell 502*a* may be returned by the assembly track 504*a* to an initial starting point for production of additional cartridges 300.

At the second assembly cell 502*b*, the assembly carriage 506*b* on the assembly track 504*b* may receive the partially-assembled cartridges 300 from the transfer assembly 508*a*. The partially-assembled cartridges 300 received from the first assembly cell 502*a* may comprise the base 302, the control component terminal 304, the electronic control component 306, and the flow director assembly 322. A leak test may be performed by the inspection subsystem 418 (see, FIG. 4) to check for leaks between the flow director assemblies 322 and the bases 302. Atomizers 310 may be cut from a substantially-continuous input and the heating elements 326 (see, FIG. 3) of the atomizers may be welded (e.g., laser welded) to the first and second heating terminals 320*a*, 320*b* (see, FIG. 3) of the flow director assemblies 322. Example embodiments of apparatuses and methods for welding atomizers to heating terminals are provided in U.S. Pat. Pub. No. 2015/0223522 to Ampolini et al., and U.S. patent application Ser. No. 14/716,112 to Guenther et al., filed May 19, 2015, which are incorporated herein by reference in their entireties.

After welding, an electrical resistance between the first and second heating terminals 320*a*, 320*b* (see, FIG. 3) may be measured at the third assembly cell 502*c* and compared to an acceptable range of resistance by the inspection subsystem 418 (see, FIG. 4). Defective partially-assembled cartridges 300 identified by the inspection subsystem 418 may be removed. Samples of the partially-assembled cartridges 300 may also be removed for further quality control inspections. The remaining partially-assembled cartridges 300 may be unloaded from the assembly carriage 506*b* and transported by the transfer assembly 508*b* to the fourth assembly cell 502*d*. The assembly carriage 506*b* at the second assembly track 504*b* may be returned to an initial starting point for production of additional cartridges 300.

At the fourth assembly cell 502*d*, the assembly carriage 506*c* on the assembly track 504*c* may receive the partially-assembled cartridges 300 from the transfer assembly 508*b*. The partially-assembled cartridges 300 received from the third assembly cell 502*c* may comprise the base 302, the control component terminal 304, the electronic control component 306, the flow director assembly 322, and the atomizer 310. The liquid transport element 324 of the atomizer 310 may be folded against the first and second heating terminals 320*a*, 320*b* of the flow director assembly 322 (see, FIG. 3) at the fourth assembly cell 502*d*.

At the fifth assembly cell 502*e*, the reservoir substrates 312 may be cut from a substantially-continuous input and engaged with an assembly carriage 506*c*. The assembly track 504*c* may deliver the assembly carriage 506*c* to the fourth assembly cell 502*d*, at which the partially-assembled cartridges 300, with the liquid transport elements 324 folded against the flow director assemblies 322, may be engaged with the reservoir substrates 312 such that the reservoir substrates are at least partially wrapped around the flow director assemblies. Outer bodies 314 may then be engaged with the partially-assembled cartridges 300 by extending over the reservoir substrates 312 and into engagement with the flow director assemblies 322. The presence and position of the control component terminals 304 and the first and second heating terminals 320*a*, 320*b* (see, FIG. 3) may be checked by the inspection subsystem 418 (see, FIG. 4) at the fourth assembly cell 502*d*. Further, the outer bodies 314 may be affixed (e.g., ultrasonically welded) to the flow director assemblies 322 and/or the base 302.

At the fifth assembly cell 502*e*, the inspection subsystem 418 (see, FIG. 4) may test for leaks (e.g., between the outer bodies 314 and the flow director assemblies 322). Defective partially-assembled cartridges 300 identified by the inspection subsystem 418 may be removed. Samples of the partially-assembled cartridges 300 may also be removed for further quality control inspections. The remaining partially-assembled cartridges 300 may be unloaded from the assembly carriage 506*c* and transported by the transfer assembly 508*c* to the sixth assembly cell 502*f*. The assembly carriage 506*c* at the third assembly track 504*c* may be returned to an initial starting point for production of additional cartridges 300.

At the sixth assembly cell 502*f*, the assembly carriage 506*f* on the assembly track 504*d* may receive the partially-assembled cartridges 300 from the transfer assembly 508*c*. The partially-assembled cartridges 300 received from the fifth assembly cell 502*e* may comprise the base 302, the control component terminal 304, the electronic control component 306, the flow director assembly 322, the atomizer 310, the reservoir substrate 312, and the outer body 314. The sixth assembly cell 502*f* may fill the partially-assembled cartridges with an aerosol precursor composition 328. The partially-assembled cartridges 300 may be weighed before and after filling by the inspection subsystem 418 (see, FIG. 4) to ensure that a proper quantity of the aerosol precursor composition 328 is dispensed. Defective partially-assembled cartridges 300 identified by the inspection subsystem 418 may be removed. Samples of the partially-assembled cartridges 300 may also be removed for further quality control inspections. The remaining partially-assembled cartridges 300 may be unloaded from the assembly carriage 506*d* and transported by the transfer assembly 508*d* to the seventh assembly cell 502*g*. The assembly carriage 506*d* at the fourth assembly track 504*d* may be returned to an initial starting point for production of additional cartridges 300.

At the seventh assembly cell 502*g*, the assembly carriage 506*e* on the assembly track 504*e* may receive the partially-assembled cartridges 300 from the transfer assembly 508*d*. The partially-assembled cartridges 300 received from the third assembly cell 502*c* may comprise the base 302, the control component terminal 304, the electronic control component 306, the flow director assembly 322, the atomizer 310, the reservoir substrate 312, the outer body 314, and the aerosol precursor composition 328. The mouthpieces 316 may be engaged with the outer bodies 314 and affixed (e.g., ultrasonically welded) thereto at the seventh assembly cell 502*g*. In some embodiments the outer bodies 314 may be marked (e.g., laser marked) with a date code or other identifier at the seventh assembly cell 502*g*. Further, the identifiers may be inspected by the inspection subsystem 418 (see, FIG. 4) and the electronic control components 306 may be initialized. Defective partially-assembled cartridges 300 identified by the inspection subsystem 418 may be removed. Samples of the partially-assembled cartridges 300 may also be removed for further quality control inspections. The remaining partially-assembled cartridges 300 may be unloaded from the assembly carriage 506*e* and transported to the eighth assembly cell 502*h*. The assembly carriage 506*e* at the fifth assembly track 504*e* may be returned to an initial starting point for production of additional cartridges 300.

At the eight assembly cell 502*h*, the partially-assembled cartridges 300 received from the seventh assembly cell 502*g* may comprise the base 302, the control component terminal 304, the electronic control component 306, the flow director assembly 322, the atomizer 310, the reservoir substrate 312, the outer body 314, the aerosol precursor composition 328, and the mouthpiece 316. The label 318 may be applied to the outer bodies 314 to complete the cartridges at the eighth assembly cell 502*h*. Further, the completed cartridges 300 may be directed to the ninth assembly cell 502*i*, at which packaging 330 may be applied to the cartridges 300, such that the cartridges are ready for retail sale.

As noted above, the assembly cells 502 may include assembly carriages 506 that are particularly configured for the components received therein and assembly operations performed therewith. For example, FIG. 6 illustrates an embodiment of the assembly carriages 506*a*, 506*e* employed at the first assembly cell 502*a* and the seventh assembly cell 502*g*. As illustrated, the assembly carriage 506*a*, 506*e* may include one or more nests 602 respectively comprising a receptacle 604. In the illustrated embodiment the assembly carriage 506*a*, 506*e* includes four nests 602 each including the receptacle 604. The receptacles 604 may extend substantially vertically when the assembly carriages 506*a*, 506*e* are positioned on the assembly track 504*a*, 504*e* in a horizontal configuration. In this regard, assembly of the cartridges 300 at the first assembly cell 502*a* and the seventh assembly cell 502*e* may occur generally by vertically directing components downwardly into contact with one or more components received in the nests 602.

Further, FIG. 7 illustrates an embodiment of the assembly carriage 506*b* employed at the second and third assembly cells 502*b*, 502*c*. As illustrated, the assembly carriage 506*b* may include one or more first nests 606 and one or more second nests 608. The first nests 606 may be configured to receive the partially-assembled cartridges 300 in a first orientation, whereas the second nests 608 may be configured to receive the partially-assembled cartridge in a second orientation that differs from the first orientation.

In this regard, the first nest 606 may comprise a receptacle 610 configured to receive the base 302 (see, e.g., FIG. 3) of the partially-assembled cartridge 300 such that the partially-assembled cartridge defines a substantially vertical configuration when the assembly carriage 506*b* is positioned on the assembly track 504*b* in a horizontal configuration. Further, the second nest 608 may comprise a recess 612 configured to hold the partially-assembled cartridge 300 in a substantially horizontal configuration when the assembly carriage 506*b* is positioned on the assembly track 504*b* in a horizontal configuration. Thereby, the first nest 606 and the second nest 608 may be configured to hold the partially-assembled cartridges in configurations that are substantially orthogonal to one another.

The first nest 606 may be configured to receive the partially-assembled cartridge 300 and retain the partially-assembled cartridge in the recess 610. In this regard, the first nest 610 may include a locking member 614, which may clamp the partially-assembled cartridge 300 in the recess 610 such that the partially-assembled cartridge does not fall over or out of the first nest. For example, the locking member 614 may be configured to apply force to the base 302 (see, e.g., FIG. 3) to engage the partially-assembled cartridge 300. In this regard, the locking member 614 may be spring-loaded.

Further, the second nest 608 may comprise one or more clamps 616 configured to receive and hold the atomizer 310 (see, e.g., FIG. 3) in a substantially horizontal configuration when the assembly carriage 506*b* is positioned on the assembly track 504*b* in a horizontal configuration. The clamps 616 may press against liquid transport element 324 of the atomizer 310 (see, e.g., FIG. 3) such that the atomizer is retained in one or more channels 618. For example, the clamps 616 may be spring-loaded so as to securely engage the atomizer 310 in the one or more channels 618.

Accordingly, once the atomizer 310 (see, e.g., FIG. 3) is held in place at the second nest 608, the partially-assembled cartridge 300 may be removed from the first nest 606 and inserted into the second nest 608. The second nest 608 may additionally include a locking member 620, which may clamp the partially-assembled cartridge 300 in the recess 612 such that the partially-assembled cartridge 300 does not fall out of the second nest. In this regard, the locking member 620 may be spring-loaded and configured to apply force to the base 302 (see, e.g., FIG. 3) to engage the partially-assembled cartridge 300.

As illustrated in FIG. 8, the recess 612 of the second nest 608 may be configured to hold the partially-assembled cartridge 300 such that the first heating terminal 320*a* and the second heating terminal 320*b* thereof are in contact with the heating element 326 of the atomizer 310. In this regard, the first and second heating terminals 320*a*, 320*b* may be welded (e.g., laser welded) to the heating element 326 in the second nest 608. In order to facilitate welding of the first and second heating terminals 320*a*, 320*b* to the heating element 326 in the second nest 608, the clamps 616 may be configured to extend on first and second opposing sides of the partially-assembled cartridge 300. Thereby the clamps 616 may not interfere with welding equipment.

Further, as illustrated in FIG. 7, the second nest 608 may include a raised portion 622 positioned between the clamps 616. Thereby, the welding equipment may press the first and second heating terminals 320*a*, 320*b* against the heating element 326 (see, e.g., FIG. 8), which may be supported by the raised portion 622 of the nest. Accordingly, secure contact between the first and second heating terminals 320*a*, 320*b* and the heating element 326 may be achieved, which may improve the welds therebetween.

FIGS. 9 and 10 respectively illustrate perspective and top views of an embodiment of the assembly carriage 506*c* employed at the fourth and fifth assembly cells 502*d*, 502*e*. As illustrated, the assembly carriage 506*c* may include one or more first nests 624 and one or more second nests 626. The first nests 624 may be configured to receive the partially-assembled cartridges 300 in a first orientation, whereas the second nests 626 may be configured to receive the partially-assembled cartridge in a second orientation that differs from the first orientation.

In this regard, the first nest 624 may comprise a recess 628 configured to receive the partially-assembled cartridge 300. The recess 628 of the first nest 624 may be configured to hold the partially-assembled cartridge 300 in a substantially horizontal configuration. Conversely, the second nest 626 may comprise a receptacle 630 configured to receive a base 302 (see, e.g., FIG. 3) of the partially-assembled cartridge 300 such that the partially-assembled cartridge defines a substantially vertical configuration. Thereby, the first nest 624 and the second nest 626 may be configured to hold the partially-assembled cartridges 300 in configurations that are substantially orthogonal to one another.

As further illustrated in FIGS. 9 and 10, first nest 624 may further comprise a clamp 632. The clamp 632 may comprise a plurality of prongs 634 that extend on first and second opposing sides 624*a*, 624*b* of the first nest 624. The first and second opposing sides 624*a*, 624*b* of the first nest 624 may be elevated with respect to the recess 628.

As illustrated in FIG. 11, the clamp 632 may be configured to engage the reservoir substrate 312. In particular, the clamp 632 may press the reservoir substrate 312 against the first and second opposing sides 624*a*, 624*b* of the first nest 624 such that the reservoir substrate is suspended over the recess 628. In this regard, the recess 628 may be aligned and recessed with respect to the clamp 632.

Accordingly, the partially-assembled cartridge 300 may be prepared for insertion into the first nest 624 of the assembly carriage 506*c*. In this regard, the liquid transport element 324 of the atomizer 310 may be folded against the first and second heating terminals 320*a*, 320*b* of the flow director assembly 322 (see, FIG. 3) at the fourth assembly cell 502*d*.

In particular, as illustrated in FIG. 12, a flow director gripper 636 may grip the flow director 308 of the partially-assembled cartridge 300 (see, e.g., FIG. 3) and remove the partially-assembled cartridge from the transfer carriage 512*b*. The flow director gripper 636 may then direct the partially-assembled cartridge 300 to a folding apparatus 638. The folding apparatus 636 may include a plurality of folding pins 640 respectively defining a cutout 642. Further, the folding apparatus 638 may include a base gripper 644.

Thereby, the flow director gripper 636 may direct the partially-assembled cartridge 300 generally from right to left in terms of the illustrated orientation such that the base 302 (see, e.g., FIG. 3) is received in the base gripper 644 and the atomizer 310 (see, e.g., FIG. 3) is directed between the folding pins 640. As the atomizer 310 is directed between the folding pins 640, the atomizer may be received in the cutouts 642, which may restrain vertical movement of the atomizer, and the atomizer may bend inwardly toward the flow director 308. As illustrated, the folding apparatus 638 may include multiple sets of the folding pins 640, such that the folding pins engage the atomizer 310 along the length thereof.

Once the atomizer 310 is received between the folding pins 640, the base gripper 644 may grip the base 302 of the partially-assembled cartridge 300. The flow director gripper 636 may then release the flow director 308 and return to a starting position. The folding pins 640 may then move inwardly toward the partially-assembled cartridge 300 such that the atomizer 310 folds into contact with the flow director 308.

A transport gripper 646 may then grasp the partially-assembled cartridge 300 by pinching the atomizer 310 against the flow director 308 such that the atomizer retains the folded configuration formed at the folding apparatus 638. The folding pins 640 and the base gripper 644 may release the partially-assembled cartridge 300. The transport gripper 646 may then transport the partially-assembled cartridge 300 to, and deposit the partially-assembled cartridge in, the assembly carriage 506*c*.

Thereby, as illustrated in FIGS. 13 and 14, the reservoir substrate 312 may wrap at least partially around the partially-assembled cartridge 300 during insertion of the partially-assembled cartridge into the recess 628 at the first nest 624. In this regard, the reservoir substrate 312 may be pushed into the recess 628 as the partially-assembled cartridge 300 is inserted therein. More particularly, the flow director 308 may engage the reservoir substrate 312 and press the reservoir substrate downwardly into the recess 628. As the reservoir substrate 312 is pressed into the recess 628, the clamp 632 (see, e.g., FIG. 11), which is not shown in FIGS. 13 and 14 for clarity purposes, may release the ends of the reservoir substrate, which may be supported in an upwardly-extending configuration on opposing sides of the flow director 308 by the first and second opposing sides 624*a*, 624*b* of the first nest 624.

As illustrated in FIG. 14, once the partially-assembled cartridge 300 is received in the recess 628, an end effector 648 may clamp the reservoir substrate 312 against the partially-assembled cartridge 300 and lift the partially-assembled cartridge from the recess. The end effector 648 may comprise first and second prongs 648*a*, 648*b*, which may be configured to engage the reservoir substrate 312 at the opposing lateral sides of the partially-assembled cartridge 300. The prongs 648*a*, 648*b* may be sized and shaped in a manner that corresponds to the size and shape of the partially-assembled cartridge 300 in order to facilitate engagement therewith.

In order to clamp the reservoir substrate 312 against the partially-assembled cartridge 300 in this manner, the first nest 624 may further define first and second openings 650*a*, 650*b* positioned at the first and second opposing sides 624*a*, 624*b* of the first nest 624. Accordingly, the first and second prongs 648*a*, 648*b* of the end effector 648 may extend through the first and second openings 650*a*, 650*b* in the nest 624 to clamp the reservoir substrate 312 against the partially-assembled cartridge 300. After the outer body 314 (see, e.g., FIG. 3) is directed over the reservoir substrate 312 and into engagement with the flow director 308, the base 302 of the partially-assembled cartridge 300 may be inserted vertically into the second nest 626.

FIG. 15 illustrates an embodiment of the assembly carriage 506*d* employed at the assembly track 504*d* of the sixth assembly cell 502*f*. The assembly carriage 506*d* may include a relatively large number of receptacles 652 as compared to the other embodiments of the assembly carriages 506 employed by the system 400 (see, e.g., FIG. 5). In this regard, the partially-assembled cartridges 300 may be filled at the sixth assembly cell 502*f* with the aerosol precursor composition 328 (see, FIG. 5). Filling operations may be employed in multiple stages, and hence it may be desirable to hold and fill a relatively large number of the partially-assembled cartridges 300 in each assembly carriage 506*d* in order to keep up with other assembly operations, which may occur at a relatively faster pace. For example, in the illustrated embodiment the assembly carriage 506*d* is configured to hold twelve partially-assembled cartridges 300, which is three times more partially-assembled cartridges 300 than the other assembly carriages 506 are configured to hold in the illustrated embodiment. Accordingly, the assembly carriages

506*d* may accommodate the relative slow filling process by carrying a relatively large number of the partially-assembled cartridges.

FIG. 16 illustrates a method for assembling a plurality of cartridges for an aerosol delivery device. As illustrated, the method may include assembling a plurality of cartridge components together at a plurality of assembly cells at operation 702. Assembling the cartridge components together at operation 702 may include engaging a plurality of partially-assembled cartridges comprising one or more of the cartridge components with a respective one of one or more assembly carriage. Further, assembling the cartridge components together at operation 702 may include circulating the assembly carriages on an assembly track. The method may additionally include individually and sequentially transporting the partially-assembled cartridges on a transfer track between a pair of the assembly cells at operation 704.

In some embodiments of the method, individually and sequentially transporting the partially-assembled cartridges on the transfer track at operation 704 may include respectively engaging each of the partially-assembled cartridges with one of one or more transfer carriages. Individually and sequentially transporting the partially-assembled cartridges on the transfer track at operation 704 may further comprise disengaging the partially-assembled cartridges from the assembly carriages of a first one of the pair of the assembly cells and engaging the partially-assembled cartridges with a respective one of the transfer carriages. Additionally, individually and sequentially transporting the partially-assembled cartridges on the transfer track at operation 704 may include disengaging the partially-assembled cartridges from the transfer carriages and engaging the partially-assembled cartridges with one of the assembly carriages of a second one of the pair of the assembly cells.

FIG. 17 illustrates a method for assembling a cartridge for an aerosol delivery device according to an additional example embodiment of the present disclosure. As illustrated, the method may include receiving a partially-assembled cartridge in a first orientation in a first nest of an assembly carriage at operation 802. Further, the method may include receiving the partially-assembled cartridge in a second orientation that differs from the first orientation in a second nest of the assembly carriage at operation 804.

In some embodiments receiving the partially-assembled cartridge in the first orientation in the first nest of the assembly carriage at operation 802 may include receiving a base of the partially-assembled cartridge such that the partially-assembled cartridge defines a substantially vertical configuration. Further, the method may include receiving and holding an atomizer in a substantially horizontal configuration at the second nest. Receiving the partially-assembled configured cartridge in the second orientation in the second nest of the assembly carriage at operation 804 may include receiving the partially-assembled cartridge in a recess configured to hold the partially-assembled cartridge in a substantially horizontal configuration. Receiving the partially-assembled cartridge in the recess may include holding the partially-assembled cartridge such that a first heating terminal and a second heating terminal thereof are in contact with a heating element of the atomizer. Receiving and holding the atomizer in the substantially horizontal configuration at the second nest may include clamping the atomizer on first and second opposing sides of the partially-assembled cartridge.

In another embodiment the method may further include engaging a reservoir substrate with a clamp at the first nest. Receiving the partially-assembled cartridge in the first orientation in the first nest at operation 802 may include inserting the partially-assembled cartridge into a recess, the recess being aligned and recessed with respect to the clamp such that the reservoir substrate wraps at least partially around the partially-assembled cartridge during insertion of the partially-assembled cartridge into the recess. Engaging the reservoir substrate with the clamp may include engaging the reservoir substrate with a plurality of prongs that extend on first and second opposing sides of the nest. Further, the method may include directing an end effector into first and second openings positioned at the first and second opposing sides of the nest and clamping the reservoir substrate against the partially-assembled cartridge with the end effector. Engaging the prongs with the reservoir substrate may include pressing the reservoir substrate against the first and second opposing sides of the nest, the first and second opposing sides of the nest being elevated with respect to the recess.

As may be understood, the particular subsystems included in the system 400 (see, FIG. 4) and the method for assembling the cartridges 300 may vary. In this regard, FIG. 18 schematically illustrates an alternative embodiment of the system 400'. As illustrated, the system 400' may include a cartridge assembly subsystem 402', a cartridge filling subsystem 408', a cartridge capping subsystem 412', and a cartridge labeling subsystem 416'. Further, the system 400' may include a packaging subsystem 420'. The packaging subsystem 420' may be configured to package the completed cartridges 300. Note that although the controller 417 and the inspection subsystem 418 are not separately illustrated in FIG. 18, these components may additionally be included in the system 400' as described above with respect to FIG. 4. Further, note that the system 400' may conduct various inspection and quality control operations as described above, which are not repeated hereinafter for brevity purposes.

The subsystems 402', 408', 412', 416', 420' may respectively include one or more assembly cells 502*a-g*' (collectively, "assembly cells 502'"). In the embodiment illustrated in FIG. 18, the cartridge assembly subsystem 402' is divided into three assembly cells 502*a-c*'. Further, the cartridge filling subsystem 408', the cartridge capping subsystem 412', the cartridge labeling subsystem 416', and the packaging subsystem 420' each respectively comprise an assembly cell 502*d-g*'.

Preferably, the system 400' may be configured to rapidly produce the cartridges 300 with minimal human interaction being required. In this regard, the assembly cells 502' may be collectively configured to assemble a plurality of cartridge components together and/or perform additional functions with respect to the cartridges 300. In this regard, each assembly cell 502' may include an intra-cell transporter configured to transport the partially-assembled cartridges therethrough as various operations are performed thereon. Thereby, the partially or fully assembled cartridges 300 may be transported by the intra-cell transporter at each of the assembly cells 502' as the components of the cartridges are assembled together or other operations are performed thereon.

By way of example, the first assembly cell 502*a*' may include a rotary table 504*a*', which may receive the base 302. In one embodiment the rotary table 504*a*' may comprise a NR1100 rotary indexing ring available from Weiss GMBH of Buchen, Germany. Further, in some embodiments the bases 302 may be transported to rotary table 504*a*' via a linear feed system available from Vibratory Tooling & Repair, Inc. of Ontario, Canada.

The rotary table 504*a*' may transport the base 302 to various positions within the first assembly cell 502*a*' at which additional components may be engaged therewith. In particular, the control component terminal 304 may be engaged with the base 302, the electronic control component 306 may be engaged with the control component terminal, and the flow director assembly 322 may be engaged with the base. Further, the flow director assembly 322 may be affixed to the base (e.g., ultrasonically welded thereto) at the first assembly cell 502*a'*.

However, issues with respect to component movement may occur during the welding process. In this regard, as illustrated in FIG. 19, in some embodiments the base 302 may be received in a welding fixture 500. The welding fixture 500 may include a body 501 defining a receptacle configured to engage the base 302, the first heating terminal 320*a*, the second heating terminal 320*b*, and the electronic control component terminal 304.

Thereby, contact between the welding receptacle 500 and the base 302 and between the welding receptacle and the terminals 320*a*, 320*b*, 304 may stabilize each of the components of the partially-assembled cartridge 300 as well as the electronic control component 306, which is engaged with the control component terminal. In order to contact the base 302 and the terminals 320*a*, 320*b*, 304, in some embodiments a portion of the body 501 of the welding fixture 500 may define a size and shape substantially corresponding to that of the coupler 202 of the control body 200 (see, FIG. 2). Thus, when the flow director 308 is pressed against the base 302 during welding thereto, the welding fixture may securely support the components of the partially-assembled cartridge 300 in a desired position and prevent movement therebetween. However, the welding receptacle 500 may allow for some movement between the base 302 and the flow director 308 in embodiments in which ultrasonic welding is employed such that the necessary heat is generated by the relative motion therebetween.

Accordingly, the rotary table 504*a*' may position the base 302 for the engagement of other components therewith and performance of operations thereon at the first assembly cell 502*a*'. However, various other embodiments of intra-cell transporters may be employed at the assembly cells 502'. For example, as schematically illustrated in FIG. 18, the third assembly cell 502*c*' may include a rotary track 504*c*' to which a plurality of platforms 506*c*' are coupled in order to assemble the reservoir substrates 312 and the outer bodies 314 with the partially-assembled cartridges 300 as the partially-assembled cartridges are indexed by the rotary track. As may be understood, the system 400' may include various other types of intra-cell transporters configured to transport the partially-assembled cartridges 300 at the assembly cells 502', such as a conveyor (e.g., linear or belt), a robotic arm, a track and carriage(s), a pneumatic transporter, or any other embodiment of mechanism configured to transport components. Accordingly, the particular intra-cell transporters configured to transport the partially-assembled cartridges 300 at the assembly cells 502*a*' may vary, and will not be described in detail hereinafter.

As noted above, the electronic control component 306 may be engaged with the control component terminal 304 at the first assembly cell 502*a*'. However, issues with respect to static electricity buildup on the electronic control components 306 may affect the assembly of the cartridge 300 and/or programming thereof. In this regard, static buildup on the electronic control components 306 may cause the electronic control components to attract and bind with one another, which may make it more difficult to singulate the electronic control components prior to engagement with a respective control component terminal 304. Additionally or alternatively, static electricity built up on the electronic control components 306 may discharge during or after assembly, which may clear the memory thereon or present other issues with respect to storing information on the electronic control components.

Accordingly, as illustrated in FIG. 20, the first assembly cell 502*a*' may include an anti-static apparatus 508'. Although one anti-static apparatus 508' is illustrated in FIG. 20, in another embodiment two or more of the anti-static apparatuses may be employed. The anti-static apparatus 508' may be configured to direct ionized air at the electronic control components 306 (see, e.g., FIG. 3) to neutralize any electric charge thereon. In this regard, the electronic control components 306 may be initially received in a hopper 510' when added to the system 400' (see, FIG. 18), and the anti-static apparatus 508' may be configured to direct the ionized air at the electronic control components received therein. Thereby, static on the electronic control components 304 may be neutralized prior to singulation thereof and prior to programming the electronic control components downstream in the system 400'. One example embodiment of an anti-static apparatus is the minION2 Ionizing Air Blower available from Simco-Ion of Alameda, Calif.

As illustrated in FIG. 18, after the control component terminal 304, the electronic control component 306, and the flow director assembly 322 are engaged with the base 302 to form a partially-assembled cartridge 300, the partially-assembled cartridge is transported to the second assembly cell 502*b*'. In this regard, the system 400' may include inter-cell transporters configured to transport the partially and fully assembled cartridges 300 between the assembly cells 502'. For example, the system 400' may include an inter-cell transporter 512*a-f* (collectively, "inter-cell transporters 512'") between each pair of the assembly cells 502'. Thereby, after each assembly cell 502' performs one or more operations on the partially-assembled cartridge 300, the partially-assembled cartridge may be transported to the next assembly cell via one of the inter-cell transporters 512'. Various embodiments of the inter-cell transporter 512' may be employed. By way of example, the inter-cell transporters 508' may comprise a conveyor (e.g., linear or belt), a rotary table, a rotary track and platform(s), a robotic arm, a track and carriage(s), a pneumatic transporter, or any other embodiment of mechanism configured to transport components.

By way of example, FIG. 21 illustrates one embodiment of the inter-cell transporter 512*a*' between the first assembly cell 502*a*' and the second assembly cell 502*b*' in which the inter-cell transporter comprises a pneumatic transporter. As illustrated, the rotary table 504*a*' may transport the partially-assembled cartridges 300 to the transport system 512*a*'. In this regard, the partially-assembled cartridges 300 may be offloaded from the rotary table 504*a*' and received in a pneumatic inlet 514*a*', which may transport the partially-assembled cartridges 300 via transport lines 516*a*' to the second assembly cell 502*b*'. For example, compressed air may force the partially-assembled cartridges 300 through the transport lines 516*a*', or the partially-assembled cartridges may be drawn through the transport lines via a reduced pressure proximate the outlet thereto. Note that although the pneumatic inlet 514*a*' defines a relatively small radius in the illustrated embodiment defining a path along which the partially-assembled cartridges 300 travel, the shape thereof may vary in other embodiments. For example, the pneumatic inlet 514*a*' may define a relatively larger radius in other embodiments, which may make the partially-assembled cartridges 300 less prone to jamming therein. Usage of a pneumatic inter-cell transporter may be desirable in that it the transport lines 516*a*' may be formed of plastic or other flexible material that may allow for routing around other structures and/or along non-linear paths in a relatively easy manner. Thereby, the partially-assembled cartridges 300 may be transported to alternate locations with relative ease, regardless of the position thereof. Thus, the various assembly cells may be positioned as desired without necessarily being positioned in an ordered sequence corresponding to the sequence in which parts are added to the partially-assembled cartridges 300. Thereby, the inter-cell transporter 512*a*' may provide the system with additional flexibility in terms of the layout thereof.

In some embodiments the inter-cell transporter 512*a*' may be configured to transport the partially-assembled cartridges 300 in side profile. In other words, the inter-cell transporter may transport the partially-assembled cartridges 300 such that the partially-assembled cartridges 300 are moved in a direction perpendicular to a longitudinal axis thereof. Thus, the transport lines 516*a*' may define a cross-sectional profile corresponding to a side profile of the partially-assembled cartridge 300 leaving the first assembly cell 502*a*'. However, in other embodiments the partially-assembled cartridges 300 may be transported through the transport lines 516*a*' in a direction parallel to the longitudinal axis thereof.

Regardless of the particular embodiment of the inter-cell transporter 512*a*' employed, the partially-assembled cartridges 300 may be transported to the second assembly cell 502*b*'. As illustrated in FIG. 18, the atomizers 310 may be assembled with the partially-assembled cartridges 300 at the second assembly cell 502*b*'.

An example embodiment of the second assembly cell 502*b*' is illustrated in FIG. 22. As illustrated, the second assembly cell 502*b*' may include an input feeder 504*b*'. The input feeder 504*b*' may be configured to dispense a substantially-continuous input 518'. In this regard, the input feeder 504*b*' may include a spool 520' from which the substantially-continuous input 518' is dispensed. Further, the second assembly cell 502*b*' may include an assembly feeder 522'. The assembly feeder 522' may be configured to provide and position the partially-assembled cartridges 300 in contact with the substantially-continuous input 518' in the manner discussed below. In this regard, the second assembly cell 502*b*' may further comprise a welder 524' configured to weld the partially-assembled cartridge 300 to the substantially-continuous input 518'.

FIG. 23 illustrates an enlarged, partial view of the second assembly cell 502*b*' wherein the welder 524' (see, FIG. 20) is not shown. As illustrated, the second assembly cell 502*b*' may further comprise a cutter 526'. The cutter 526' may be configured to cut the substantially-continuous input 518' to singulate an atomizer 310 (see, e.g., FIG. 3).

In this regard, as illustrated in FIG. 24, the input feeder 504*b*' may include a dispensing clamp 528' and an end clamp 530'. The dispensing clamp 528' may include opposing grippers 528*a*', 528*b*'. A first gripper 528*a*' may include an extension 528*a*1' configured to extend under the substantially continuous input 518' to thereby guide the substantially continuous input 518' into position for gripping between the opposing grippers 528*a*', 528*b*'. Similarly, the end clamp 530' may include opposing grippers 530*a*', 530*b*', wherein the first gripper 530*a*' includes an extension 530*a*1' configured to extend under the substantially continuous input 518' to thereby guide the substantially continuous input 518' into position for gripping between the opposing grippers 530*a*', 530*b*'.

The dispensing clamp 528' may be configured to grasp the substantially-continuous input 518' at a starting position. Once grasped, the dispensing clamp 528' may pull on the substantially-continuous input 518', by moving generally from left to right in terms of the illustrated orientation to an extended position. Thereby, the end clamp 530' may grasp the substantially-continuous input 518' proximate an end thereof. The dispensing clamp 528' may then release the substantially-continuous input 528', move back to the starting position (e.g., by moving generally right to left in terms of the illustrated orientation), and grasp the substantially-continuous input, as illustrated in FIG. 24. Accordingly, a segment 520*a*' of the substantially-continuous input 518' may be clamped between the dispensing clamp 528' and the end clamp 530'.

As illustrated, the substantially-continuous input 518' may comprise a plurality of heating elements 326 engaged with the substantially-continuous liquid transport element 324. In this regard, the dispensing clamp 528' and the end clamp 530' may be configured to clamp the substantially-continuous input 518' such that the segment 520*a*' includes one of the heating elements 326. Accordingly, the segment 520*a*' of the substantially-continuous input 518' may be positioned for engagement with one of the partially-assembled cartridge assemblies 300.

In this regard, the assembly feeder 522' may be configured to engage the first heating terminal 320*a* and the second heating terminal 320*b* of one of the partially-assembled cartridges 300 with one of the heating elements 326 at the segment 520*a*' of the substantially-continuous input 518'. For example, as described above, the partially-assembled cartridge 300 may further comprise a base 302 and a flow director 308, wherein the first heating terminal 320*a* and the second heating terminal 320*b* extend through the flow director. Thereby, the assembly feeder 522' may grasp the partially-assembled cartridges 300 such that the first heating terminal 320*a* and the second heating terminal 320*b* are exposed for engagement with the heating element 326 at the segment 520*a*' of the substantially-continuous input 518'. As illustrated, the assembly feeder 522' may include at least one end effector 532' configured to engage the base 302 of the partially-assembled cartridge 300. In some embodiments the end effector 532' may be configured to apply a negative pressure to the base 302 of the partially-assembled cartridge 300 to retain the partially-assembled cartridge in engagement therewith during movement of the assembly feeder 522'.

Further, as illustrated in FIG. 23, the assembly feeder 522' may comprise a rotary transporter 534' (e.g., a rotary wheel) configured to rotate to transport the partially-assembled cartridges 300. The end effectors 532' may be coupled to the rotary transporter 534'. Thereby, the rotary transporter 534' may rotate such that the first heating terminal 320*a* and the second heating terminal 320*b* engage the one of the heating elements 326, as illustrated in FIG. 24.

Once the first heating terminal 320*a* and the second heating terminal 320*b* of the partially-assembled cartridge 300 engage the heating element 326 at the segment 520*a*' of the substantially-continuous input 518', the welder 524' (see, FIG. 22) may weld the heating terminals to the heating element. In some embodiments the welder 524' may comprise a laser welder 536', as illustrated in FIG. 22. The laser welder 536' may be configured to produce a laser beam 538', which may be aimed at the first heating terminal 320*a* and the second heating terminal 320*b* or the heating element 326 in order to heat and weld the heating terminals to the heating element (see, e.g., FIG. 24).

As further illustrated in FIG. 22, in some embodiments the laser welder 536' may be configured to direct the laser beam 538' at any location within a space 540' (e.g., defining an area or volume). For example, the laser welder 536' may be mounted to actuators or otherwise configured to move to direct the laser beam 538' at the first heating terminal 320*a* and the second heating terminal 320*b* (see, e.g., FIG. 24). Alternatively, the welder 524' may be configured to focus the laser beam 538' within the space 540'.

In this regard, the laser welder 536' may include an adjustable optical lens 542' configured to focus the laser beam 538' within the space 540'. Thereby, the welder 524' may focus the laser beam 538' at the first heating terminal 320*a* and the second heating terminal 320*a* of the partially-assembled cartridge 300 or corresponding portions of the heating element 326 (see, e.g., FIG. 24). Further, as a result of employing the adjustable optical lens 542', the laser welder 536', the first heating terminal 320*a*, and the second heating terminal 320*b* may remain stationary during and between welding the first heating terminal and the second heating terminal to the one of the heating elements 326 (see, e.g., FIG. 24). By using the adjustable optical lens 542', rather than actuators configured to move the laser welder 536', issues with respect to rapidly and precisely moving the laser welder may be avoided. Thereby, the throughput of the second assembly cell 502*b'* may be improved. In one embodiment the laser welder 536' may comprise a TruPulse laser available from TRUMPF, Inc. of Plymouth Township, Mich. Further, the adjustable optical lens 542' may comprise a PFO20 programmable focusing optic, also available from TRUMPF, Inc.

Accordingly, the first heating terminal 320*a* and the second heating terminal 320*b* may be welded to the heating element 326 in the configuration illustrated in FIG. 24. After the welding is completed, the cutter 526' may cut the substantially-continuous input 518' between the dispensing clamp 528' and the end clamp 530'. Thereby, the segment 520*a'* of the substantially-continuous input 518' may be cut from substantially-continuous input 518' to singulate the one of the heating elements 326 to which the first heating terminal 320*a* and the second heating terminal 320*b* are attached and a corresponding segment of the liquid transport element 324.

Note that cutting the substantially-continuous input 518' after welding the heating element 326 to the first and second heating terminals 320*a*, 320*b* may provide benefits as compared to singulating the atomizer 310 (see, e.g., FIG. 3) before welding the heating element to the heating terminals. In this regard, the input feeder 504*b'* may be employed not only to dispense the substantially-continuous input 518', but also to hold the segment 520*a'* thereof that is welded to the first and second heating terminals 320*a*, 320*b* during the welding process. Thus, the input feeder 504*b'* may serve multiple functions, which may reduce the cost and complexity of the second assembly cell 502*b'*.

Further, by cutting the substantially-continuous input 518' after welding the atomizer 310 to the first and second heating terminals 320*a*, 320*b*, the input feeder 504*b'* may firmly grasp the substantially-continuous input 518' during welding. In this regard, in embodiments in which the atomizer 310 is singulated before welding, the length of the liquid transport element 324 defines the boundaries at which the atomizer may be grasped. In contrast, when the segment 520*a'* is still intact with the substantially-continuous input 518', the substantially-continuous input may be grasped at any point therealong.

For example, as illustrated in FIG. 24, the dispensing clamp 528' may grasp the substantially-continuous input 518' outside of the segment 520*a'* to be cut therefrom after being welded to the first and second heating terminals 320*a*, 320*b*. As further illustrated in FIG. 24, the dispensing clamp 528' may include multiple sets of pinchers 544'. In this regard, usage of multiple sets of pinchers 544' may allow for grasping of the substantially-continuous input 518' at multiple locations therealong, such that the substantially-continuous input is more securely grasped. Further, the pinchers 544' may be configured to surround and stabilize the heating element 326 during dispensing. Thereby, the substantially-continuous input 518' may be grasped to allow the first and second heating terminals 320*a*, 320*b* to be pressed firmly against the heating element 326 during welding in order to provide mating contact that facilitates forming a strong weld therebetween.

Accordingly, the partially-assembled cartridge 300 may include an atomizer 310 (see, FIG. 3) following the welding and cutting operations described above. Thereafter, the second assembly cell 502*b'* may cycle to couple additional atomizers to other partially-assembled cartridges. In this regard, the end clamp 530' may open to release the end of the singulated atomizer 310. The rotary transporter 534' of the assembly feeder 522' may then rotate such that the partially-assembled cartridge 300 including the atomizer 310 is moved away from the substantially-continuous input 518'. The dispensing clamp 528' may then start the cycle described above again by moving generally left to right in terms of the orientation illustrated in FIG. 24 from the starting position to the extended position in order to allow the end clamp 530' to engage the substantially-continuous input 518'. The dispensing clamp 522' may then move to the left to the starting position, at which time the rotary transporter 534' may rotate further to bring an additional partially-assembled cartridge 300 into contact with the substantially-continuous input 518' at a heating element 326, as illustrated in FIG. 24. Accordingly, the process of welding the atomizers 310 to the first and second heating terminals 320*a*, 320*b* of the partially-assembled cartridges 300 may be iteratively repeated.

As illustrated in FIG. 25, in some embodiments the second assembly cell 502*b'* may further comprise a second input feeder 504*b''* and a second assembly feeder 522''. The second input feeder 504*b''* may be configured to dispense a second substantially-continuous input 518'' comprising a plurality of heating elements 326 engaged with a substantially-continuous liquid transport element 324. The second assembly feeder 522'' may be configured to engage the first heating terminal 320*a* and the second heating terminal 320*b* of partially-assembled cartridges 300 with one of the heating elements 326 by transporting the partially-assembled cartridges into engagement therewith.

Thus, the second input feeder 504*b''* may be substantially the same as, and include the same components as, the input feeder 504*b'*. Additionally, the second input feeder 504*b''* may be substantially the same as, and include the same components as, the input feeder 504*b'*. Accordingly, the input feeders 504*b'*, 504*b''* and the assembly feeders 522', 522'' may position the partially-assembled cartridges 300 in contact with the substantially-continuous inputs 518', 518''. Thereby, the first and second heating terminals 320*a*, 320*b* of the partially-assembled cartridges 300 may be welded to the heating elements 326 at both of the substantially-continuous inputs 518', 518".

As noted above in relation to FIGS. 22 and 24 use of the adjustable optical lens 542' may allow for rapid focusing of the laser beam 538' at the first heating terminal 320*a* and the second heating terminal 320*b* or corresponding portions of the heating element 326. Additionally, use of the adjustable optical lens 542' may provide additional benefits. For example, in view of the adjustable optical lens 542' being configured to direct the laser beam 538' within the space 540', the welder 524' may be employed to weld the partially-assembled cartridges to both of the substantially-continuous inputs 518', 518" illustrated in FIG. 25. In this regard, the input feeders 504*b'*, 504*b"* may be configured to position both of the substantially-continuous inputs 518', 518" in the space 540' within which the welder 524' may direct the laser 538' (see, FIG. 22). Further, the assembly feeders 522', 522" may be configured to position the partially-assembled cartridges 300 such that the heating terminals 320*a*, 320*b* are in the space 540' within which the welder 524' may direct the laser 538' (see, FIG. 22).

Accordingly, in some embodiments a single welding apparatus (e.g., the welder 524') may be employed to weld two assembly lines of the partially-assembled cartridges 300 directed through the second assembly cell 502*b'*. Similarly, in some embodiments a single cutter (e.g., the cutter 526') may be employed to cut both of the substantially-continuous inputs 518', 518". In this regard, in some embodiments the first assembly feeder 522' and the first input feeder 504*b'* may be out of synch with the second assembly feeder 522" and the second input feeder 504*b"* such that the welder 524' and/or the cutter 526' may alternatingly perform operations on the first substantially-continuous input 518' and the second substantially-continuous input 518". Usage of a single welder and/or a single cutter may reduce costs and complexity of the second assembly cell 502*b'*. However, as may be understood, in other embodiments, multiple welders and/or cutters may be employed at the second assembly cell.

Note that although the heating element 326 is described herein as being attached to the heating terminals 320*a*, 320*b* via laser welding, various other types of welding may be employed, such as arc welding, metal inert gas welding (MIG), tungsten inert gas welding (TIG), plasma welding, etc. More broadly, the heating elements may be affixed to the heating terminals via other methods, such as soldering and mechanical connections. Accordingly, it should be understood that various other embodiments of coupling methods and related equipment may be employed without departing from the scope of the present disclosure.

Accordingly, as illustrated in FIG. 18 and as described above, atomizers 310 may be coupled to the partially-assembled cartridges 300, and the partially assembled cartridges may be directed to the third assembly cell 502*c'* via a second inter-cell transporter 512*b'*. The reservoir substrate 312 and the outer body 314 may be engaged with each of the partially-assembled cartridges 300 at the third assembly cell 502*c'*. Accordingly, the third assembly cell 502*c'* may include equipment particularly configured to assemble the reservoir substrate 312 and the outer body 314 with the partially-assembled cartridges 300.

As noted above with respect to FIG. 18, the third assembly cell 502*c'* may include a rotary track 504*c'* to which a plurality of platforms 506*c'* are coupled. The platforms 506*c'* may be configured to transport the partially-assembled cartridges 300 as the reservoir substrates 312 and the outer bodies 314 are coupled thereto. FIG. 26 illustrates an enlarged, partial view of one of the platforms 506*c'* engaged with the rotary track 504*c'*.

As illustrated in FIG. 26, the platforms 506*c'* may include one or more assembly grippers 546' coupled thereto, which may grasp the partially-assembled cartridges 300. As may be understood the particular components of the assembly grippers 546', and the exact manner in which the assembly grippers grasp the partially-assembled cartridges 300 may vary. However, the embodiment of the assembly grippers 546' provided herein may provide advantages in terms of being configured to perform opening and closing sequences that may facilitate grasping delicate and/or flexible components of the partially-assembled cartridges 300, which may move during grasping. Further, usage of the assembly grippers 546' may facilitate coupling of the reservoir substrate 312 and the outer body 314 to the partially-assembled cartridge 300 (see, e.g., FIG. 18) as described hereinafter.

Thus, in one example embodiment, each assembly gripper 546' may include a plurality of clamps 548A-C' (generically and collectively, "clamp(s) 548'"). Each clamp 548' may include a first finger 550' and a second finger 552'. As illustrated in FIG. 26, the clamps 548' may be configured to grasp partially-assembled cartridges 300 including the flow director 308, the atomizer 310, the first heating terminal 320*a*, and the second heating terminal 320*b*, wherein the first heating terminal and the second heating terminal are coupled to the atomizer.

Each assembly gripper 546' may further include a body 554' to which the clamps 548' are hingedly coupled. The body 554' may be integral or comprise multiple pieces, which may be positioned between the clamps 548'. The body 554' may define at least one access port 556'. The access port 556' may be configured to receive an actuator pin 558' (see, e.g., FIG. 27) to open the clamps 548'.

In this regard, FIG. 27 schematically illustrates the clamps 548' in an open configuration. As illustrated in FIG. 27, when the actuator pin 558' is received in the access port 556', the actuator pin may contact the inner surfaces of the clamps 548'. The first finger 550' may be hingedly coupled to the body 554' via a first hinge pin 560' and the second finger 552' may be hingedly coupled to the body via a second hinge pin 562'. Accordingly, contact between the inner surfaces of the fingers 550', 552' of the clamps 548' may cause the clamps to hingedly open to the position illustrated in FIG. 27.

Each assembly gripper 546' may include multiple clamps 548'. For example, in the embodiment illustrated in FIG. 26, the assembly gripper 546' includes an upper clamp 548A', a middle clamp 548B', and a lower clamp 548C'. Insertion of the actuator pin 558' may be configured to engage and sequentially open the clamps 548' as the actuator pin comes into engagement therewith.

As illustrated in FIG. 27, in some embodiments the actuator pin 558' may define a tapered tip 562'. The tapered tip 562' may facilitate engagement of the actuator pin 558' with the clamps 548' by progressively pressing outwardly on the clamps during insertion of the actuator pin. In other embodiments the clamps 548' may additionally or alternatively define tapered inner surfaces that the actuator pin 558' engages and which perform the same functions as the tapered tip 562' as described herein.

FIG. 28 schematically illustrates sequential opening of the clamps 548' during insertion of the actuator pin 558'. In this regard, the height of the actuator pin 558' is illustrated in relation to that of the clamps 548' and the corresponding lateral opening width of the clamps. As illustrated, the actuator pin 558' may be directed upwardly through the access port 556' (see, e.g., FIG. 27). Thereby, the lower clamp 548C' may begin opening first, and the middle and upper clamps 548B', 548A' may sequentially begin opening thereafter in that order.

Once the actuator pin 558' is fully inserted, the clamps 548' may be spread apart in the open configuration, as illustrated in FIGS. 27 and 29. Thereby, the partially-assembled cartridge 300 may be positioned between the fingers 550', 552' of the clamps 548'. For example, the platform 506*c*' (see, FIG. 26) may include a receptacle 564' at each assembly gripper 546'. The receptacle 564' may be configured to receive the base 302 of the partially-assembled cartridge 300.

Thus, as illustrated in FIG. 29, the partially-assembled cartridge 300 may be directed into the receptacle 564' while the fingers 550', 552' of the clamps 548' are in the open configuration. In this regard, an assembly clamp 566' may be configured to engage the partially-assembled cartridge 300 therebetween. The assembly clamp 566' may include a plurality of clamping portions 568', 570", which may engage the partially-assembled cartridge 300 therebetween.

As illustrated in FIG. 30, once the partially-assembled cartridge 300 is received in the receptacle 564', the assembly clamp 566' may release the partially-assembled cartridge 300. In this regard, the clamping portions 568', 570' of the assembly clamp 566' may separate to release the partially-assembled cartridge 300. Thereby, the assembly clamp 566' may retract away from the assembly gripper 546'.

As illustrated in FIG. 29, the assembly clamp 566' may engage the partially-assembled cartridge 300 such that the liquid transport element 324 is bent downwardly along the sides of the flow director 308. The liquid transport element 324 may be at least partially resilient. Thereby, as illustrated in FIG. 30, when the assembly clamp 566' releases the partially-assembled cartridge 300, the liquid transport element 324 may bend partially back to a linear configuration. However, the ends of the liquid transport element 324 may contact the clamps 548 such that the liquid transport element does not fully return to a linear configuration.

Thus, as illustrated in FIG. 31, when the clamps 548' are moved to a closed configuration, the liquid transport element 324 may fold along the sides of the flow director 308. In particular, the actuator pin 558' may be retracted downwardly through the access port 556' (see, e.g., FIG. 26). Thereby, the clamps 548' may clamp against the partially-assembled cartridge 300.

In this regard, when the actuator pin 558' is retracted out through the access port 556' in the body 554' (see, e.g., FIG. 2526 the fingers 550', 552' of the clamps 548' may clamp against the partially-assembled cartridge 300. For example, as illustrated in FIG. 32, the first finger 550' may be engaged with a first spring 572' and the second finger 552' may be engaged with a second spring 574'. Thereby, when the actuator pin 558' (see, e.g., FIG. 31) is retracted, the clamps 548' may sequentially close and clamp against the partially-assembled cartridge 300. In particular, as illustrated in FIG. 31, the upper clamp 548A' may close first, followed by the middle clamp 548B' and the lower clamp 548C'. By closing the clamps in this sequence, the liquid transport element 324 may be pressed against the flow director 308 such that the ends of the liquid transport element are in close contact with the flow director.

Thus, the liquid transport element 324 may be securely clamped against the sides of the flow director, 308. The springs 572', 574' may be in compression in both the open configuration illustrated in FIG. 27 and the closed configuration illustrated in FIG. 32. Thereby, the springs 572', 574' may press against the fingers 550', 552' in the closed configuration to retain the fingers in engagement with the partially-assembled cartridge 300.

Positioning the liquid transport element 324 in a folded configuration along the sides of the flow director 308 may allow the reservoir substrate 312 (see, e.g., FIG. 3) to be wrapped around the liquid transport element as discussed below. In this regard, the rotary track 504*c*' may increment the position of the platforms 506*c*' (see, e.g., FIG. 26), such that the partially-assembled cartridge 300 is positioned for engagement of the reservoir substrate 312 (see, e.g., FIG. 3) thereon.

Accordingly, the assembly gripper 546' may be prepared for receipt of the reservoir substrate 312 (see, e.g., FIG. 3). In this regard, the clamps 548' may return to the open configuration. For example, as illustrated in FIG. 33, an actuator pin 576' may be inserted through the access port 556' to sequentially open the clamps 548'. In some embodiments the actuator pin 576' may be inserted upwardly through the access port 556' to open the clamps 548'.

After the clamps 548' are opened, the partially-assembled cartridge assembly 300 may be stabilized. In this regard, as illustrated in FIG. 34, a cap 578' may be engaged with the top of the partially-assembled cartridge 300 while the clamps 548' are in the open configuration. Thus, the cap 578', in combination with the receptacle 564', may stabilize the partially-assembled cartridge 300.

Accordingly, as illustrated in FIG. 33, a substrate gripper 580' may engage the reservoir substrate 312. The reservoir substrate 578' may comprise a patch of material that may be cut from a substantially-continuous reservoir substrate input using, for example, an ultrasonic cutter. Usage of an ultrasonic cutter may substantially seal the ends of the reservoir substrate 578' to avoid issues with respect to loose fibers in the reservoir substrate 578'. Additionally, in some embodiments an ultrasonic welder may be employed to join the ends of two rolls of substantially-continuous reservoir substrate input such that a continuous input of the reservoir substrate is provided at the third assembly cell 502*c*' to avoid unnecessary stoppages.

In order to engage the reservoir substrate 312, the substrate gripper 580' may include one or more protrusions 582'. For example, the protrusions 582' may include an inner protrusion 584' and outer protrusion 586'. At least one of the protrusions 582' may be configured to apply a negative pressure to the reservoir substrate 312. In this regard, at least one of the protrusions 582' may include a pressure port 588' configured to apply the negative pressure to the reservoir substrate 312 to retain the reservoir substrate in engagement therewith. By way of example, the inner protrusion 584' includes the pressure port 588' in the illustrated embodiment. In this regard, as described below, the inner protrusion 584' may remain substantially stationary with respect to the reservoir substrate 312 by remaining in engagement therewith during wrapping of the reservoir substrate about the partially-assembled cartridge 300, whereas the outer protrusions 586' may move with respect to the reservoir substrate during wrapping of the substrate about the partially-assembled cartridge 300.

Accordingly, as illustrated in FIG. 33, the substrate gripper 580' may position the reservoir substrate 312 in contact with the partially-assembled cartridge 300. The substrate gripper 580' may then wrap the reservoir substrate 312 about the partially-assembled cartridge 300, as illustrated in FIG. 35. In this regard, the outer protrusions 586' may extend around the partially-assembled cartridge 300 when the inner protrusion 584' directs the reservoir substrate 312 into contact with the partially-assembled cartridge. Further, the outer protrusion 586' may extend inward toward one another such that the reservoir substrate 312 wraps about the partially-assembled cartridge 300.

As illustrated in FIG. 36, the cap 578' may lift and disengage from the partially-assembled cartridge 300 after the reservoir substrate 312 is wrapped thereabout by the substrate gripper 580'. Further, as illustrated in FIG. 37, the assembly gripper 546' may move to the closed position as the actuator pin 576' (see, FIG. 35) is retracted from the access port 556'. Thereby, the assembly gripper 546' may engage the reservoir substrate 312 such that the reservoir substrate is retained in place on the partially-assembled cartridge 300.

Accordingly, as illustrated in FIG. 38, the substrate gripper 580' may release the reservoir substrate 312 after the clamps 548' close. As illustrated in FIG. 36, the protrusions 582' of the substrate gripper 580' may intermesh with the clamps 548' of the assembly gripper 546' when both the assembly gripper and the substrate gripper engage the reservoir substrate 312. In this regard, one or more gaps 590' may be defined between the clamps 548' of the assembly gripper 546'. Thereby, one or more of the protrusions 582' of the substrate gripper 580' may be received in the gaps 590' when the assembly gripper 546' clamps the reservoir substrate 312. Thus, during retraction of the substrate gripper 580' following clamping of the reservoir substrate 312 by the assembly gripper 546', the substrate gripper may retract away from the partially-assembled cartridge 300 and return to the initial position and configuration to receive a reservoir substrate 312 for the next partially-assembled cartridge 300. In this regard, the protrusions 582' of the reservoir gripper 580' may retract through the gaps 590' (see, FIG. 36), such that the assembly gripper 546' may remain in engagement with the partially-assembled cartridge 300 while the substrate gripper 580' disengages and retracts from the partially-assembled cartridge.

After the reservoir substrate 312 is added to the partially-assembled cartridge 300, the outer body 314 may be engaged therewith. In this regard, FIG. 39 schematically illustrates attachment of the outer body 314 to the partially-assembled cartridge 300. As illustrated, the rotary track **504*c*' (see, FIG. 18) may direct the platform 506*c*' to an outer body coupling apparatus 592'. The outer body coupling apparatus 592' may include an actuator pin 594' and an outer body gripper 596'. The actuator pin 594' may be coupled to the outer body gripper 596'** such that each moves simultaneously.

As illustrated in FIG. 39, the outer body coupling apparatus 592' may direct the actuator pin 594' downwardly into the access port 556' while the outer body gripper 596' directs the outer body 314 over the partially-assembled cartridge 300. The actuator pin 594' may include a tapered tip 598', or the clamps 548' may be tapered at inner surfaces thereof, as described above. Thereby, the actuator pin 594' may progressively and sequentially open each of the clamps 548' such that the outer body 314 is directed over the partially-assembled cartridge 300 without the clamps interfering therewith.

This method of operation may still allow the clamps 548' to clamp the reservoir substrate 312 during the outer body 314 engagement process. In this regard, when the upper clamp 548A' is fully open and the outer body 314 is directed at least partially over the partially-assembled cartridge 300, the middle clamp 548B' and the lower clamp 548C' may be at least partially closed and in engagement with the reservoir substrate 312 to assist in retaining the reservoir substrate in a desired position. Accordingly, the sequential opening of the clamps 548 while the outer body 314 is directed over the partially-assembled cartridge 300 may assist in coupling the outer body to the partially-assembled cartridge without moving the reservoir substrate 312 from a desired position. In this regard, if the reservoir substrate 312 were to shift out of position, it may extend between the outer body 314 and the base 302, which may provide an undesirable appearance and/or potentially cause fluid leakage from the assembled cartridge.

After the outer body 314 is added to the partially-assembled cartridge 300, the outer body may be welded thereto. For example, the outer body 314 may be attached to the flow director 308 and/or the base 302. By way of further example, the outer body 314 may be ultrasonically welded to the flow director 308 and/or the base 302. However, as may be understood, the outer body 314 may be affixed to the remainder of the partially-assembled cartridge 300 in various other manners in other embodiments.

FIG. 40 illustrates welding of the outer body 314 to the base 302. The outer body 314 may be alternatively or additionally welded to the flow director 308 (see, e.g., FIG. 3), as noted above. As illustrated, a welding clamp 654' may retain the partially-assembled cartridge 300 in a desired position during ultrasonic welding of the outer body 314 to the base 302. The welding clamp 654' may include opposing cartridge grippers **656*a*', 656*b*'. The cartridge grippers 656*a*', 656*b*' may be configured to intermesh with the first fingers 550' and the second fingers 552' of the assembly gripper 546'. The fingers 550', 552' of the assembly gripper 546' may be partially opened so as to be out of contact with the partially-assembled cartridge 300** but in close proximity thereto.

In this regard, as illustrated in FIG. 41, the first cartridge gripper **656*a*' may include one or more intermeshing protrusions 658*a*' that intermesh with the first fingers 550' (see, e.g., FIG. 40) of the assembly gripper 546'. Similarly, as illustrated in FIG. 42, the second cartridge gripper 656*b*' may include one or more intermeshing protrusions 658*b*' that intermesh with the second fingers 552' of the assembly gripper 546' (see, e.g., FIG. 40). Accordingly, as illustrated in FIG. 40, the welding clamp 654' may clamp the partially-assembled cartridge 300**.

In particular as illustrated in FIG. 41, the first cartridge gripper **656*a*' may include a base protrusion 660*a*'. Similarly, as illustrated in FIG. 42, the second cartridge gripper 672*b*' may include a base protrusion 660*b*'. Thereby, as illustrated in FIG. 40, the base protrusions 660*a*', 660*b*' of the opposing cartridge grippers 656*a*', 656*b*' may cooperate to securely grip the base 302. Further, as illustrated in FIG. 41, the first cartridge gripper 656*a*' may include an outer body protrusion 662*a*' and, as illustrated in FIG. 42, the second cartridge gripper 656*b*' may include an outer body protrusion 662*b*'**.

As noted above, the first fingers 550' and the second fingers 552' of the assembly gripper 546' may release from the partially-assembled cartridge 300 during the welding operation so as to not interfere therewith. In this regard, it may be desirable to provide the outer body 314 with a degree of freedom to move with respect to the base 302 to allow the ultrasonic vibrations to produce a sufficient degree of heat to melt one or both of the outer body 314 and the base 302 at the interface therebetween and form a weld. However, too much freedom of movement of the outer body 314 with respect to the base 302 may allow misalignment therebetween.

Whereas the base 302 may be firmly grasped between the base protrusions **660*a*', 660*b*'**, the intermeshing protrusions

658*a*', 658*b*' and the outer body protrusions 662*a*', 662*b*' may loosely grasp the outer body 314. In this regard, a distance between the outer body protrusion 662*a*' of the first cartridge gripper 656*a*' and the outer body protrusion 662*b*' of the second cartridge gripper 656*b*' may be greater than a distance between the base protrusion 660*a*' of the first cartridge gripper and the base protrusion 660*b*' of the second cartridge gripper. Further, a distance between the outer body protrusion 662*a*' of the first cartridge gripper 656*a*' and the outer body protrusion 662*b*' of the second cartridge gripper 656*b*' is greater than a dimension of the outer body 314 of the cartridge 300 therebetween (e.g. the diameter thereof) when the base protrusion 660*a*' of the first cartridge gripper and the base protrusion 660*b*' of the second cartridge gripper engage the base 302 of the cartridge. Accordingly, the outer body 314 may be gripped more loosely than the base 302. For example, the outer body protrusions 662*a*', 662*b*' may be positioned adjacent to, but out of contact with, the outer body 314. Further, whereas each of the base protrusions 660*a*', 660*b*' and the intermeshing protrusions 658*a*' and the outer body protrusion 662*a*' of the first cartridge gripper 656*a*' may respectively define a groove 660*a*1', 660*b*1', 658*a*1', 662*a*1' configured to receive the cartridge therein, intermeshing protrusions 658*b*' and the outer body protrusion 662*b*' of the second cartridge gripper 656*b*' may respectively define a substantially flat face 658*b*1', 662*b*1'.

Thereby, by providing a greater separation between the outer body protrusions 662*a*', 662*b*' than the base protrusions 660*a*', 660*b*' and/or providing some of the protrusions with the flat face 658*b*1', 662*b*1', the outer body 314 may move slightly between the first and second cartridge grippers 656*a*', 656*b*' to allow for constrained relative movement of the outer body 314 with respect to the base 302 when an ultrasonic horn 664 is lowered into engagement with the top of the outer body. By allowing for movement, a weld may be produced at the interface between the outer body 314 and the base 302. In this regard, gripping the outer body 314 too tightly may otherwise result in the top of the outer body 314 mushrooming outwardly due to movement with respect to the ultrasonic horn 664'. This mushrooming effect may be avoided by allowing the outer body 314 to move relative to the base 302. However, the first and second cartridge grippers 656*a*', 656*b*' may constrain the movement such that the outer body 314 and the base 302 maintain proper alignment during the welding process.

Note that although the description provided above generally describes tightly clamping the base and allowing constrained movement of the outer body during ultrasonic welding, in other embodiments the opposite configuration may be employed. In other words, the outer body may be tightly clamped, whereas the base may be allowed to move within a constrained space dictated by the welding clamp. In this embodiment the ultrasonic horn may engage the base at an end thereof opposite from the outer body. Accordingly, as may be understood, the welding clamp may be configured in various manners to tightly clamp one of two components being ultrasonically welded together, and allow for constrained movement of the second component which is contacted by the ultrasonic horn to weld the two components together in a desired alignment. This configuration may be used in any ultrasonic welding method and is thus applicable to welding components other than a base and an outer body.

After the outer body 314 is welded to the partially-assembled cartridge 300, the partially-assembled cartridge may be offloaded from the rotary track 504*c*' and transported via the third inter-cell transporter 512*c*' to the fourth assembly cell 502*d*' at which the partially-assembled cartridge 300 may be filled with the aerosol precursor composition 328, as illustrated in FIG. 18. For example, as illustrated in FIG. 43, the cartridge filling subsystem 408' may include a filling apparatus 666'. The cartridge filling subsystem 408' may further include an assembly carriage 506*d*' that may be employed to hold the partially-assembled cartridges 300 at the cartridge filling subsystem 408' in order to fill the partially-assembled cartridges with the filling apparatus 666'. The assembly carriage 506*d*' may include a plurality of receptacles 652'. As illustrated in FIG. 44, the receptacles 652' may be configured to receive the partially-assembled cartridges 300. In some embodiments the assembly carriage 506*d*' may include a mechanism configured to releasably retain the partially-assembled cartridges 300 in the receptacles 652'. For example, in the illustrated embodiment the assembly carriage 506*d*' includes a sphere 668' (e.g., a ball bearing) which may extend through an opening 670' at each receptacle 652'. A spring may bias each sphere 668' through a respective one of the opening 670' to thereby apply pressure to an outer surface of the partially-assembled cartridge 300 such that the partially-assembled cartridge is held therein.

The partially-assembled cartridge 300 may include the flow director 308 which is surrounded by the reservoir substrate 312 (see, e.g., FIG. 3). The aerosol precursor composition 328 may be directed into the reservoir substrate 312 at the fourth assembly cell 502*d*' (see, FIG. 18). In this regard, as illustrated in FIG. 43, the filling apparatus 666' may include one or more filling needles 672' configured to direct the aerosol precursor composition 328 (see, FIG. 18) from an aerosol precursor composition supply 674' to the cartridges 300. However, in instances in which the reservoir substrate 312 is unable to absorb or otherwise receive the aerosol precursor composition 328 at the rate at which the aerosol precursor composition is directed into the partially-assembled cartridge 300, some of the aerosol precursor composition may overflow into the channel defined through the flow director 308.

Accordingly, the partially-assembled cartridge 300 may be filled at a relatively slower rate or the aerosol precursor composition 328 (see, FIG. 18) overflowing into the flow director 308 (see, e.g., FIG. 3) may be wasted. However, slowing the fill rate of the aerosol precursor composition 328 into the partially-assembled cartridge 300 (see, e.g., FIG. 3) may present a bottleneck that slows the entire cartridge assembly process. Accordingly, in some embodiments the system 400' may include features configured to allow for expedited filling of the partially assembled cartridge.

In this regard, as illustrated in FIG. 44, each of the receptacles 652' may include an aperture 676'. For example, the aperture 676' may extend through the bottom of the assembly carriage 506*d*'. The aperture 676' may be configured to direct a flow of air through the flow director 308. In this regard, as illustrated in FIG. 43, the cartridge filling subsystem 408' may further include a manifold 678'. The manifold 678' may include a plurality of cooperating outlets 680' that are configured to align with the apertures 676' (see, FIG. 44) defined at each of the receptacles 652' when the manifold engages a bottom surface of the assembly carriage 506*d*'.

The manifold 678' may be positioned at a location at the cartridge filling subsystem 408' at which the partially-assembled cartridges 300 (see, e.g., FIG. 3) are filled. Thereby, an actuator 682' (e.g., a pneumatic or hydraulic cylinder) may press the manifold 678' into engagement with the bottom of the assembly carriage 506*d*'. Air from an air supply 684', which may include an air compressor, may be directed into the manifold 678' out the cooperating outlets 680', into the apertures 676', and through the flow directors 308 (see, e.g., FIG. 3). Note that the air pressure and/or flow rate through the manifold 678' may be adjusted so as to resist entry of the aerosol precursor composition into the flow director 308 while avoiding applying too much air flow, which could blow the aerosol precursor composition out of the partially-assembled cartridge 300 during filling. In this regard, the air supply 684' may include a flow controller 686' such as a valve. Accordingly, the flow of air upwardly through the flow directors 308 (see, e.g., FIG. 3) may resist overflow of the aerosol precursor composition 328 (see, e.g., FIG. 18) into the flow directors to allow for relatively faster filling of the cartridges 300 with the aerosol precursor composition.

Note that the system 400 of FIG. 5 may also include a filling apparatus and features configured to prevent the aerosol precursor composition 328 overflowing into the flow director 308. In this regard, each of the receptacles 652 of the assembly carriage 506*d* of FIG. 15 may include an aperture 676 extending through to the bottom of the assembly carriage 506*d*. Thereby, as described above, air may blow up through each of the apertures 676 and into and through the flow tubes 308 during filling of the partially-assembled cartridges 300 (see, e.g., FIG. 3) with aerosol precursor composition 328.

However, in some embodiments the cartridge filling subsystem 408 may be configured to fill the partially-assembled cartridges 300 (see, e.g., FIG. 3) in stages. For example, the cartridge filling subsystem 408 may fill each row of the partially-assembled cartridges 300 received in the receptacles 652 of the assembly carriage 506*d* (see, FIG. 15) sequentially. In this regard, FIG. 45 illustrates a first manifold 678*a* configured to fill partially-assembled cartridges 300 in a first row 676*a* of the receptacles 652 of the assembly carriage 506*d* (see, FIG. 15). The first manifold 678*a* may include a row of cooperating outlets 680*a* that receive a flow of air from an air supply 684 to thereby direct air flow through the apertures 676 in the assembly carriage 506*d* and through the flow directors 308 of the partially-assembled cartridges 300 (see, e.g., FIG. 3) during filling thereof when the assembly carriage is directed over the first manifold by the assembly track 504*d*. After the partially-assembled cartridges 300 in the first row 652*a* of the receptacles 652 of the assembly carriage 506*d* (see, e.g., FIG. 15) are filled, the assembly track 504*d* may direct the assembly carriage 506*d* to a second manifold 678*b*, a portion of which is shown in FIG. 45, at which outlets 680*b* may direct air thorough a second row 652*b* of the receptacles (see, FIG. 15) in the assembly carriage 506*d* and through the flow directors 308. Thereafter, the assembly carriage 506*d* may be directed by the assembly track 504*d* to a third manifold that may direct the air through the flow directors 308 of partially-assembled cartridges 300 received in a third row 652*c* of the receptacles 652 (see, FIG. 15). Accordingly, the manifolds may be configured to accommodate sequential filling of the partially-assembled cartridges with aerosol precursor composition. Additional disclosure with respect to aerosol precursor composition filling systems is provided in U.S. Pat. Appl. Pub. No. 2016/0054345 to Watson et al., which is incorporated herein by reference in its entirety.

Returning to the system 400' of FIG. 18, the partially-assembled cartridge 300 may be directed to the fifth assembly cell 502*e*' via the fourth inter-cell transporter 512*d*' at which the mouthpiece 316 may be coupled to the outer body 314 after being filled with the aerosol precursor composition 328. The mouthpiece 316 may be affixed to the outer body via ultrasonic welding or any of various other affixation mechanisms and methods.

The partially-assembled cartridge 300 may then be directed via the fifth inter-cell transporter 512*e*' to the sixth assembly cell 502*f*' at which the labels 318 may be attached to complete the cartridge. In some embodiments the label 318 may be heat shrunk onto the partially-assembled cartridge 300 in order to provide a smooth and integral appearance. Following attachment of the label 318, the completed cartridges 300 may be directed via the sixth-inter-cell transporter 512*f*' to the seventh assembly cell 502*g*' at which the cartridge 300 may be packaged.

As noted above, the inspection subsystem 418 may be configured to inspect the cartridges 300 in various states of completion in each of the systems 400, 400'. As illustrated in FIG. 46, in one embodiment the inspection subsystem 418 may include a test fixture 422. The test fixture 422 may be configured to perform various electrical tests on partially or fully assembled cartridges 300 (see, e.g., FIG. 3). For example, the test fixture 422 may determine a resistance of the atomizer 310 (see, e.g., FIG. 3) of the cartridge 300 and compare the resistance to a desired resistance. Further, the test fixture 422 may transmit program code instructions to the electronic control component 306 of the cartridge 300 (see, e.g., FIG. 3). Additional description of operations that may be performed by the test fixture 422 is provided in U.S. Pat. Appl. Publ. No. 2015/0223522, which is incorporated herein by reference in its entirety.

As illustrated in FIG. 46, the test fixture 422 may include a funnel 424 configured to guide the base 302 of a cartridge 300 (see, e.g., FIG. 3), which may be partially or fully assembled into engagement with a receptacle 426. The receptacle 426 may define a size and shape similar to the coupler 202 of the control body 200 (see, FIG. 2). The receptacle 426 may include a plurality of electrical contacts 428A-C configured to engage the terminals of the cartridge 300. The electrical contacts 428A-C may be formed from conductive and relatively hard material, such as hardened steel, configured to withstand repeated engagement and disengagement.

A first electrical contact 428A may be configured to engage the first heating terminal 320*a* (see, e.g., FIG. 3), a second electrical contact 428B may be configured to engage the second heating terminal 320*b* (see, e.g., FIG. 3), and a third electrical contact 428C may be configured to engage the control component terminal 304 (see, e.g., FIG. 3). Thereby, the controller 417 (or a separate controller) may form an electrical circuit with the cartridge 300 to electrically communicate with the cartridge through the terminals 320*a*, 320*b* 304 and the electrical contacts to perform one or more operations as described above. In this regard, each of the electrical contacts 428A-C may be electrically insulated from one another. For example, insulators 430A, 430B may be positioned between the electrical contacts 428A-C to electrically insulate each of the electrical connectors from one another. For example, the insulators 430A, 430B may comprise polyether ether ketone (PEEK), or other electrically nonconductive materials.

However, engagement of the cartridge 300 (see, e.g., FIG. 3) with the receptacle 426 may require proper alignment therebetween or otherwise issues with respect to forming an electrical connection between the cartridge and the controller 417 may occur. In this regard, a poor electrical connection may cause the test to falsely indicate that the cartridge 300 is defective and/or programming of the electronic control component 306 (see, e.g., FIG. 3) may not occur.

Accordingly, in some embodiments the test fixture 422 may include a compliant member 432. The compliant member 432 may be configured to allow for movement of the receptacle 426 in one or more directions to facilitate engagement with the cartridge 300. For example, in one embodiment the compliant member 432 may be configured to allow for movement of the receptacle 426 in a plane perpendicular to an axis 434 along which the cartridge 300 may be inserted into the receptacle 426. However, in other embodiments the compliant member 432 may be configured to move in additional or alternative directions to facilitate engagement with the cartridge, such as along the axis 434 on which the cartridge 300 may be inserted into the receptacle 426.

The compliant member 432 may provide compliance in any number of manners. For example, the compliant member may include springs that allow for movement thereof. In another embodiment the compliant member 432 may comprise a resilient material (e.g., rubber) that allows for movement of the receptacle 426 when the cartridge 300 (see, e.g., FIG. 3) is engaged therewith. In some embodiments the compliant member 432 may be configured to return the receptacle 426 to an initial, central position aligned with the axis 434 of insertion after each engagement with a cartridge 300 (see, e.g., FIG. 3). For example, the resiliency of the material defining the compliant member 432 or springs may return the compliant member to the central position. Thereby, engagement with each cartridge 300 may be facilitated because the receptacle 426 may be substantially aligned with the axis 434 along which the cartridge 300 may be inserted into the receptacle 426 before each insertion.

As may be understood, various other configurations of test fixtures may be employed to test or otherwise perform operations on cartridges. For example, FIG. 47 illustrates an alternate embodiment of a test fixture 422' that may be employed in the inspection subsystem 418 (see, e.g., FIG. 4) in embodiments of the present disclosure. As illustrated, the test fixture 422' may include a receptacle 426'. In some embodiments a funnel 424' may guide the cartridges 300 (see, e.g., FIG. 3) into the receptacle. The receptacle 426' may include electrical contacts 428A'-C' which may be electrically insulated from one another and configured to engage a respective one of the first heating terminal 320*a*, the second heating terminal 320*b*, and the control component terminal 304 (see, e.g., FIG. 3), as noted above. The electrical contacts 428A'-C' may be formed from conductive and relatively hard material, such as hardened steel.

The test fixture 422' may further comprise components configured to provide the receptacle 426' with compliance in order to improve connectivity with the cartridge 300 (see, e.g., FIG. 3), as noted above. The test fixture 422 of FIG. 45 includes a compliant member 432 that allows the entire receptacle 426 to move as a whole. However, in other embodiments the compliant member may be configured to allow portions of the receptacle to move independently.

For example, as illustrated in FIG. 47, the electrical contacts 428A'-C' may be independently moveable along a first horizontal axis 436'. In this regard, each electrical contact 428A'-C' may be configured to linearly slide along the first horizontal axis 436' to accommodate the specific position of the cartridge 300 (see, e.g., FIG. 3) during insertion thereof into the receptacle 426'. Thereby, each of the electrical contacts 428A'-C' may form an electrical connection with the cartridge 300.

Further, each of the electrical contacts 428A'-C' may be configured to move along a second horizontal axis 438', which may be perpendicular to the first horizontal axis 436', to allow for movement in any direction within a horizontal plane perpendicular to an axis 434' of insertion of the cartridge 300 into the receptacle 426'. For example, the test fixture 422' may include a rail 440' upon which a slide bearing 442' is configured to slide. The receptacle 426' may be engaged with the slide bearing 442' to allow for movement thereof along the second horizontal axis 438' as noted above. Further, springs or other devices may be configured to return the receptacle 426 to a central position aligned with the axis 434' of insertion to facilitate engagement with each cartridge 300. Accordingly, the test fixtures of the present disclosure may be configured in various manners to provide a degree of compliance that may improve connectivity with the partially or fully assembled cartridges such that testing and other functions may occur even when the cartridges are not inserted perfectly into the center of the test fixture.

In an additional embodiment an aerosol delivery device assembly method is provided. As illustrated in FIG. 48, the method may include providing a substantially-continuous input comprising a plurality of heating elements engaged with a substantially-continuous liquid transport element at operation 902. Further, the method may include providing a first heating terminal and a second heating terminal at operation 904. The method may additionally include engaging the first heating terminal and the second heating terminal with one of the heating elements at operation 906. The method may also include welding the first heating terminal and the second heating terminal to the one of the heating elements. The method may further include cutting the substantially-continuous input to singulate the one of the heating elements to which the first heating terminal and the second heating terminal are attached and a corresponding liquid transport segment from the substantially-continuous input at operation 910.

In some embodiments welding the first heating terminal and the second heating terminal to the one of the heating elements at operation 908 may comprise laser welding the first heating terminal and the second heating terminal to the one of the heating elements with a laser welder by focusing a laser at the first heating terminal and the second heating terminal. The laser welder, the first heating terminal, and the second heating terminal may remain stationary during and between welding the first heating terminal and the second heating terminal to the one of the heating elements. In this regard, as described above with respect to FIG. 22, the laser welder 536' may remain stationary, whereas the adjustable optical lens 542' may focus the laser beam 538' at differing locations.

In some embodiments providing the first heating terminal and the second heating terminal at operation 904 may comprise providing an assembly comprising a base and a flow director, wherein the first heating terminal and the second heating terminal extend through the flow director. Further, engaging the first heating terminal and the second heating terminal with the one of the heating elements at operation 906 may comprise rotating a rotary transporter.

FIG. 49 illustrates an additional aerosol delivery device assembly method. As illustrated, the method may include grasping an assembly with a plurality of clamps respectively comprising a first finger and a second finger at operation 1002. The assembly may include a flow director, an atomizer, a first heating terminal, and a second heating terminal. The first heating terminal and the second heating terminal may be coupled to the atomizer. Further, the method may include opening the clamps at operation 1004. The method may additionally include positioning a reservoir substrate in contact with the assembly at operation 1006. The method may further include closing the clamps around the assembly such that the substrate wraps at least partially around the assembly.

In some embodiments positioning the reservoir substrate in contact with the assembly at operation 1006 may include engaging the substrate with a substrate gripper comprising one or more protrusions configured to apply a negative pressure thereto. Further, closing the clamps at operation 1008 may include receiving the one or more protrusions in one or more gaps positioned between the clamps. The method may additionally include retracting the substrate gripper after closing the clamps by retracting the one or more protrusions through the one or more gaps.

The method may further comprise engaging a cap with the assembly while positioning the reservoir substrate in contact with the assembly at operation 1006. Additionally, opening the clamps at operation 1004 may comprise inserting an actuator pin into engagement with the clamps to sequentially open the clamps. Further, closing the clamps may include retracting the actuator pin to sequentially close the clamps at operation 1008.

Additionally, FIG. 50 illustrates an aerosol delivery device ultrasonic welding method. As illustrated, the method may include engaging a welding clamp with a cartridge comprising a base and an outer body by clamping a plurality of base protrusions against the base of the cartridge and positioning a plurality of outer body protrusions adjacent to the outer body, a distance between the outer body protrusions being greater than a dimension of the cartridge between the outer body protrusions at operation 1102. Further, the method may include engaging an ultrasonic horn with the outer body opposite from the base at operation 1104. The method may additionally include ultrasonically vibrating the ultrasonic horn to weld the outer body to the base at operation 1106. The method may further include constraining movement of the outer body with the outer body protrusions to maintain alignment of the outer body with respect to the base at operation 1108 while ultrasonically vibrating the ultrasonic horn at operation 1106.

In some embodiments engaging the welding clamp with the cartridge at operation 1102 may include positioning the outer body protrusions out of contact with the outer body prior to ultrasonically vibrating the ultrasonic horn at operation 1106. Constraining movement of the outer body with the outer body protrusions at operation 1108 may include positioning the outer body between a groove and a substantially flat face of the outer body protrusions.

An aerosol delivery device cartridge filling method is also provided. As illustrated in FIG. 51, the method may include dispensing an aerosol precursor composition into a partially-assembled cartridge comprising a flow director at operation 1202. Further, the method may include directing a flow of air through the flow director at operation 1204 while dispensing the aerosol precursor composition into the partially-assembled cartridge at operation 1202.

In some embodiments directing the flow of air through the flow director at operation 1204 may comprise directing the flow of air upwardly through the flow director. Further, directing the aerosol precursor composition into the partially-assembled cartridge at operation 1202 may include directing the aerosol precursor composition into contact with a reservoir substrate extending at least partially around the flow director. The method may further comprise positioning the partially-assembled cartridge in an assembly carrier. Additionally, directing the flow of air through the flow director at operation 1204 may comprise directing the flow of air through the assembly carrier. Directing the flow of air through the flow director at operation 1204 may further comprise engaging a manifold with the assembly carrier and directing the flow of air from the manifold to the assembly carrier.

Further, the present disclosure provides an aerosol delivery device test method. As illustrated in FIG. 52, the method may include inserting a cartridge for an aerosol delivery device along an axis into a receptacle of a test fixture, the cartridge comprising a plurality of terminals and the receptacle comprising a plurality of electrical contacts configured to engage a respective one of the terminals at operation 1302. Further, the method may include allowing movement of the receptacle in a plane perpendicular to the axis along which the cartridge is inserted into the receptacle to facilitate engagement of the electrical contacts with the terminals of the cartridge at operation 1304. The method may additionally include electrically communicating with the cartridge through the terminals and the electrical contacts at operation 1306.

In some embodiments of the method, allowing movement of the receptacle at operation 1304 may comprise fixedly securing the electrical contacts to one another such that each of the electrical contacts moves in unison. In another embodiment of the method, allowing movement of the receptacle at operation 1304 may comprise allowing each of the electrical contacts to move independently in at least one direction.

As noted above, the systems 400, 400' may include a controller 417. The controller 417 may be configured to execute computer code for performing the operations described herein. As illustrated in FIG. 53, the controller 417 may comprise a processor 1402 that may be a microprocessor or a controller for controlling the overall operation thereof. In one embodiment the processor 1402 may be particularly configured to perform the functions described herein. The controller 417 may also include a memory device 1404. The memory device 1404 may include non-transitory and tangible memory that may be, for example, volatile and/or non-volatile memory. The memory device 1404 may be configured to store information, data, files, applications, instructions or the like. For example, the memory device 1404 could be configured to buffer input data for processing by the processor 1402. Additionally or alternatively, the memory device 1404 may be configured to store instructions for execution by the processor 1402.

The controller 417 may also include a user interface 1406 that allows a user to interact therewith. For example, the user interface 1406 can take a variety of forms, such as a button, keypad, dial, touch screen, audio input interface, visual/image capture input interface, input in the form of sensor data, etc. Still further, the user interface 1406 may be configured to output information to the user through a display, speaker, or other output device. A communication 1408 interface may provide for transmitting and receiving data through, for example, a wired or wireless network 1410 such as a local area network (LAN), a metropolitan area network (MAN), and/or a wide area network (WAN), for example, the Internet.

The controller 417 may further comprise a cartridge assembly module 1412. The cartridge assembly module may be configured to execute computer code to perform the aerosol delivery device assembly method operations described herein. The cartridge assembly module 1412 and/or other components of the controller 417 may be configured to execute program code instructions stored on a non-transitory computer readable medium. In this regard, an embodiment of a non-transitory computer readable medium for storing computer instructions executed by a processor (e.g., processor 1402) in a controller (e.g., controller 417) configured to assemble a cartridge for an aerosol delivery device is provided. The non-transitory computer readable medium may comprise program code instructions for performing the cartridge assembly method operations described herein.

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium for controlling the above-described operations. In particular, computer readable code may be configured to perform each of the operations of the methods described herein and embodied as computer readable code on a computer readable medium for controlling the above-described operations. In this regard, a computer readable storage medium, as used herein, refers to a non-transitory, physical storage medium (e.g., a volatile or non-volatile memory device, which can be read by a computer system. Examples of the computer readable medium include read-only memory, random-access memory, CD-ROMs, DVDs, magnetic tape, and optical data storage devices. The computer readable medium can also be distributed over network-coupled computer systems so that the computer readable code is stored and executed in a distributed fashion.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

The invention claimed is:

1. An assembly carriage configured to assemble a cartridge for an aerosol delivery device, the assembly carriage comprising:

a platform;

a first nest disposed on the platform and configured to receive a partially-assembled cartridge in a first orientation; and a second nest disposed on the platform and configured to receive the partially-assembled cartridge in a second orientation that differs from the first orientation.

2. The assembly carriage of claim 1, wherein the first nest comprises a receptacle configured to receive a base of the partially-assembled cartridge such that the partially-assembled cartridge defines a substantially vertical configuration.

3. The assembly carriage of claim 2, wherein the second nest comprises one or more clamps configured to receive and hold an atomizer in a substantially horizontal configuration.

4. The assembly carriage of claim 3, wherein the second nest comprises a recess configured to hold the partially-assembled cartridge in a substantially horizontal configuration.

5. The assembly carriage of claim 4, wherein the recess of the second nest is configured to hold the partially-assembled cartridge such that a first heating terminal and a second heating terminal thereof are in contact with a heating element of the atomizer.

6. The assembly carriage of claim 3, wherein the clamps are configured to extend on first and second opposing sides of the partially-assembled cartridge.

7. The assembly carriage of claim 1, wherein the first nest comprises:

a clamp configured to engage a reservoir substrate; and a recess configured to receive a partially-assembled cartridge, the recess being aligned and recessed with respect to the clamp such that the reservoir substrate wraps at least partially around the partially-assembled cartridge during insertion of the partially-assembled cartridge into the recess.

8. The assembly carriage of claim 7, wherein the clamp comprises a plurality of prongs that extend on first and second opposing sides of the first nest.

9. The assembly carriage of claim 8, wherein the first nest further defines first and second openings positioned at the first and second opposing sides of the first nest, the first and second openings being configured to receive an end effector that clamps the reservoir substrate against the partially-assembled cartridge.

10. The assembly carriage of claim 8, wherein the first and second opposing sides of the first nest are elevated with respect to the recess.

11. The assembly carriage of claim 7, wherein the second nest comprises a receptacle configured to receive a base of the partially-assembled cartridge such that the partially-assembled cartridge defines a substantially vertical configuration, and wherein the recess of the first nest is configured to hold the partially-assembled cartridge in a substantially horizontal configuration.

12. A method for assembling a cartridge for an aerosol delivery device, the method comprising:

transporting an assembly carriage to an assembly cell, the assembly carriage comprising a platform, a first nest disposed on the platform, and a second nest disposed on the platform;

receiving a partially-assembled cartridge in a first orientation in the first nest; and receiving the partially-assembled cartridge in a second orientation that differs from the first orientation in the second nest.

13. The method of claim 12, wherein receiving the partially-assembled cartridge in the first orientation in the first nest comprises receiving a base of the partially-assembled cartridge such that the partially-assembled cartridge defines a substantially vertical configuration.

14. The method of claim 13, further comprising receiving and holding an atomizer in a substantially horizontal configuration at the second nest.

15. The method of claim 14, wherein receiving the partially-assembled cartridge in the second orientation in the second nest comprises receiving the partially-assembled cartridge in a recess configured to hold the partially-assembled cartridge in a substantially horizontal configuration.

16. The method of claim 15, wherein receiving the partially-assembled cartridge in the recess comprises holding the partially-assembled cartridge such that a first heating terminal and a second heating terminal thereof are in contact with a heating element of the atomizer.

17. The method of claim 14, wherein receiving and holding the atomizer in the substantially horizontal configuration at the second nest comprises clamping the atomizer on first and second opposing sides of the partially-assembled cartridge.

18. The method of claim 12, further comprising engaging a reservoir substrate with a clamp at the first nest, wherein receiving the partially-assembled cartridge in the first orientation in the first nest comprises inserting the partially-assembled cartridge into a recess, the recess being aligned and recessed with respect to the clamp such that the reservoir substrate wraps at least partially around the partially-assembled cartridge during insertion of the partially-assembled cartridge into the recess.

19. The method of claim 18, wherein engaging the reservoir substrate with the clamp comprises engaging the reservoir substrate with a plurality of prongs that extend on first and second opposing sides of the first nest.

20. The method of claim 19, further comprising directing an end effector into first and second openings positioned at the first and second opposing sides of the first nest; and clamping the reservoir substrate against the partially-assembled cartridge with the end effector.

21. The method of claim 19, wherein engaging the prongs with the reservoir substrate comprises pressing the reservoir substrate against the first and second opposing sides of the first nest, the first and second opposing sides of the first nest being elevated with respect to the recess.

22. The assembly carriage of claim 1, wherein the first nest and the second nest are disposed on the platform orthogonally to one another.

23. The assembly carriage of claim 1, wherein the first nest comprises a plurality of aligned first nests.

24. The assembly carriage of claim 1, wherein the second nest comprises a plurality of aligned second nests.

* * * * *